US005627286A

United States Patent [19]

Ramalingam et al.

[11] Patent Number: 5,627,286
[45] Date of Patent: May 6, 1997

[54] HETEROATOM-BEARING LIGANDS AND METAL COMPLEXES THEREOF

[75] Inventors: Kondareddiar Ramalingam, Dayton; Natarajan Raju, Kendall Park, both of N.J.

[73] Assignee: Bracco International B.V., Amsterdam

[21] Appl. No.: 472,058

[22] Filed: Jun. 6, 1995

Related U.S. Application Data

[60] Division of Ser. No. 242,093, May 18, 1994, which is a continuation-in-part of Ser. No. 77,981, Jun. 15, 1993, abandoned.

[51] Int. Cl.⁶ .......................... C07C 249/00; C07F 5/00; C07D 233/54; A61K 51/04
[52] U.S. Cl. .................. 548/341.1; 564/253; 564/268; 534/10; 534/14; 424/1.65; 424/1.53; 524/99; 524/107; 548/518; 548/100; 546/184; 544/63; 544/98; 544/224; 544/336
[58] Field of Search .............................. 548/341.1, 518, 548/100; 564/253, 268; 534/10, 14; 424/1.65, 1.53; 524/99, 107; 544/63, 98, 224, 336; 546/184

[56] References Cited

U.S. PATENT DOCUMENTS

| | | |
|---|---|---|
| 3,369,121 | 2/1968 | Bruno et al. . |
| 3,920,995 | 11/1975 | Czaplinski et al. . |
| 4,071,613 | 1/1978 | Hunter, Jr. . |
| 4,193,979 | 3/1980 | Frank et al. . |
| 4,272,503 | 6/1981 | Camin et al. . |
| 4,311,689 | 1/1982 | Ruddock . |
| 4,363,793 | 12/1982 | Blau et al. . |
| 4,431,626 | 2/1984 | Henze . |
| 4,444,690 | 4/1984 | Fritzberg . |
| 4,462,992 | 7/1984 | Agrawal et al. . |
| 4,615,876 | 10/1986 | Troutner et al. . |
| 4,638,051 | 1/1987 | Burns et al. . |
| 4,758,682 | 7/1988 | Collins et al. . |
| 4,789,736 | 12/1988 | Canning et al. . |
| 4,818,813 | 4/1989 | Nowotnik et al. . |
| 4,849,511 | 7/1989 | Verbruggen . |
| 4,871,836 | 10/1989 | Francescono et al. . |
| 4,880,616 | 11/1989 | Azuma et al. . |
| 4,895,960 | 1/1990 | Deutsch . |
| 4,925,650 | 5/1990 | Nosco et al. . |
| 4,980,147 | 12/1990 | Fritzberg et al. . |
| 4,986,979 | 1/1991 | Morgan, Jr. et al. . |
| 4,988,496 | 1/1991 | Srinivasan et al. . |
| 5,026,829 | 6/1991 | Deutsch . |
| 5,037,631 | 8/1991 | Nosco . |
| 5,071,636 | 12/1991 | Yamauchi et al. . |
| 5,075,099 | 12/1991 | Srinivasan et al. . |
| 5,089,249 | 2/1992 | Fritzberg et al. . |
| 5,091,514 | 2/1992 | Fritzberg et al. . |
| 5,096,693 | 3/1992 | Azuma et al. . |
| 5,101,041 | 3/1992 | Troutner et al. .......... 548/518 |
| 5,104,638 | 4/1992 | Nosco . |
| 5,116,596 | 5/1992 | Bremer et al. . |
| 5,116,598 | 5/1992 | Nosco . |
| 5,164,175 | 11/1992 | Bremer et al. . |
| 5,164,176 | 11/1992 | Gustavson et al. . |
| 5,187,264 | 2/1993 | Verbruggen . |
| 5,302,370 | 4/1994 | Neumeier et al. . |
| 5,387,692 | 2/1995 | Riley et al. . |

FOREIGN PATENT DOCUMENTS

| | | |
|---|---|---|
| 61290/90 | 3/1991 | Australia . |
| 92/12148 | 9/1992 | Australia . |
| 92/12147 | 9/1992 | Australia . |
| 2023595 | 3/1991 | Canada . |
| 123504 | 10/1984 | European Pat. Off. . |
| 163119 | 12/1985 | European Pat. Off. . |
| 179608 | 4/1986 | European Pat. Off. . |
| 0179608A2 | 4/1986 | European Pat. Off. . |
| 194843 | 9/1986 | European Pat. Off. . |
| 344724 | 12/1989 | European Pat. Off. . |
| 417870 | 3/1991 | European Pat. Off. . |
| 441491 | 8/1991 | European Pat. Off. . |
| 502595A2 | 3/1992 | European Pat. Off. . |
| 502594A1 | 9/1992 | European Pat. Off. . |
| 544412 | 6/1993 | European Pat. Off. . |
| 4025788A1 | 2/1992 | Germany . |
| 2093451 | 9/1982 | United Kingdom . |
| 89/10759 | 11/1989 | WIPO . |
| 90/05733 | 5/1990 | WIPO . |
| 90/10463 | 9/1990 | WIPO . |
| 91/18908 | 12/1991 | WIPO . |
| 92/07860 | 5/1992 | WIPO . |
| 93/06148 | 4/1993 | WIPO . |
| 94/08949 | 4/1994 | WIPO . |

OTHER PUBLICATIONS

Elliott et al., "Synthesis of Potential Antiradiation Agents from 3-substituted 2-oxazolidinones derived from Phenol, Benzenethiol and Related Compounds", J. Med. Chem., vol. 12, No. 2, pp. 253–257, (1969).

Boschman et. al., "In vitro inhibition of ADP-induced patelet aggregation by O-(aminoalkyl) oxime ethers" Eur. J. Med. Chem.–ChemTherapeutica, Jul.–Aug. 1980, 15, No. 4 pp. 351–356. (1980).

Chapman, J.D., "Measurement of Tumor Hypoxia by Invasive and Non-Invasive Procedures: A Review of Recent Clinical Studies", Radiother. Oncol., 20, pp. 13–19 (1991).

Martin, G.V. et al., "Enhanced Binding of the Hypoxic Cell Marker [³H]Fluoromisonidazole in Ischemic Myocardium", J. Nucl. Med., vol. 30, No. 2, 194–201 (1989).

Hoffman, J.M. et al., "Binding of the Hypoxia Tracer [³H]Misonidazole in Cerebral Ischemia". Stroke, 18:168–176 (1987).

Koh, W.J. et al., "Hypoxia Imaging of Tumors Using [F-18] Fluoromisonidazole", J. Nucl. Med., 30,789 (No. 252) (1989).

(List continued on next page.)

Primary Examiner—Gary E. Hollinden
Assistant Examiner—Michael G. Hartley
Attorney, Agent, or Firm—George P. Hoare; Donald L. Rhoads

[57] ABSTRACT

Novel compounds containing a heteroatom-bearing bridge and novel complexes of these compounds with metals. The novel compounds and complexes are useful in diagnostic and therapeutic methods.

12 Claims, No Drawings

OTHER PUBLICATIONS

Biskupiak, J.E. et al., "Synthesis of an (Iodovinyl)misonidazole Derivative for Hypoxia Imaging", J. Med. Chem., 34, pp. 2165–2168 (1991).

Chapman, J.D., "The Detection and Measurement of Hypoxic Cells in Solid Tumors", Cancer, Vo. 54, No. 11, pp. 2441–2449 (1984).

Kedderis, G.L. et al, "The Metabolic Activation of Nitroheterocyclic Therapeutic Agents", Drug Metabolism Reviews, 19(1), pp. 33–62 (1988).

Adams, G.E. et al., "Hypoxia–Mediated Nitro–Heterocyclic Drugs in The Radio–and Chemothrapy of Cancer", Biochemical Pharmacology, vol. 35, No. 1, pp. 71–76 (1986).

Brown, D.M. et al., "Structure–Activity Reationships of 1–Substituted 2–Nitroimidazoles: Effect of Partition Coefficient and Side–chain Hydroxyl Groups on Radiosensitization In Vitro", Radiation Research, 90, pp. 98–108 (1982).

Adams, G.E., et al., "Structure Activity Relationships in the Development of Hypoxic Cell Radiosensitizers. I. Sensitization Efficiency", Int. J. Radiat. Biol., vol. 35, No. 2, pp. 133–150 (1979).

Adams, G.E., et al., "Structure Activity Relationships in the Development of Hypoxic Cell Radiosensitizers. III. Effects of Basic Substituents in Nitromidazole Sidechains", Int. J. Radiat. Biol., vol. 38, No. 6, pp. 613–626 (1980).

Jerabek, P.A., et al., "Synthesis and Biodistribution of $^{18}$F–Labeld Fluoronitroimidazoles: Potential In Vivo Markers of Hypoxic Tissue", Appl. Radiat. Isot. vol. 37, No. 7, pp. 599–605 (1986).

Martin, G.V. et al, "Fluoromisonidazole A Metabolic Marker of Myocyte Hypoxia", Circulation Research, 67, pp. 240–244 (1990).

Shelton, M.E. et al., "In Vivo Delineation of Myocardial Hypoxia During Coronary Occlusion Using Fluorin–18 Fluoromisonidazole and Positron Emission Tomography: A Potntial Approach for Idntification of Jeopardized Myocardium", J. Am. College Cardiology, vol. 16, No. 2, pp. 477–485 (Aug. 1990).

Mannan, R.H. et al., "Radioiodinated 1–(5–Iodo–5–deoxy–β–D–arabinofuranosyl)–2–nitroimidazole (Iodazomycin Arabinoside: IAZA): A Novel Marker of Tissue Hypoxia", The Journal of Nuclear Medicine, vol. 32, No. 9, pp 1764–1770 (1991).

Parker, D., "Harnessing the Kinetic Stability of Macrocyclic Complexes In Vivo," presented at the 16th Int. Symp. on Macrocyclic Chemistry, Univ. of Sheffield, UK (Sep. 1–6, 1991).

Yang Kixi, et al., "Synthesis of Metronidazole Derivative and Its Distribution in Sarcoma 180 Bearing Mice", J. of Medical Colleges of PLA; 2(3) pp. 265–269 (1987).

Volkert, W.A. et al, "$^{99m}$Tc–propylene amine oxime (99mTc–PnAO); a potential brain radiopharmaceutical", Eur. J. Nucl. Med., 9, pp. 511–516 (1984).

Kung, H.F., et al., "Synthesis and Biodistribution of Neutral Lipid–Soluble Tc–99m Complexes that Cross the Blood–Brain Barrier", The Journal of Nuclear Medicine, 25, pp. 326–332 (1984).

Lever, S.Z. et al., "Design, Preparation, and Biodistribution of a Technetium–99m Triaminedithiol Complex to Assess Regional Cerebral Blood Flow", J. Nucl. Med., 26, pp. 1287–1294 (1985).

Jurisson et al., "Synthesis, Characterization, and X–ray Structural Determination of Technetium (V)–Oxo–Tetradentate Amine Oxime Complexes", Inorg. Chm., 25, pp. 543–549 (1986).

Ding et al., "Review and Prospectives of Brain Radiopphamaceuticals", Nucl. Sci. J., 29(5), pp. 341–348 (1992).

Fattorusso et al., J. Chem. Soc., Daltons Trans., p. 752 (1970).

Moody et al., J. Chem. Soc. Perkin Trans. 1, (1), pp. 18–24 (1972).

Svetkin et al., Zh. Obshch Khim, 41(11), pp. 2553–2555 (1971).

Hook et al., Anti–Cancer Drug Res., 4(3), pp. 173–190 (1989).

Curtius, Hechtenberg, J. Pract. Chem., 105, 314 (1922).

Orna et al., "Correlation of Kinetic Parameters of Nitroreductase Enzymes with Redox Properties of Nitroaromatic Compounds", J. Biol. Chem., vol. 264, 21, pp. 12379–12384 (1989).

Murmann, K., "The Interaction of 2–Methyl–2–amino–3–butanone Oxime with Nickel (II) and Copper (II) Ions", J. Am. Chem. Soc., pp. 4174–4180 (1958).

Vassian et al., "Aromatization of an Aliphatic Amine Oxime Nickel (II) Complex by Molecular Oxygen", Inorg. Chemistry, vol. 6, No. 11, pp. 2043–2046 (1967).

Murmann et al., "An Unsymmetrical transDinitrocobalt (III) Complex. A Crystal Structure Determination", Inorg. Chem., vol. 12, No. 11, pp. 2625–2631 (1973).

Somin et al. "Oximes of w–dimethylaminoalkanals and their derivatives." Zh. Organ. Khim. vol. 1 (II), pp. 1973–1976, (1965) (Russian) [Chem Abs.] vol. 64, p. 9582(f).

Corbin, et. al. "Substituted Cysteame Ligands and Their Complexes with Molybdenum(VI)", Inorg. Chem. vol. 23, pp. 3404–4312, (1984).

Bryson, et. al. "Neutral Technitium(V) Complexes with Amide–Thiol–Thioether Chelating Ligands" Inor. Chem. vol. 27, pp. 2154–2161, (1988).

Panakaskie et. al., Synthetic Communications, vol. 19, pp. 339–344 (1966).

Biniakiewicz et. al. "A New, General synthetic Route to Multidentate N,S Ligands for Use in Technetium–99m Radiopharmaceuticals." J. Med. Chem., vol. 35, pp. 274–279, (1992).

HETEROATOM-BEARING LIGANDS AND METAL COMPLEXES THEREOF

This is a divisional of application Ser. No. 08/242,093, filed May 18, 1994, which is a continuation-in-part of Ser. No. 08/077,981, filed on Jun. 15, 1993 by Ramalingam et al., now abandoned wherein the aforementioned patent application is incorporated by reference herein in its entirety.

FIELD OF THE INVENTION

The present invention relates to novel compounds containing a heteroatom-bearing bridge, and to novel complexes of these compounds with metals. The novel compounds and complexes of the present invention find utility in diagnostic and therapeutic methods.

BACKGROUND OF THE INVENTION

Metal complexes, such as those containing radioactive metals, are finding increasing use as diagnostic and therapeutic agents. Of particular interest are those complexes containing bioactive moieties capable of being selectively taken up at a desired site to facilitate evaluation or treatment of a subject.

The present invention addresses the need in the art for such complexes, including the ligands from which they are prepared, particularly such complexes containing hypoxia-localizing moieties.

SUMMARY OF THE INVENTION

The present invention provides novel compounds, also referred to herein as ligands, of the following formulae Ia, Ib and Ic:

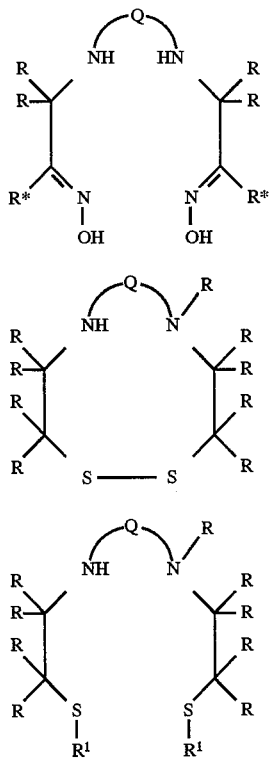

where

Q is the group —(C(RR))$_{m1}$—Y$^1$(C(RR))$_{m2}$—(Y$^2$—(C(RR))$_{m3}$)$_n$—, where Y$^1$ and Y$^2$ are independently —NR—, —O—, —S—, —SO—, —SO$_2$— or —Se—;

n is an integer selected from 0 or 1; and m1, m2 and m3 are integers independently selected from 0 to 4, provided that the sum of m1 and m2 is greater than zero; all R and R* groups are independently:

(i) R$^2$;

(ii) halogen, especially fluoro;

(iii) —OR$^2$;

(iv) —C(O)—OR$^2$;

(v) —C(O)—N(R$^2$)$_2$;

(vi) —N(R$^2$)$_2$;

(vii) -alkyl—C(O)—OR$^2$;

(viii) -alkyl—C(O)—N(R$^2$)$_2$;

(ix) -alkyl—N(R$^2$)$_2$;

(x) -aryl—C(O)—OR$^2$;

(xi) -aryl—C(O)—N(R$^2$)$_2$;

(xii) -aryl—N(R$^2$)$_2$;

(xiii) acyl;

(xiv) acyloxy;

(xv) heterocyclo;

(xvi) hydroxyalkyl;

(xvii) —SO$_2$—R$^2$;

(xviii) -alkyl—SO$_2$—R$^2$;

(xix) —(A)p-R$^3$, where A is a linking group, p is 0 or a positive integer, and R$^3$ is a bioactive moiety; or (xx) two R groups, or an R group and an R* group, taken together with the one or more atoms to which they are bonded, form a saturated or unsaturated, spiro or fused, carbocyclic (such as fused 1,2-phenyl) or heterocyclic ring which may be unsubstituted or substituted by one or more groups selected from the groups (i) to (xix) above;

with the proviso that a carbon atom bearing an R group is not directly bonded to more than one heteroatom;

R$^1$ is hydrogen; a thiol protecting group; or the group —(A)p-R$^3$ defined above; and R$^2$ is independently hydrogen, alkyl, alkenyl, alkynyl, or aryl.

The present invention also provides complexes of the aforementioned compounds of the formulae Ia, Ib and Ic with metals, preferably rhenium or technetium, and the use of these complexes in diagnostic and therapeutic methods. Further provided by the present invention are kits for preparing the metal complexes of the present invention.

In preferred embodiments, the present invention provides complexes containing bioactive moieties, such as hypoxia-localizing moieties, which retain the biochemical behavior and affinity of the free moieties, and which are capable of rapidly providing increased amounts of a desired radionuclide selectively to targeted areas; which may be labeled at ambient temperature with suitable, easy-to-use radionuclides; and which are membrane permeable, allowing intracellular delivery.

DESCRIPTION OF THE INVENTION

The present invention is described further as follows.

Definitions

Listed below are definitions of terms used to describe the present invention. These definitions apply to the terms as they are used throughout the specification unless otherwise indicated.

The terms "alkyl" or "alk", as used herein alone or as part of another group, denote optionally substituted, straight and branched chain saturated hydrocarbon groups, preferably having 1 to 12 carbons in the normal chain, most preferably lower alkyl groups. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents include one or more of the following groups: halo, alkoxy, arylalkyloxy (e.g., benzyloxy), alkylthio, alkenyl, alkynyl, aryl, cycloalkyl, cycloalkenyl, hydroxy, carboxyl (—COOH), amino, alkylamino, dialkylamino, formyl, alkylcarbonyloxy, alkylcarbonyl, heterocyclo, aryloxy or thiol (—SH). Preferred alkyl groups are unsubstituted alkyl, haloalkyl, arylalkyl, aminoalkyl, alkylaminoalkyl, dialkylaminoalkyl, aralkoxyalkyl, aryloxyalkyl, hydroxyalkyl and alkoxyalkyl groups.

The terms "lower alk" or "lower alkyl" as used herein, denote such optionally substituted groups as described above for alkyl having 1 to 4 carbon atoms in the normal chain.

The terms "alkoxy" or "alkylthio" denote an alkyl group as described above bonded through an oxygen linkage (—O—) or a sulfur linkage (—S—), respectively. The term "alkylcarbonyl", as used herein, denotes an alkyl group bonded through a carbonyl group. The term "alkylcarbonyloxy", as used herein, denotes an alkyl group bonded through a carbonyl group which is, in turn, bonded through an oxygen linkage.

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, butenyl, pentenyl, hexenyl, heptenyl, octenyl, nonenyl, decenyl, and the like. Exemplary substituents include one or more alkyl groups as described above, and/or one or more groups described above as alkyl substituents.

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include ethynyl, propynyl, butynyl, pentynyl, hexynyl, heptynyl, octynyl, nonynyl, decynyl, and the like. Exemplary substituents include one or more alkyl groups as described above, and/or one or more groups described above as alkyl substituents.

The term "cycloalkyl", as used herein alone or as part of another group, denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents.

The term "cycloalkenyl", as used herein alone or as part of another group, denotes such optionally substituted groups as described above for cycloalkyl, further containing at least one carbon to carbon double bond forming a partially unsaturated ring. Exemplary substituents include one or more alkyl groups as described above, and/or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above and/or groups described above as alkyl substituents. Preferred aryl groups are unsubstituted aryl and hydroxyaryl.

The term "carbocyclic", as used herein alone or as part of another group, denotes optionally substituted saturated, partially unsaturated or aromatic homocyclic hydrocarbon ring systems such as the cycloalkyl, cycloalkenyl or aryl groups described above.

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom off the ring system. Preferred groups include those of the following formula, which may be bonded through any atom of the ring system:

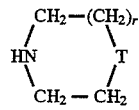

where r is 0 or 1 and T is —O—, —S—, —N—$R^8$ or —CH—$R^8$ where $R^8$ is hydrogen, alkyl, aryl or arylalkyl. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, morpholinyl, piperazinyl, 4-alkylpiperazinyl, 4-alkylpiperidinyl, 3-alkylpyrrolidinyl, oxazolyl, pyrazolyl, thiophenyl, pyridazinyl, thiazolyl, triazolyl, pyrimidinyl, 1,4-dioxanyl, benzoxadiazolyl, and benzofurazanyl. Exemplary substituents include one or more alkyl groups as described above and/or one or more groups described above as alkyl substituents.

The terms "halogen", "halo", or "hal", as used herein alone or as part of another group, denote chlorine, bromine, fluorine, and iodine.

The term "acyl", as used herein alone or as part of another group, denotes the moiety formed by removal of the hydroxyl group from the group —COOH of an organic carboxylic acid. Exemplary such groups include alkylcarbonyl, arylcarbonyl, or carbocyclo- or heterocyclo-carbonyl. The term "acyloxy", as used herein alone or as part of another group, denotes an acyl group as described above bonded through an oxygen linkage (—O—).

For the above optionally substituted groups, reference to a specific substituent may be made without excluding the presence of other substituents. Thus, for example, "hydroxyalkyl" is a straight or branched chain saturated hydrocarbon group bearing at least one hydroxy substituent and no other or, optionally, one or more additional, substituents.

The term "thiol protecting group", as used herein, denotes a group which may be cleaved from sulfur to yield a thiol group without destruction of the remainder of the molecule.

The terms "bioactive group" or "bioactive moiety", as used herein, denote a group which is capable of functioning as a metabolic substrate, catalyst, or inhibitor, or is capable of being preferentially taken up at a selected site of a subject, such as by possessing an affinity for a cellular recognition site.

The term "linking group", as used herein, denotes a group which, alone or together with one or more other groups, covalently bonds a bioactive group to the remainder of a compound of the formula Ia, Ib or Ic of the present invention.

The various substituents of the ligands of the present invention may be chosen to form stable compounds.

Compounds of the Formulae Ia, Ib and Ic

The compounds of the formulae Ia, Ib and Ic of the present invention may be prepared by methods such as those illustrated in, or analogous to, the following Reaction Schemes and in the Examples herein.

Reaction Scheme 1
Preparation of Compounds of the Formula Ia

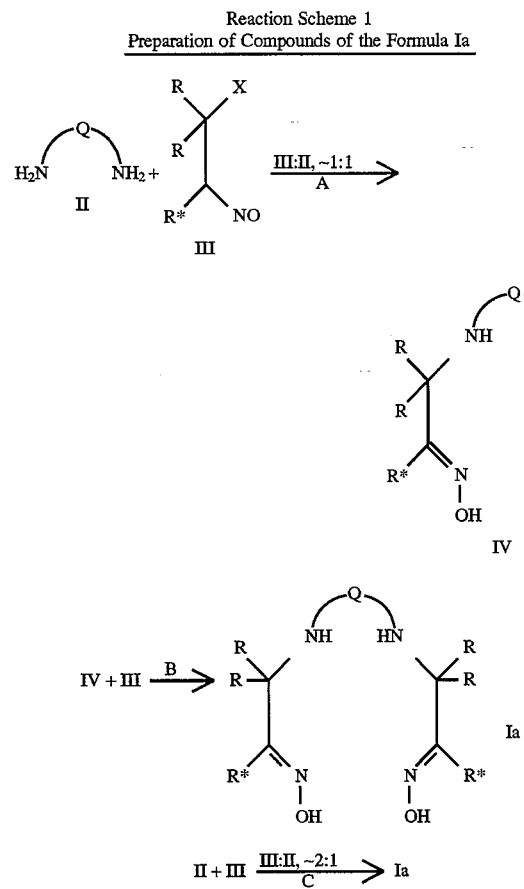

The above Reaction Scheme 1 illustrates methods for the preparation of compounds of the formula Ia.

According to Reaction Scheme 1, as shown in reaction A, a compound of the formula II may be contacted with an approximately equimolar amount of a compound of the formula III where X is halogen (preferably chloro), preferably in the presence of a tertiary amine such as diisopropylethylamine, to provide a compound of the formula IV. The compound of the formula IV may then be contacted with a compound of the formula III as shown in reaction B, also preferably in the presence of a tertiary amine such as diisopropylethylamine, to yield a compound of the formula Ia. Alternatively, as shown in reaction C, two or more molar equivalents of a compound of the formula III may be reacted with a compound of the formula II, preferably in the presence of a tertiary amine such as diisopropylethylamine, to directly yield a compound of the formula Ia. A solvent such as dimethylformamide or acetonitrile may be employed in the above reactions.

Conducting reaction C to obtain a compound of the formula Ia directly is particularly useful where the compound of the formula Ia is symmetric. Where the compound of the formula Ia is unsymmetric, use of reaction A followed by reaction B is preferred. In this latter case, different compounds of the formula III are employed in reactions A and B.

Compounds of the formula III may be prepared by methods such as those described in Vassian, *Inorg. Chem.*, 6, 2043–2046 (1967), U.S. patent application Ser. No. 08/054,120, filed Apr. 27, 1993 by Linder et al. (Attorney Docket No. RB90b) or, especially where R or R* is $CH_3$—, by the method of Nowotnik et al., European Patent No. 0179608 A2 (1986). Compounds of the formula II may be prepared by methods described in, or analogous to, the procedures of Boschman et al., *Eur. J. Med. Chem. Chimica Therapeutica*, 351–356 (1980); and Pankaskie et al., *Synthetic Communications*, 19, 339–344 (1989). (For the compounds of the formula III, the group —C(R*)—NO is also understood to denote the oxime group —C(R*)=N—OH with which it is in equilibrium, that is, X—C(RR)—C(R*)—NO<–>X—C(RR)—C(R*)=N—OH.)

Preferred compounds of the formula II are those of the following formulae IIa and IIb:

  (IIa)

  (IIb)

especially where m1 is two.

Compounds of the formula IIa may be prepared by internal dehydration of the compound:

  (V)

to form the compound:

  (VI)

and the cyclic amine so formed contacted with a hydrazine of the formula:

  (VII)

to yield a compound of the formula IIa.

Compounds of the formula IIb may be prepared by reaction of N-hydroxyphthalimide:

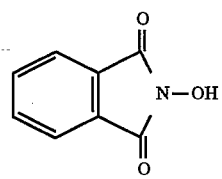

with a haloamine of the following formula:

  (VIII), where Pro is an amine protecting group such as tert-butoxycarbonyl (t-Boc or Boc), to yield a substituted phthalimide of the formula:

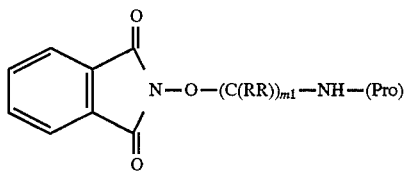

(IX)

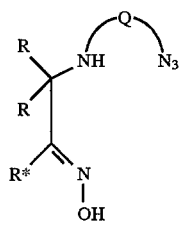

(IV$_{AZIDE}$)

The above substituted phthalimide may then be treated with hydrazine and deprotected to yield a compound of the formula IIb.

As the compounds of the formula II possess two terminal amino groups, it may be desirable to protect one of these groups to obtain preferential reaction through the unprotected amino group. Thus, compounds of the following formula II$_{Pro}$:

(II$_{Pro}$)

may be employed in place of compounds of the formula II in the above Reaction Scheme 1 (yielding, for example, compounds of the formula IV$_{Pro}$ which are compounds of the formula IV in which the group NH(Pro) is found in place of the NH$_2$ group, followed by deprotection for further reaction) where preferential reaction through one amino group is sought. For example, the above compound of the formula VI may be protected at the nitrogen, such as by use of di-t-butyl-dicarbonate, to yield the compound:

(VI$_{Pro}$)

The compound VI$_{Pro}$ may then be contacted with a compound of the formula VII to yield a compound of the following formula IIa$_{Pro}$:

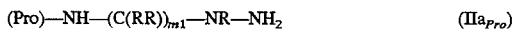

(Pro)—NH—(C(RR))$_{m1}$—NR—NH$_2$  (IIa$_{Pro}$)

and the latter employed as the compound of the formula II$_{Pro}$ as described above. In another example, the above compound of the formula IX may be contacted with hydrazine to yield a compound of the following formula IIb$_{Pro}$:

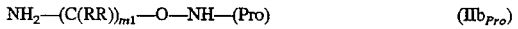

NH$_2$—(C(RR))$_{m1}$—O—NH—(Pro)  (IIb$_{Pro}$)

and the latter employed as the compound of the formula II$_{Pro}$ as described above. Where appropriate, compounds of the formula II$_{Pro}$ may also be employed in the other Reaction Schemes described herein.

Similarly, compounds of the following formula II$_{azide}$:

(II$_{AZIDE}$)

may also be employed in place of compounds of the formula II in the above Reaction Scheme 1, yielding compounds of the following formula IV$_{AZIDE}$:

upon reaction with a compound of the formula III, preferably in the presence of a tertiary amine such as diisopropylethylamine and a solvent such as dimethylformamide or acetonitrile. The azide group of the compound of the formula IV$_{AZIDE}$ so obtained may be reduced to an amine group NH$_2$, such as by contact with triphenylphosphine optionally followed by contact with an acid such as HCl, and further coupling with a compound of the formula III conducted to provide a compound of the formula Ia. Alternatively, for example, where reaction C is to be conducted to obtain a symmetric compound of the formula Ia, the azide group of the compound of the formula II$_{AZIDE}$ may be reduced as described above prior to coupling with a compound of the formula III to yield a diamine compound of the formula II which may be employed as described above in Reaction Scheme 1.

Compounds of the formula II$_{AZIDE}$ may be prepared by the methods of, or analogous to, those of Spencer Knapp, Jeffrey J. Hale, Margarita Bastos and Frank S. Gibson, *Tetrahedron Lett.*, 2109–2112 (1990); J. Cleophax, D. Anglesio, S. D. Gero and R. D. Guthrie, *Tetrahedron Lett.*, 1769 (1973); or the Examples herein.

Other preferred compounds of the formula II are those of the following formulae IIc, IId, IIe and IIf:

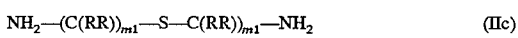
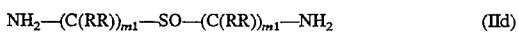
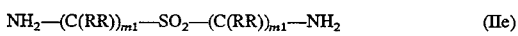
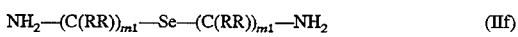

| | |
|---|---|
| NH$_2$—(C(RR))$_{m1}$—S—(C(RR))$_{m1}$—NH$_2$ | (IIc) |
| NH$_2$—(C(RR))$_{m1}$—SO—(C(RR))$_{m1}$—NH$_2$ | (IId) |
| NH$_2$—(C(RR))$_{m1}$—SO$_2$—(C(RR))$_{m1}$—NH$_2$ | (IIe) |
| NH$_2$—(C(RR))$_{m1}$—Se—(C(RR))$_{m1}$—NH$_2$ | (IIf) |

(where m2 is the same as m1), especially where R is hydrogen and m1 is $\geq 2$.

A compound of the formula IIc may be prepared by reacting sodium sulfide (Na$_2$S) with a bromoalkylphthalimide (commercially available) of the following formula:

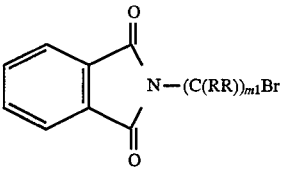

to afford a thiodialkylphthalimide of the following formula:

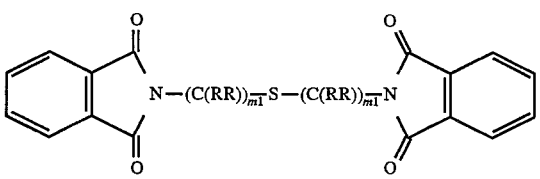

Treatment of the above thiodialkylphthalimide with hydrazine (NH$_2$NH$_2$) provides a compound of the formula IIc.

A compound of the formula IId may be prepared by oxidation of the above thiodialkylphthalimide with chromium trioxide ($CrO_3$) to afford the following sulfinyldialkylphthalimide:

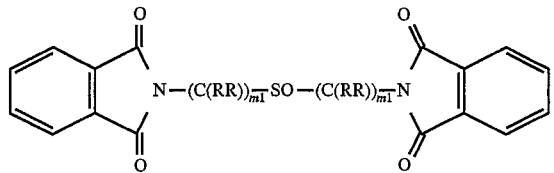

Treatment of the above sulfinyldialkylphthalimide with hydrazine ($NH_2NH_2$) provides a compound of the formula IId.

A compound of the formula IIe may be prepared by the hydrogen peroxide oxidation of the above thiodialkylphthalimide to afford the following sulfonyldialkylphthalimide:

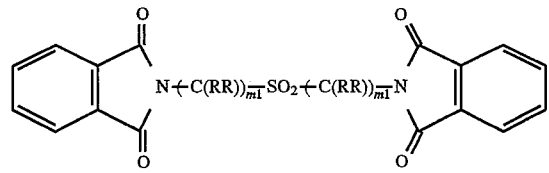

Deprotection of the phthalimido group by treatment with hydrazine ($NH_2NH_2$) provides a compound of the formula IIe.

A compound of the formula IIf may be prepared by contacting the above bromoalkylphthalimide with sodium selenide ($Na_2Se$) to afford the following selenodialkylphthalimide:

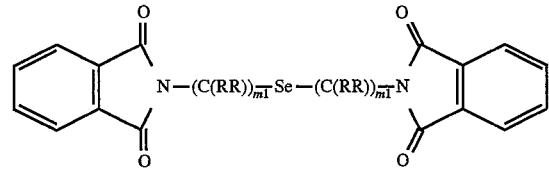

Treatment of the above selenodialkylphthalimide with hydrazine ($NH_2NH_2$) provides a compound of the formula IIf.

Reaction Scheme 2
Alternative Preparation of Compounds of the Formula Ia

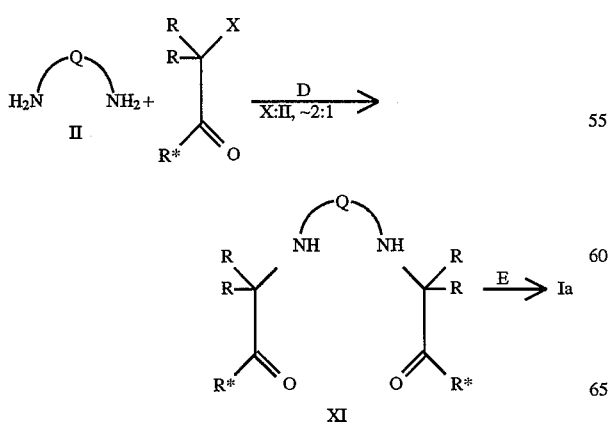

-continued
Reaction Scheme 2
Alternative Preparation of Compounds of the Formula Ia

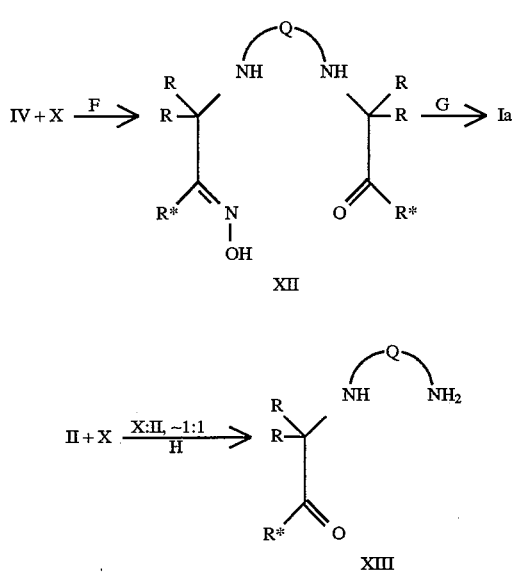

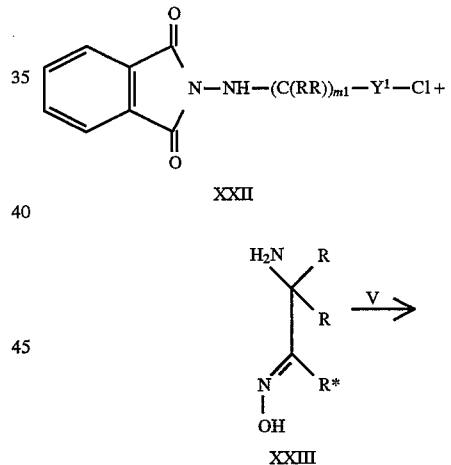

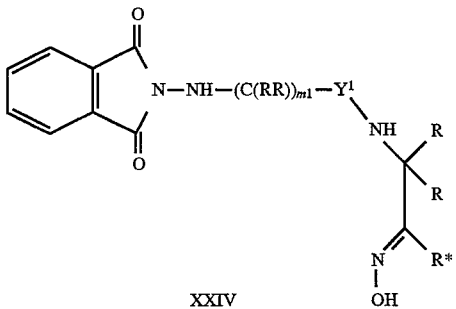

-continued
Reaction Scheme 2
Alternative Preparation of Compounds of the Formula Ia

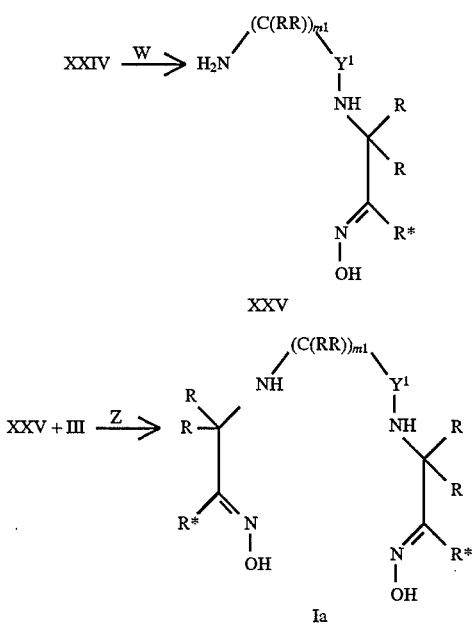

Alternative methods for the preparation of compounds of the formula Ia are shown in Reaction Scheme 2.

According to Reaction Scheme 2, in reaction D, a compound of the formula II may be contacted with approximately two or more molar equivalents of a haloketone X to form the diketone XI. A compound of the formula Ia may then be prepared, in reaction E, by conversion of the keto groups of the compound XI to oxime groups by methods such as treatment with O-trimethylsilyl hydroxylamine.

Alternatively, as shown in reaction F, a compound of the formula IV may be contacted with a haloketone X to form a compound of the formula XII. The keto group of the compound XII may be converted in reaction G to an oxime group by a method such as that described above for reaction E to form a compound of the formula Ia.

Another alternative method is that where, as shown in reaction H, compounds of the formulae II and X are contacted in an approximately equimolar ratio to form a monoketone of the formula XIII (or the corresponding compound XIII bearing a group $NH_{Pro}$ or $N_3$ in place of the group $NH_2$ when a compound $II_{Pro}$ or $II_{AZIDE}$, respectively, is employed as the starting material; followed by deprotection or reduction, respectively, for further reaction The latter compound, as shown in reaction J, may then be contacted with a compound of the formula X to yield a compound of the formula XI, and reaction E conducted to yield a compound of the formula Ia.

Performing reactions D and E sequentially is particularly useful where symmetric compounds of the formula Ia are sought. Unsymmetric compounds of the formula Ia may be prepared by sequentially conducting reactions F and G where the compounds IV and X contain different R or R* groups; or by sequentially conducting reactions H, J and E where different compounds of the formula X are employed in reactions H and J.

Compounds of the formula X may be obtained by methods such as those described by Pfleiderer et al., *Liebigs Ann. Chem.*, 99, 3008 (1966).

Compounds of the formula Ia may also be prepared starting with phthalimide compound XXII. As shown in reaction V, phthalimide compound XXIV may be prepared by contacting compound XXII with compound XXIII, followed by deprotection, such as with hydrazine, to form the compound XXV as shown in reaction W. Contacting compound XXV with compound III, as shown in reaction Z, provides a compound of the formula Ia. This reaction sequence is particularly preferred for compounds where the group $-(C(RR))_{m1}-$ is $-CH_2CH_2-$ and where $Y^1$ is $-SO_2-$.

Compounds of the formula XXIII may be obtained as described in Pfleiderer et al., *Liebigs Ann. Chem.*, 99, 3008 (1966). Compounds of the formula XXII may be obtained by methods analogous to the following method for the preparation of such compounds where $Y^1$ is $-SO_2-$, which may be obtained by contacting the compound:

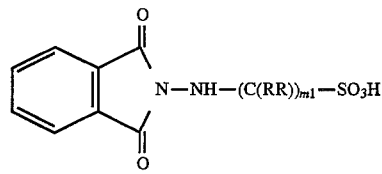

with thionyl chloride.

Reaction Scheme 3
Preparation of Compounds of the Formula Ib

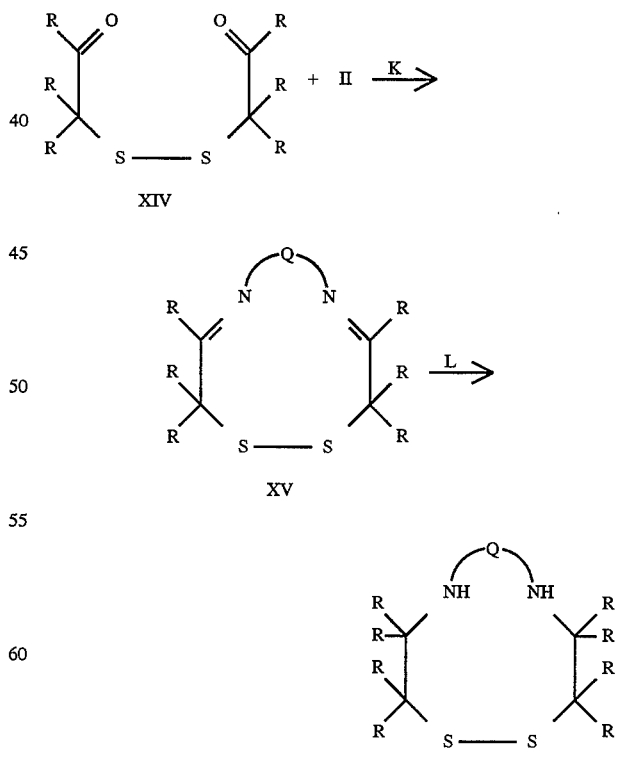

-continued
Reaction Scheme 3
Preparation of Compounds of the Formula Ib

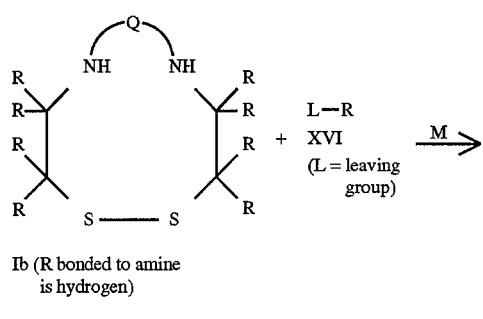

Ib (R bonded to amine is hydrogen)

L—R
XVI
(L = leaving group)

$\xrightarrow{M}$

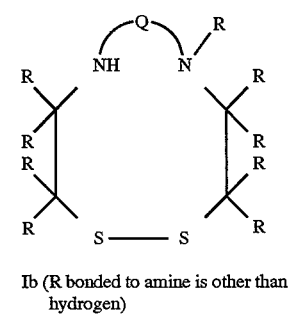

Ib (R bonded to amine is other than hydrogen)

Methods for the preparation of compounds of the formula Ib are shown in Reaction Scheme 3.

As shown in reaction K, a compound of the formula XIV (which may be prepared as described in Kung et al., *J. Nucl. Med.* 25, 326–332 (1984)) may be contacted with a compound of the formula II to provide a compound of the formula XV. The latter compound, as shown in reaction L, may be treated with a reducing agent, such as sodium borohydride, to provide a compound of the formula Ib.

Compounds of the formula Ib where the R group bonded to the amine is other than hydrogen, for example, where such R group is $—(A)_p-R^3$, may be obtained, as shown in reaction M, by coupling a compound of the formula Ib, where the corresponding R group is hydrogen, with a compound of the formula XVI, where L is a leaving group such as halogen. Compounds of the formula XVI are described in U.S. patent application Ser. No. 08/054,120, filed Apr. 27, 1993 by Linder et al. (Attorney Docket No. RB90b).

Reaction Scheme 4
Preparation of Compounds of the Formula Ic

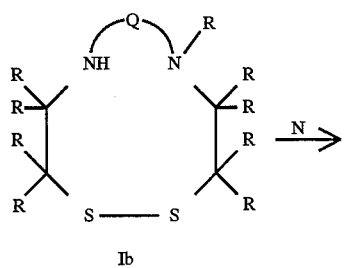

Ib $\xrightarrow{N}$

-continued
Reaction Scheme 4
Preparation of Compounds of the Formula Ic

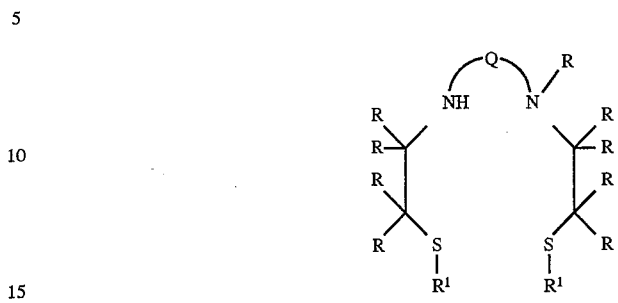

Ic  ($R^1 = H$)

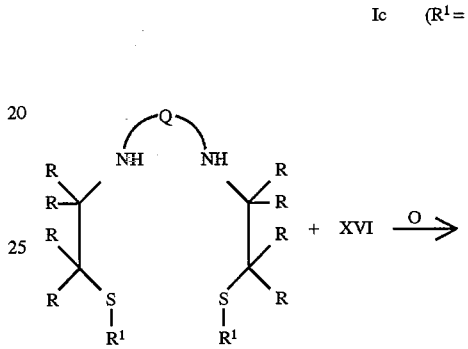

Ic  ($R^1 =$ thiol protecting group)

+ XVI $\xrightarrow{O}$

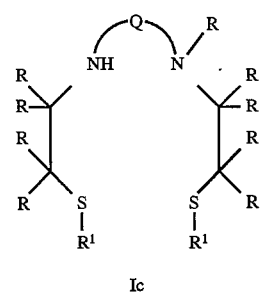

Ic

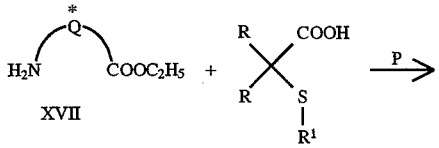

XVII

XVIII

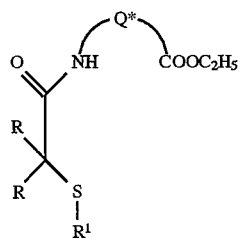

XIX

-continued
Reaction Scheme 4
Preparation of Compounds of the Formula Ic

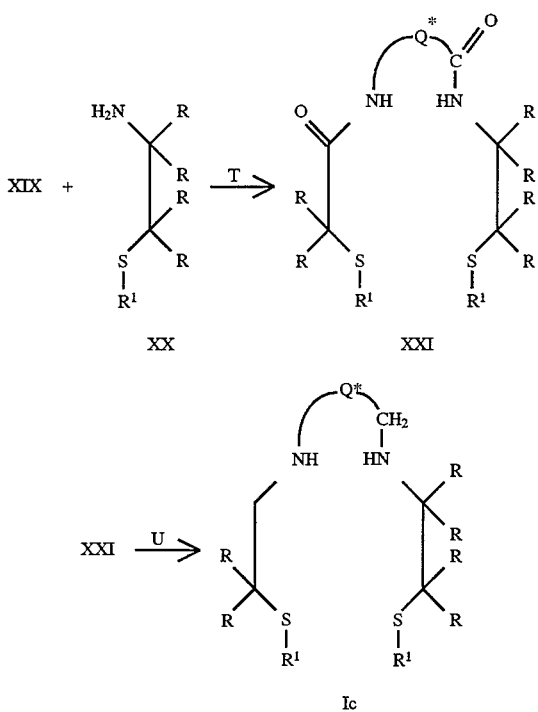

Methods for the preparation of compounds of the formula Ic are shown in Reaction Scheme 4.

Compounds of the formula Ic where $R^1$ is hydrogen may be prepared from compounds of the formula Ib, as shown in reaction N, by reducing the disulfide moiety to obtain the dithiol Ic using disulfide reducing agents such as tris(2-carboxyethyl)phosphine, dithiothreitol, and other such agents as disclosed in World Patent 89/10759.

As shown in reaction O, compounds of the formula Ic where the R group bonded to an amine is other than hydrogen may be prepared by coupling the corresponding compound where such R is hydrogen, in which $R^1$ is a thiol protecting group, with a compound of the formula XVI. The thiol protected starting material Ic may be obtained, for example, by adding thiol protecting groups to the corresponding compound of the formula Ic where $R^1$ is hydrogen by the use of standard thiol protecting groups such as are described in T. W. Green, *Protecting Groups in Organic Synthesis*, 193–217, John Wiley & Sons, N.Y. (1981). (Such thiol groups may be deprotected by methods including contact with technetium, or as described in Bryson, Dewan, James et al., *Inorg. Chem.*, 27, 2154–2161 (1988)).

The method described following for the preparation of compounds of the formula Ic is particularly useful for preparing unsymmetric such compounds. In this method, as shown in reaction P, compounds of the formulae XVII and XVIII are contacted under conditions suitable for peptide coupling to obtain a compound of the formula XIX. The term "Q*" denotes a group such that —Q*—$CH_2$— is Q. The compound of formula XIX is then contacted with a compound of the formula XX, as shown in reaction T, under conditions suitable for peptide coupling, to form a compound of formula XXI. In reaction U, the latter compound is reduced, for example, by treatment with borane, to yield the compound of formula Ic shown.

Compounds of the formula XVII are commercially available; or may be prepared by methods such as those analogous to the method for the preparation of the compound $H_2N$—O—$CH_2$—$COOC_2H_5$, which may be made by contacting the compound N-t-butoxycarbonyl hydroxylamine (Boc-HN—OH) with $BrCH_2COOC_2H_5$ in the presence of NaH in tetrahydrofuran, yielding the compound Boc—HN—O—$CH_2COOC_2H_5$, followed by deprotection of the Boc group with methanolic HCl. Compounds of the formula XVIII may be prepared by methods such as those described in Biniakiewiez et al., *J. Med. Chem.*, 35, 274–279 (1992). Compounds of the formula XX may be prepared by methods such as those described in Corbin et al., *Inorg. Chem.*, 23, 3404–3412 (1984).

In all of the above reactions described for preparing compounds of this invention, groups such as sulfur groups, amine groups and ketone groups may be protected where appropriate during the various reactions, and the so-protected resulting products thereafter deprotected by known techniques. Salts (formed as appropriate with inorganic and/or organic acids and/or bases, preferably pharmaceutically acceptable acids and/or bases) and/or solvates (such as hydrates) of reactants or products may be employed or prepared as appropriate in any of the methods for the preparation of the compounds of the present invention (including complexes). Throughout this specification, it is understood, unless indicated otherwise, that the formulae Ia, Ib and Ic and complexes thereof include such salts and solvates.

Preferred Compounds

Compounds of the formula Ia are preferred in the present invention, particularly compounds of the following formulae Ia' or Ia":

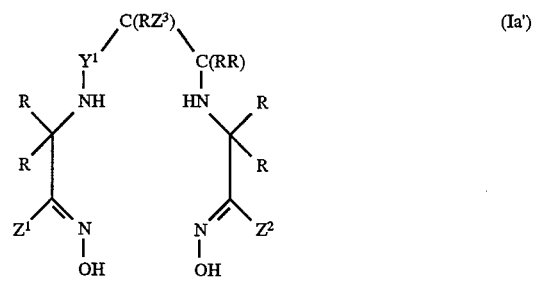
(Ia')

where $Z^1$ and $Z^2$ are R* groups and $Z^3$ is an R group, and further where one, two or all three of $Z^1$, $Z^2$ and $Z^3$ are —$(A)_p$-$R^3$ groups; or

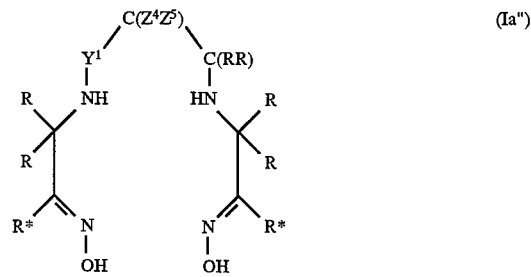
(Ia")

where $Z^4$ and $Z^5$ are independently selected from hydrogen, halogen (especially fluoro), alkyl (especially unsubstituted alkyl, such as methyl, or hydroxyalkyl, such as hydroxymethyl), aryl, or carboxyl.

Preferred linking groups, and preferred $R^3$ groups, are described below.

$Y^1$ is preferably —NR— or, especially, —O—. R or R* groups which are not —$(A)_p$-$R^3$ are preferably hydrogen or alkyl groups, especially unsubstituted lower alkyl groups such as methyl, ethyl or n-butyl or alkoxyalkyl groups such as ethoxymethyl.

Metal Complexes

The compounds of the formulae Ia, Ib and Ic may be employed as ligands for the formation of metal complexes. In this regard, the disulfide of a compound of the formula Ib is preferably reduced to the corresponding dithiol Ic prior to formation of a metal complex.

The metal complexes of the present invention may be formed by complexing a compound Ia, Ib or Ic with a radioactive or non-radioactive metal, including metals having an atomic number 22–31, 39–49 or 73–82, especially rhenium or technetium, preferably under basic conditions.

An exemplary method for the formation of a metal complex of the present invention is that where a complex or salt of the desired metal in the desired oxidation state and containing one or more easily displaceable (i.e. labile) ligands (for example, $H_2O$, halogen (eq. Cl), $NO_3^-$, or sugars) is mixed with ligand(s) of the present invention at a pH value suitable for forming the desired complex. The labile ligand is displaced from the metal by the ligand(s) of the present invention to form a metal complex of the present invention.

Illustrative such methods are shown following:

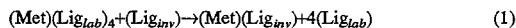

(1)

where

Met is a metal in a desired oxidation state;

$Lig_{lab}$ is a labile ligand such as $H_2O$, $Cl^-$, $Br^-$, $F^-$ or $NO_3^-$; and $Lig_{inv}$ is a ligand of the present invention.

(2)

(3)

where $Lig_{mono}$ is a monodentate ligand such as pyridine, halide, phosphine or amine.

(4)

or

(5)

where $Lig_{bi}$ is a bidentate ligand such as a sugar, a diol, a bisamine, bipyridine or phosphine, and where, for each equation (1) to (5) above, the appropriate charge balance is employed.

Alternatively, the metal complexes of the present invention may be prepared from a metal in an oxidation state different from that of the desired complex. An exemplary such method is that where either a reducing agent or an oxidizing agent (depending on the oxidation state of the metal used, and the oxidation state of the desired final product) is added to the reaction mixture containing metal to bring the metal to the desired oxidation state. The oxidant or reductant may be used to form an intermediate complex in the desired oxidation state but with labile ligands which are then displaced by a desired chelating ligand of the present invention; or the oxidant or reductant may be added to the reaction mixture containing metal along with the desired ligand to achieve the change to the desired oxidation state and chelation to the desired metal in a single step.

Exemplary metal complexes of the present invention may be shown as the following formulae $Ia_{complex}$ and $Ic_{complex}$:

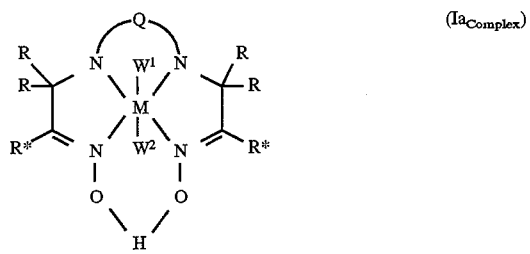

(Ia$_{Complex}$)

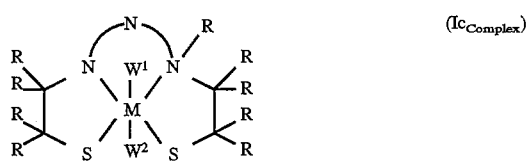

(Ic$_{Complex}$)

where the R and R* groups are as defined above, and where M can be a radioactive or non-radioactive metal which may optionally have other ligand(s) $W^1$ and/or $W^2$ in the unfilled coordination sites thereof. Radioactive metals are preferred in these complexes, for example, technetium or rhenium for the complexes of $Ic_{Complex}$ and technetium for the complexes of $Ia_{Complex}$. Preferably, in the cases where M is rhenium or technetium, the

portion can be shown as

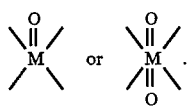

Other suitable co-ligands $W_1$ and $W_2$ to form these complexes may include, but are not limited to, mono-, di-, or tridentate ligands which, when combined with the ligands Ia, Ib or Ic, form neutral metal complexes, particularly of technetium or rhenium, with the metal preferably in the +5 oxidation state.

The metal complexes of the present invention find utility as diagnostic and/or therapeutic agents. Thus, the present invention provides methods for the diagnosis of the presence and/or status of a disease state, or for the treatment of a disease state, comprising the step of administering a metal complex of the present invention to a subject in need thereof. The metal complexes of the present invention may be administered by any appropriate route such as orally, parenterally (for example, intravenously, intraperitoneally, intramuscuiarly, or subcutaneously), or by any other suitable method. For example, the complexes of this invention may be administered to a subject by bolus or slow infusion intravenous injection.

The amount administered may be selected based on the desired use, such as to produce a diagnostic image of an organ or other site of a subject or a desired radiotherapeutic effect, by methods known in the art. Exemplary dosages are those employing about 30–200 mCi rhenium (for radiotherapy) or about 10–60 mCi technetium (for imaging). The "subject" of the methods of the present invention is preferably a mammal such as a domestic mammal, for example, a dog, cat, horse or the like, or most preferably, a human. Depending upon the metal and ligand used, the complexes of the present invention may be employed as, for example, imaging agents useful for imaging organs such as the heart, brain (where the complex may cross the blood-brain barrier), or the hepatobiliary system. They are especially useful for the imaging of hypoxic tissue, and as therapeutic agents, especially as hypoxic tissue cytotoxins, or radiosensitizers.

Cell permeability is a property of a cell membrane which describes the mobility of extraneous molecules (permeants) within the internal structure of the membrane (Stein, "Transport and Diffusion Across Cell Membrane", New York Academic Press Inc. (1986); Kotyk et al., *Biophysical Chemistry of Membrane Functions*, Chichester, UK: John Wiley & Sons (1988)). Molecules to which the membrane is permeable are able to penetrate through the membrane to reach the environment on the opposite side. Metal complexes which have a permeability through cell membranes greater than that of $^{14}$C-sucrose, particularly those containing a hypoxia-localizing moiety as discussed below, are preferred in the diagnostic or therapeutic methods of the present invention. Cell permeability may be determined by methods such as those described in U.S. patent application Ser. No. 08/054,120, filed Apr. 27, 1993 by Linder et al. (Attorney Docket No. RB90b), incorporated herein by reference.

Preferred complexes of the present invention are those comprising a compound of the formula Ia, Ib or Ic complexed with a radionuclide such as technetium or rhenium.

Rhenium is particularly useful as a radiotherapy agent. The rhenium employed is preferably one of the radionuclides Re-186 or Re-188, or a mixture thereof, which mixture may also include Re-185 and/or Re-187. Preparation of the complexes of the present invention where the metal is rhenium may be accomplished using rhenium in the +5 or +7 oxidation state. Examples of compounds in which rhenium is in the Re(VII) state are NH$_4$ReO$_4$ or KReO$_4$. Re(V) is available as, for example, [ReOCl$_4$](NBu$_4$), [ReOCl$_4$](AsPh$_4$), ReOCl$_3$(PPh$_3$)$_2$ and as ReO$_2$(pyridine)$_4$$^+$. (Ph is phenyl; Bu is n-butyl). Other rhenium reagents capable of forming a rhenium complex may also be used. The use of "carrier rhenium" is preferred. The phrase "carrier rhenium" means that the rhenium compounds used contain non-radioactive rhenium at concentrations >10$^{-7}$M.

Technetium is particularly useful as a diagnostic imaging agent. The technetium employed is preferably one or more of the radionuclides Tc-99m, Tc-94m or Tc-96. The preferred radioisotope for medical imaging is $^{99m}$Tc. Its 140 keV γ-photon is ideal for use with widely-available gamma cameras. It has a short (6 hour) half life, which is desirable when considering patient dosimetry. $^{99m}$Tc is readily available at relatively low cost through commercially-produced $^{99}$Mo/$^{99m}$Tc generator systems. Preparation of the complexes of this invention where the metal is technetium may be accomplished using technetium in the form of the pertechnetate ion. For Tc-99m, the pertechnetate ion is preferably obtained from commercially available technetium-99m parent-daughter generators; such technetium is in the +7 oxidation state. The generation of the pertechnetate ion using this type of generator is well known in the art, and is described in more detail in U.S. Pat. Nos. 3,369,121 and 3,920,995. These generators may generally be eluted with saline solution, and the pertechnetate ion obtained as the sodium salt. Pertechnetate may also be prepared from cyclotron-produced radioactive technetium using procedures well known in the art.

The formation of a technetium complex is preferably achieved by mixing pertechnetate ion in normal saline with the appropriate ligand, preferably a ligand containing at least one R group which is the group —(A)p—R$^3$ where (A)p is a linking group and R$^3$ is a hypoxia-localizing moiety. An appropriate buffer or physiologically acceptable acid or base may be used to adjust the pH to a value suitable for labeling the ligand. This appropriate value of pH will vary depending upon the nature of the ligand; for example, for ligands of the formula Ia, a pH in the range between ~5.5 to ~9.5 is suitable, preferably a pH value in the range of 7.0 to 8.5. For ligands of the formula Ic, a pH value in the range 3 to 8 is suitable, preferably a pH of ~6.0. A source of reducing agent may then be added to bring the pertechnetate down to the oxidation state of Tc(V) for chelation with the ligand. Stannous ion is the preferred reducing agent, and may be introduced in the form of a stannous salt such as stannous chloride, stannous fluoride, stannous tartrate, stannous diethylenetriamine pentaacetic acid (stannous DTPA), or stannous citrate, or the like. The reaction is preferably run in an aqueous or aqueous/alcohol mixture, at or about room temperature, using a reaction time of about 1 minute to about 1 hour. The reducing agent is preferably present at a concentration of 5 to 50 µg/mL. The ligand is preferably present in a concentration of 0.5 to 2 mg/mL. Optionally, co-ligands W$_1$ and W$_2$ discussed above may be added.

Alternatively, the technetium complexes of this invention may be prepared by ligand exchange. A labile Tc(V) complex may be prepared by the reduction of TcO$_4$$^-$ in the presence of a ligand which forms a labile technetium complex, such as ethylene glycol, mannitol, or the hydroxycarboxylate ligands glucoheptonate, gluconate, citrate, malate or tartrate, am a pH value which is appropriate for the exchange ligand employed (usually 5 to 8). A reducing agent, such as the stannous salts described above, may be added, causing the formation of a labile reduced complex of Tc with the exchange ligand. This reduced Tc complex is then mixed with the ligand ultimately desired, preferably one containing one or more —(A)p-R$^3$ groups, at an appropriate pH value (as described above). The labile exchange ligand is displaced from the metal by the desired ligand, thus forming the technetium complexes of this invention.

Metal complexes of the present invention are preferred in which a compound described above under the section entitled "Preferred Compounds", such as a compound of the formula Ia' or Ia", is complexed with a metal, most preferably, with rhenium or technetium. Ligands which form single, neutral complexes are preferred. Additionally, complexes of the present invention containing one or more bioactive groups R$^3$ (especially hypoxia-localizing moieties) described further as follows are especially preferred. Exemplary complexes include those having the following structures:

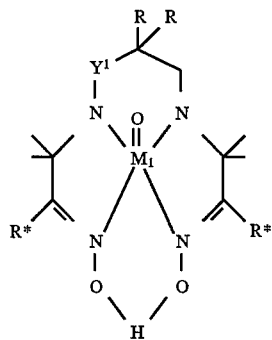

and

-continued

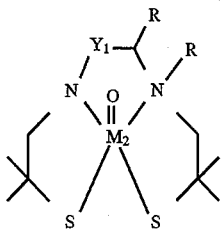

where $M_1$ is technetium and $M_2$ is technetium or rhenium and wherein at least one R or R* group is —$(A)_p$-$R^3$.

While metal complexes of the present invention containing one or more bioactive groups as described below are preferred, those complexes of the present invention lacking such groups are useful, for example, in flow or organ imaging. Preferred such complexes lacking bioactive group (s) are those containing lipophilic ligands suitable for imaging the heart, brain or hepatobiliary system.

Bioactive Groups

A bioactive group of the compounds of the present invention is capable of functioning as a metabolic substrate, catalyst or inhibitor, for example, to aid in clearance of the complex from non-target tissue; or is capable of being preferentially taken up at a selected site of a subject, such as by possessing an affinity for a cellular recognition site such as a receptor, enzyme, or transport mechanism, or by containing reactive groups for coupling to proteins, or tissue localization by another biochemical process. Thus, complexes of the present invention are contemplated where one or more bioactive groups are bound to the remainder of the complex which retain their desired bioactivity when so bound.

Exemplary bioactive groups include amphetamines, barbiturates, sulfonamides, monoamine oxidase substrates and inhibitors, hormones, enzymes, lipids, ligands for cell membrane receptors, antihypertensives, neurotransmitters, amino acids and oligopeptides, radiosensitizers, steroids (such as estrogen or estradiol), monoclonal or polyclonal antibodies or fragments thereof, sugars (such as glucose derivatives), fatty acids, substrates for muscarinic receptors (such as 3-quinuclidinyl benzilate), substrates for dopamine receptors (such as spiperone), biotin, chemotactic peptides, substrates for benzodiazepine receptors and, especially, hypoxia-localizing moieties described further below.

Complexes of the present invention containing bioactive groups are useful in that they employ properties, e.g., receptor binding, metabolism, etc., of a particular biochemically active group to provide imaging or treatment of a particular site or function. Preferred complexes of the present invention, especially where the metal is $^{99m}$Tc, provide highly effective, relatively easy to use diagnostic imaging products which are characterized by a covalent bond between the radionuclide complex and the bioactive group while substantially retaining the uptake properties of the free bioactive group. Examples of diagnostic uses for the complexes of the present invention include, but are not limited to, imaging of hypoxic tissue, e.g., in the heart, brain, lungs or in tumors, preferably where the bioactive group is a nitro-heterocyclic group trapped by hypoxia-mediated reduction of the nitro moiety (referred to herein as a "hypoxia-mediated nitro-heterocyclic group"), discussed further below; imaging of the brain and lungs when the bioactive group is a lipophilic amine-containing compound, e.g. an amphetamine; imaging of the brain, heart or tumors when the bioactive group is a sugar (e.g., a glucose derivative); imaging of the heart when the bioactive group is a fatty acid; imaging of steroid receptor sites when the bioactive group is asteroid (e.g., an estrogen for imaging breast carcinoma); and imaging of sites of infection when the bioactive group is a chemotactic peptide with affinity for blood cell types which localize at the site of infection.

In addition to diagnostic agents, the present invention also provides stably bound complexes for radiotherapeutic indications, especially where the metal is Re, such as those indications described in U.S. Pat. No. 4,871,836. For example, Re complexes of the present invention which include estradiols can be used in the treatment of breast carcinoma. Also, to the extent that hypoxic tissue is known to be present in tumors, Re complexes of the present invention where the bioactive group is a hypoxia-localizing moiety are suitable for radiotherapy. The complexes of this invention where the metal is Re, for use in radiotherapy, are preferably injected into humans and allowed to concentrate at the desired site. Targeting of the radionuclide to a desired site with great specificity may thus be achieved. Radiotherapy is contemplated for those areas where a sufficient quantity of interacting sites (for example, estrogen receptors or hypoxic tissue) are present so as to provide therapeutic levels of the radionuclide to the area needing treatment.

When the bioactive group $R^3$ is a steroid, it is understood that either a steroid, a substituted steroid derivative or a non-steroidal derivative may be employed provided that the $R^3$ group chosen has an affinity for the steroid receptor. For example, $R^3$ may be the steroid estradiol:

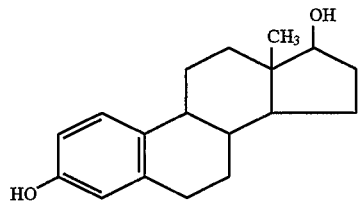

The estradiol group may be bonded to the remainder of the complex at any available position on the molecule, but is preferably bonded through a linking group to either an atom in the B ring or an atom in the D ring. Additionally, the estradiol molecule may be substituted at available positions by one or more R groups where R is as defined above. Alternatively, the steroid molecule may be replaced by a non-steroidal diol with a known affinity for the estrogen receptor, such as

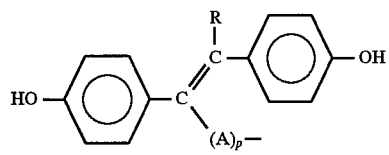

where $(A_p)$ and R are as defined above.

When the bioactive group is a substrate for a muscarinic receptor, the —$(A)_p$-$R^3$ portion of the complex is preferably the group:

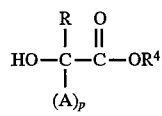

where $(A)_p$ and R are as defined above and $R^4$ is a tertiary or quaternary amine, such as 3-quinuclidinol or a substituted 3-quinuclidinol, or the following compounds:

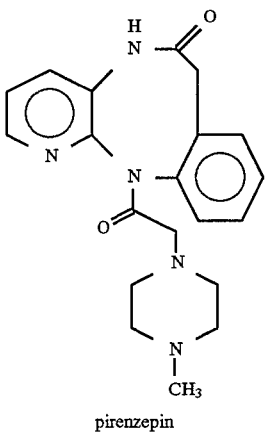

pirenzepin or

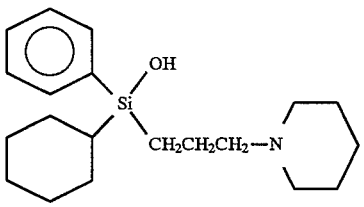

4-HHSD

Linking Groups

The linking group(s) (A)p of the compounds of the present invention, when present (that is, when p is greater than zero), may be any one or more moieties which can serve to physically distance, or otherwise isolate, the bioactive group from the remainder of the compound of the formula Ia, Ib or Ic or complex thereof. The presence of such linking group(s) may be desirable, for example, where a bioactive group, such as a hypoxia-localizing moiety, may be inhibited in its action by the remainder of the complex. In considering the various linking groups which may be employed, it is understood that p may be any convenient value depending upon the design choice for the desired complex. Preferably, p is ≦20 and is most preferably ≦10.

Preferred linking groups which may be employed alone (where p is one), or together to form a straight or branched chain (where p is greater than one) and which may be bonded to the remainder of the ligand from either end are: —CH$_2$—, —CHR$^5$—, —CR$^5$R$^6$—, —CH=CH—, —CH=CR$^5$—, —CR$^5$=CR$^6$—, —C≡C—, cycloalkyl, cycloalkenyl, aryl (e.g., p-phenylene or hydroxy substituted p-phenylene), heterocyclo, oxygen, sulfur, —C(O)—, —NH—, —HC=N—, —CR$^5$=N—, —NR$^5$—, or —CS—; wherein R$^5$ and R$^6$ are independently selected from alkyl, alkenyl, alkoxy, aryl, 5- or 6-membered nitrogen- or oxygen-containing heterocycles, halogen, hydroxy or hydroxyalkyl.

In the complexes of the present invention, the preferred values for (A)p (bonded to the remainder of the ligand from either end) are alkyl, oxa-alkyl, hydroxyalkyl, hydroxyalkoxy, alkenyl, arylalkyl, arylalkylamide, alkylamide, alkylamine and (alkylamine)alkyl.

The most preferred values for (A)p are selected from the following (bonded to the remainder of the ligand from either end): —(CH$_2$)$_{1-5}$— (especially methyl or ethyl, particularly when bonded to a hypoxia-localizing moiety), —CH$_2$—CH=CH—CH$_2$—, —(CH$_2$)$_{1-2}$—C(O)—NH—(CH$_2$)$_{1-3}$—, —C$_6$H$_5$—(CH$_2$)$_{1-2}$—, —(CH$_2$)$_{1-2}$—CH(OH)—CH$_2$—, —(CH$_2$)$_2$—O—, —CH$_2$CH(OH)CH$_2$OCH$_2$—, —CH$_2$—C(O)—NH—CH—C$_6$H$_5$—, —(A'—O—A")$_{1-3}$, and —(A'—NH—A")$_{1-3}$; where A' and A" are the same or different alkyl or aryl groups and C$_6$H$_5$ is p-phenylene.

Hypoxia-Localizing Moieties

Many procedures presently conducted in the field of nuclear medicine involve radiopharmaceuticals which provide diagnostic images of blood flow (perfusion) in the major organs and in tumors. The initial regional uptake of these radiopharmaceuticals within the organ of interest is proportional to flow; high flow regions will display the highest concentration of radiopharmaceutical, while regions of little or no flow have relatively low concentrations. While diagnostic images showing these regional differences are useful in identifying areas of poor perfusion, metabolic information of the state of the tissue within the region of apparently low perfusion is also sought. The present complexes containing one or more groups —(A)$_p$—R$^3$ where R$^3$ is a hypoxia-localizing moiety specifically localize in hypoxic tissue, that is, tissue which is deficient in oxygen but still viable, and thus can provide added information on the state of the tissue.

Suitable hypoxia-localizing moieties are those which are preferentially retained in regions of a subject which are hypoxic relative to the degree of retention in regions which are normoxic. The greater the selective localization in hypoxic versus normoxic tissue, the more accurate the information provided. A radiopharmaceutical with these properties will display relatively high concentrations in such hypoxic regions, with low concentrations in normoxic and infarcted regions. Complexes of the present invention which concentrate rapidly in hypoxic tissue and which remain stably bound in such tissue over time, while exhibiting a lack of binding and rapid washout from normoxic tissue, are preferred.

Exemplary diagnostic uses for such complexes of the present invention, especially where the metal complexed is technetium, include imaging of hypoxic tissue present under pathological conditions in areas such as the heart, brain, lungs, liver, kidneys or in tumors, or in peripheral vascular diseases such as diabetes. In the brain or heart, hypoxia typically follows ischemic episodes produced by, for example, arterial occlusions or by a combination of increased demand and insufficient flow. Diagnostic imaging with radiopharmaceuticals of the present invention possessing hypoxia-localizing moieties allows the identification of tissue which is at risk of progressing to infarction, but still salvagable in such areas.

Additionally, tumors often have regions within their mass which are hypoxic. These result when the rapid growth of the tumor is not matched by the extension of tumor vasculature. The radiopharmaceuticals of the present invention which localize preferentially within regions of hypoxia may also therefore be used to provide images which are useful in the diagnosis and management of therapy of tumors. Further, a compound which localizes within the hypoxic region of tumors, and which is labeled with a radionuclide with suitable α- or β-emissions, may be used for the internal radiotherapy of tumors. Stably bound complexes where Re is the radiometal complexed are particularly useful for radiotherapeutic indications where hypoxic tissue is known to be present in tumors.

While the precise mechanism for retention of hypoxia-localizing compounds is not known, it is believed that these compounds, for example, nitroheteroaromatics such as misonidazole, undergo intracellular enzymatic reduction. This process is believed to be reversible in cells with a normal oxygen partial pressure, but in cells which are deficient in oxygen, further reduction can take place. This leads to the formation of reactive species which bind to or are trapped as intracellular components, providing for preferential entrapment in hypoxic cells. It is therefore desirable for compounds used for hypoxia imaging and treatment to be able to traverse cell membranes, and to be capable of being reduced, for example, by reductases such as xanthine oxidase.

Any moiety which is preferentially taken up and/or retained by hypoxic tissue relative to normoxic tissue, and which is capable of being bound to the remainder of a compound of the formulae Ia, Ib or Ic, may be employed as the hypoxia-localizing group of the present invention.

Exemplary such groups include hypoxia-mediated nitroheterocyclic compounds, such as nitroheterocyclic groups which may be trapped by hypoxia-mediated reduction of the nitro moiety, for example, nitroimidazoles and derivatives thereof. Various nitroheterocyclic (and nitrocarbocyclic) moieties are described in the following documents, incorporated herein by reference, and are suitable for use in the complexes of the present invention by connection to a compound of the formula Ia, Ib or Ic directly or through a linking group (various linking groups also being described therein): Koh et al., "Hypoxia Imaging of Tumors Using [F-18]Fluoronitroimidazole", *J. Nucl. Med.*, Vol. 30, 789 (1989); Koh et al., "Correlation of Kinetic Parameters of Nitroreductase Enzymes with Redox Properties of Nitroaromatic Compounds", *J. Biol. Chem.*, Vol. 264, 21, 12379–12383 (1989) (especially Table 1 on p. 12380); Hoffman et al., "Binding of the Hypoxic Tracer [H-3] Misonidazole in Cerebral Ischemia", Stroke, Vol. 18, 168 (1987); Kedderis et al., "The Metabolic Activation of Nitro-Heterocyclic Therapeutic Agents", *Drug Metabolism Reviews*, 19(1), p. 33–62 (1988); Adams et al., "Hypoxia Mediated Nitro-Heterocyclic Drugs in the Radio- and Chemotherapy of Cancer", *Biochem. Pharmacology*, Vol. 35, No. 1, pages 71–76 (1986); Brown et al., "Structure-Activity Relationships of 1-Substituted 2-Nitroimidazoles: Effect of Partition Coefficient and Sidechain Hydroxyl Groups on Radiosensitization In vitro", Rad. Research, 90, 98–108 (1982); Adams et al., "Structure-Activity Relationships in the Development of Hypoxic Cell Radiosensitizers", *Int. J. Radiat. Biol.*, Vol. 35, No. 2, 133–150 (1979); and Adams et al., "Structure-Activity Relationships in the Development of Hypoxic Cell Radiosensitizers", *Int. J. Radiat. Biol.*, Vol. 38, No. 6, 613–626 (1980).

When the hypoxia-localizing group is a hypoxia-mediated nitro-heterocyclic group, the linker/localizing group portion of the complex may be represented by the following structures:

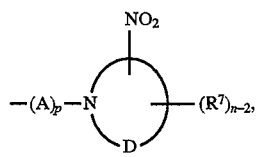

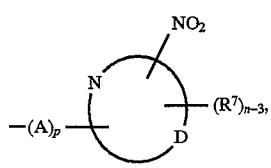

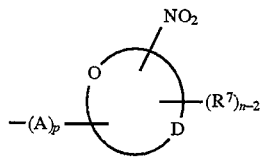

where

D is a grouping of atoms forming, together with the nitrogen or oxygen atom to which it is bonded, a 5- or 6-membered ring;

n is the total number of substitution positions available on the 5- or 6-membered ring; and the one or more $R^7$ substituents are independently selected from hydrogen, halogen (especially fluoro), hydroxy, alkyl, aryl, alkoxy, hydroxyalkyl, hydroxyalkoxy, alkenyl, arylalkyl, arylalkylamide, alkylamide, alkylamine, acyl, alkoxycarbonyl and (alkylamine)alkyl.

Preferably, the grouping of atoms D contains one or more of the following: nitrogen, oxygen, sulfur, —$CR^5$—, —$CR^7$=, —$CR^7R^7$— or —CRR—. When $(A)_p$ is absent (i.e., p=0) the nitro-heterocyclic hypoxia-localizing moiety is linked to the rest of the complex via a nitrogen or carbon atom of the ring. The group (A)p may be selected not only according to its capacity to distance the hypoxia-localizing moiety from the rest of the complex, but also in accordance with its effect on the reduction potential of the hypoxia-mediated nitro-heterocyclic group.

Preferred hypoxia-localizing moieties (shown with the linking groups) are 2-, 4- and 5-nitroimidazoles, such as

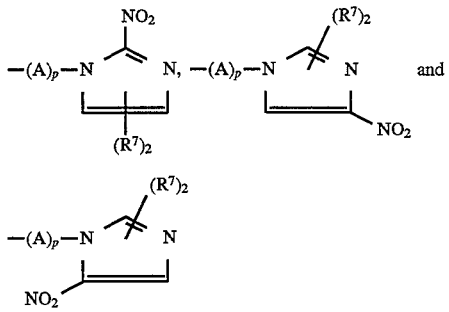

nitrofuran and nitrothiazole derivatives, such as

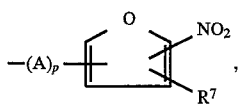

especially 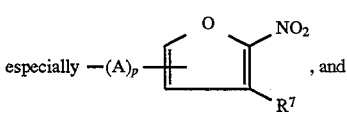, and

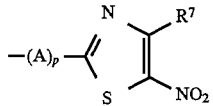

and nitrotriazoles, such as

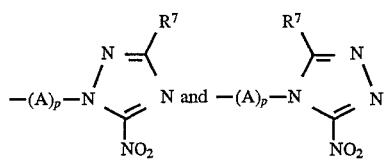

Exemplary groups (including (A)p linking groups) include, but are not limited to,

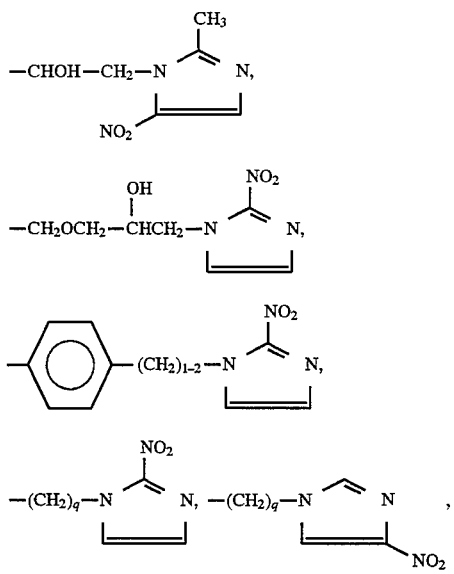

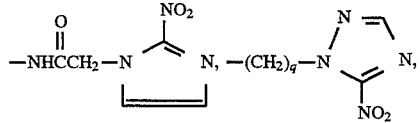

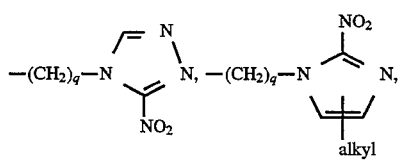

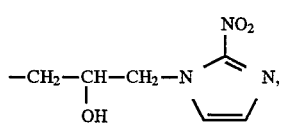

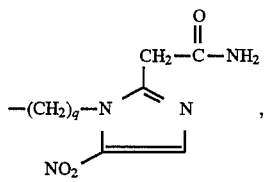

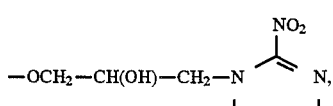

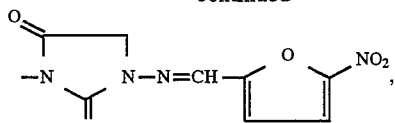

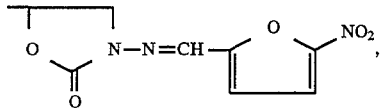

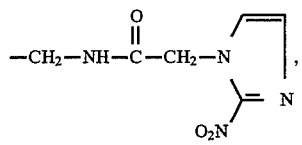

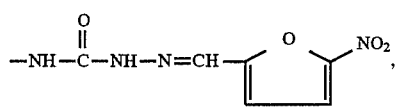

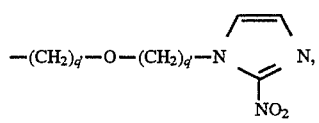

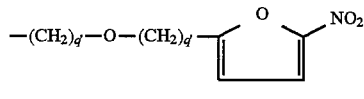

and

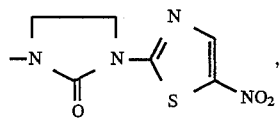

where q=0 to 10 and each q' is independently 1 to 3.

Such complexes of the present invention are useful in that they utilize the properties of the hypoxia-localizing group to provide imaging or treatment of hypoxic tissue at a particular site. Preferred complexes are those where the hypoxia localizing moiety is a hypoxia-mediated nitro-heterocyclic group, such as nitroimidazoles or nitrofurans and derivatives thereof. Most preferred are those where the hypoxia-localizing moiety is 2-nitro-imidazole or a derivative thereof.

In addition to being useful in imaging hypoxic tissue, the present complexes may also be used as blood flow markers, that is, for perfusion imaging. The initial distribution of the novel complexes may be proportional to blood flow and therefore imaging carried out soon after administration may be used as an indicator of perfusion. A short time later, as the complexes wash out of the normoxic tissue but are retained in the hypoxic tissue, imaging of the hypoxic tissue is realized.

Kits for Forming Metal Complexes

It is convenient to prepare the complexes of the present invention at, or near, the site where they are to be used. A single, or multi-vial kit that contains all of the components needed to prepare the complexes of this invention, other than the radionuclide ion itself, is an integral part of this invention.

A preferred single-vial kit of the present invention comprises a ligand of the formula Ia, Ib or Ic, and a source of a pharmaceutically acceptable reducing agent such as a stannous salt. Most preferably, in addition, the kit is buffered with a pharmaceutically acceptable acid or base to adjust the pH to a desired value for complex formation as described above. It is preferred that the kit contents be in lyophilized form. Such a single vial kit may optionally contain exchange ligands such as glucoheptonate, gluconate, mannitol, malate, citric or tartaric acid and may also contain reaction modifiers, such as diethylenetriaminepentaacetic acid or ethylenediamine tetraacetic acid. Additional additives, such as solubilizers (for example α-, β- or γ-cyclodextrin), antioxidants (for example ascorbic acid), fillers (for example, NaCl) may be employed to improve the radiochemical purity and stability of the final product, or to aid in the production of the kit.

Single vial kits may be prepared where the components are included in two or more lyophilized layers according to U.S. patent application Ser. No. 08/168,100 by Nowotnik, entitled "Multilayer Lyophile" filed Dec. 14, 1993 (Attorney Docket No. TU39), incorporated by reference herein in its entirety.

A preferred multi-vial kit of the present invention comprises, in one vial, the components, other than the radionuclide itself, required to form a labile radionuclide (especially Tc(V)) complex as described above, that is, an exchange ligand and a pharmaceutically acceptable reducing agent such as a stannous salt. The quantity and type of exchange ligand, and amount and type of reducing agent and buffer used may be selected based on the nature of the exchange complex to be formed. The ligand Ia, Ib or Ic of the present invention is contained in a second vial, as well as optional additives such as buffers appropriate to adjust the pH to its optimal value.

A single vial kit may be ready for use following addition of the radionuclide ion, such as pertechnetate. A multi-vial kit may be ready for use by addition of the radionuclide ion, such as pertechnetate, to the vial containing exchange ligand and reducing agent, and after waiting an appropriate period of time for formation of a labile complex, the contents of this vial are added to the second vial containing a source of the desired ligand. After a reaction time of about 1 to 60 minutes, the complex of the present invention is formed. It is advantageous that the contents of both vials of this multi-vial kit be lyophilized. As described for the single vial kit, additional additives may be employed to improve the radiochemical purity and stability of the final product, or to aid in the production of the kit.

Alternatively, the multi-vial kit may comprise the desired ligand in one vial and a source of reducing agent such as stannous ion in a second vial. Pertechnetate may be added to the vial containing ligand, and then the contents of the second vial added to initiate labeling. As above, the quantity and type of ligand, buffer pH and reducing agent may be selected based on the nature of the desired ligand used. Again, it is advantageous that the contents of both vials be lyophilized.

All stereoisomers of the compounds and complexes of the present invention are contemplated herein, whether alone (that is, substantially free of other isomers), in a mixture of certain stereoisomers (for example, as a racemate) or in any other mixture thereof. Stereoisomeric mixtures may be separated, for example, by use of a suitable chiral column. A desired stereoisomer may also be prepared employing chiral starting materials or intermediates.

The following Examples further illustrate specific embodiments of this invention, and should not be construed to limit the scope or spirit of the present claims.

EXAMPLE 1

Synthesis of 3,3,5,9,9-Pentamethyl-4,5,8-triazaundecane-2,10-dione dioxime

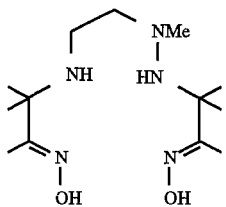

A. Preparation of aziridine

Ethanolamine (25.0 g, 0.41 mol) was added dropwise to a solution of 1:1 sulfuric acid:water mixture (sulfuric acid, 18N, 23 mL and water, 23 mL) with stirring while cooling the reaction vessel in an ice bath. After the addition, the mixture was heated to 200° C. and kept at that temperature for 1 h. Water was removed by distillation and the reaction mixture was cooled. The precipitated sulfate salt was filtered and washed with anhydrous ethanol. Yield 40.0 g. The sulfate was boiled in a flask with a reflux condenser and in the presence of 40% sodium hydroxide (160 mL) for 30 minutes and then distilled using an efficient condenser. About 35 ml of the distillate was collected boiling at 70°–95° C. Solid KOH was added to the above distillate and dried overnight in the refrigerator. The oil which separated was removed and redistilled. The fraction boiling at 55°–60° C. was collected and distilled one more time in the presence of sodium metal. Aziridine, boiling at 56°–57° C., was collected as an oil. Yield: 4.5 g (26%). $^1$H NMR (CDCl$_3$) : ε 1.6 (s, N—CH$_2$).

B. Preparation of 1-(2-Aminoethyl)-1-methylhydrazine

Aziridine (4.5 g, 0.105 mol) was added dropwise over a period of 1 h to a refluxing mixture of N-methylhydrazine (25.0 g, 0.54 mol) and ammonium chloride (1.0 g). The mixture was refluxed for an additional 16 h, then concentrated using a rotary evaporator under aspirator pressure to remove any low boiling impurities. The resulting oil was distilled under low pressure to yield a colorless liquid (4.4 g, b.p. 93°–95° C./80–85 mm). The liquid was redistilled under nitrogen to yield the title product as a colorless oil. Yield: 2.2 g (25%). b.p. 160°–162° C. (Trepanier et al., *J. Med. Chem.*, 10, 228 (1967), 155°–165° C.). $^1$H NMR (D$_2$O) : ε 2.3 (s, 3H, N—Me), 2.5 (t, 2H, CH$_2$—N—Me) and 2.7 (t, 2H, CH$_2$—NH$_2$).

C. Preparation of 3,3,5,9,9-Pentamethyl-4,5,8-triazaundecane-2,10-dione dioxime

A solution of the 1-(2-aminoethyl)-1-methylhydrazine (1.8 g, 20 mmol) and diisopropylethylamine (6.5 g, 50 mmol) was added dropwise to a solution of 3-chloro-3-methyl-2-nitrosobutane (Vassian, *Inorg., Chem.*, 6, 2043 (1967)) (6.6 g, 50 mmol) in dry AcN (25 mL), while cooling the reaction mixture in an ice-salt bath. After the addition, the reaction mixture was stirred under reflux for an additional 6 h. The solution was concentrated to a paste under reduced pressure and then 20 mL of water was added. The solution was brought to pH 10–11 with addition of 4N NaOH and extracted with dichloromethane. The organic layer was dried and concentrated to give a semi-solid which was recrystallized from ethanol to yield the title product as a colorless solid. Yield 1.5 g (26%). m.p. 130°–131° C. $^1$H NMR (DMSO-d$_6$) : ε 1.5 (s, 12H, CMe$_2$), 2.08 (s, 3H, C═CCH$_3$), 2.12 (s, 3H, C═CCH$_3$), 2.3 (bs, 1H, NH), 2.6 (s, 3H, N—Me) , 2.64 (bt, 2H, CH$_2$—NMe), 2.9 (t, 2H, CH$_2$—NH) and 3.5 (bs, 1H, NH—NMe), 10.8 (s, 1H, N=OH) and 10.85 (s, 1H, N=OH). M.S. (M+H)$^+$ 288. Anal. Calcd: C, 54.33; H, 10.17; N, 24.37. Found: C, 54.48; H, 9.91;N, 24.04.

EXAMPLE 2

Preparation of the $^{99m}$Tc complex of the ligand of Example 1

Oxo[3,3,5,9,9-pentamethyl-4,5,8-triazaundecane-2,10-dione dioximato! (3-)-N,N',N",N'"]technetium-$^{99m}$Tc(V)

The ligand of Example 1 (2 mg) was dissolved in saline (1.5 mL) and eluate from a $^{99}$Mo/$^{99m}$Tc generator (0.5 mL, 15–35 mCi). Saturated tin tartrate solution in saline (50 µL) was added. After 5 minutes at room temperature, the radiochemical purity of the title complex was determined by HPLC (PRP-1 10 µ, 70/30 AcN/0.1M NH$_4$OAc, pH 4.6, 1 mL/min.) as >99%.

EXAMPLE 3

Preparation of the $^{99}$Tc complex of the ligand of Example 1

[Tetra-n-butyl ammonium][TcO(Eg)$_2$] (Eg=ethylene glycolate) was prepared in situ by mixing TBATcOCl$_4$ (342.6 mg), ethylene glycol (250 µL), and 0.75M sodium acetate in methanol (3.7 mL). The ligand of Example 1 (198 mg) was dissolved in methanol (10 mL), and this solution was added to 5 the solution of [tetra-n-butyl ammonium] [TcO(Eg)$_2$]. The reaction mixture was stirred at room temperature for 15 min. Solvents were evaporated under reduced pressure. Product was purified with a silica gel column eluted with 5% MeOH/CH$_2$Cl$_2$ and recrystallized with ether/hexane. The title complex was obtained as a light brown powder (172.6 mg, 63% yield). MS [m/z (species)]: (FAB+): 400 (M+H), 384 (M—O); (FAB-): 398 (M—H) . $^1$H NMR (ϵ, CDCl$_3$): 3.61 (m, 2H, CH$_2$), 3.14 (m, 1H, CH$_2$), 2.70 (m, 1H, CH$_2$), 2.39 (s, 3H, CH$_3$), 2.33 (s, 3H, CH$_3$), 2.26 (s, 3H, CH$_3$), 1.54 (s, 3H, CH$_3$), 1.47 (s, 3H, CH$_3$), 1.40 (s, 3H, CH$_3$), 1.36 (s, 3H, CH$_3$). IR 926 cm$^{-1}$ ($v_{Tc=O}$)

EXAMPLE 4

Synthesis of 11-(2-Nitro-1H-imidazol-1-yl)-3,3,5,9,9-pentamethyl-4,5,8-triazaundecane-2,10-dione dioxime

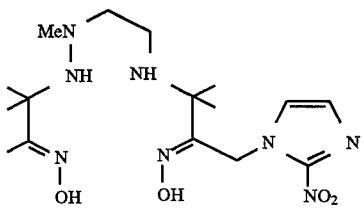

A. Preparation of t-Boc aziridine

Di-t-butyl-dicarbonate (22.0 g, 0.1 mol) in dichloromethane (20 mL) was added dropwise to a stirred solution of aziridine (4.3 g, 0.1 mol, Example 1(A)) and triethylamine (15.0 g, 0.15 mol) in dichloromethane (10 mL). After 2 h at room temperature, the reaction mixture was concentrated to −10 mL by rotary evaporation at room temperature, then treated with water (100 mL). The organic layer was separated and thoroughly washed with water (5×50 mL). Removal of the solvent yielded the title product, which was used in the next step without further purification. Yield: 2.1 g (15%). $^1$H NMR (CDCl$_3$) : ϵ 1.5 (s, 9H, C—Me) and 2.15 (s, 4H, N—CH$_2$).

B. Preparation of N-(2-t-Boc aminoethyl)-1-methyl hydrazine

A solution of t-Boc aziridine (2.1 g, 0.0141 mol) in ether (5 mL) was added dropwise to ice-cooled N-methyl hydrazine (6.75 g, 0.141 mol) over a period of 1 h. The reaction mixture was stirred at room temperature for an additional 12 hours. All the volatiles were removed under reduced pressure to yield a thick liquid. This product was used in the next step without any further purification. Yield: 2.5 g (96%). $^1$H NMR (CDCl$_3$): ϵ 1.5 (s, 9H, C—Me), 2.4 (s, 3H, N—Me), 2.5 (t, 2H, Me—N—CH$_2$), 2.9 (s, 2H, N—NH$_2$), 3.4 (m, t-Boc-NH—CH$_2$) and 5.4 (bs, 1H, NH-t-Boc). M.S.: [M+H]$^+$=190.

C. Preparation of 1-t-Boc amino-3,4-diaza-3,5,5-trimethylheptan-6-one oxime

Anhydrous potassium carbonate (1.4 g, 10 mmol) was added to a stirred solution of N-(2-t-Boc aminoethyl)-1-methyl hydrazine (1.17 g, 5.2 mmol) in AcN (10 mL). The reaction mixture was cooled in an ice-salt bath and solid 3-chloro-3-methyl-2-nitrosobutane (Example 1(C), (0.745 g, 5.5 mmol) was added in portions over a period of ½ h with stirring under nitrogen. The reaction mixture was allowed to come to room temperature and stirred for 2 hours more. Solvent was evaporated and the residue was treated with water (50 mL). The aqueous solution was extracted with ether (5×20 mL) and the combined organic layer was washed with water and dried (Na$_2$SO$_4$). Evaporation of the solvent yielded a viscous oil which was chromatographed on a flash silica gel column. Elution with 6:4 hexanes/ethyl acetate yielded the product as a colorless thick liquid. Yield: 0.78 g (52%). $^1$H NMR (CDCl$_3$): ϵ 1.2 (s, 6H, N—C—Me$_2$), 1.5 (s, 9H, —O—C—Me$_3$), 1.9 (s, 3H, N=C—Me), 2.3 (bs, 1H, Me—N—NH), 2.4 (s, 3H, N—Me), 2.6 (t, 2H, Me—N—CH$_2$), 3.2 (m, 2H, t-Boc-NH—CH$_2$), 5.3 (bs, 1H, t-boc-NH) and 9.1 (bs, 1H, —OH). M.S.: [M+H]$^+$=289.

D. Preparation of 11-(2-Nitro-1H-imidazol-1-yl-3,3,5,9, 9-pentamethyl-4,5,8-triazaundecane-2,10-dione dioxime 1-t-Boc amino-3,4-diaza-3,5,5-trimethylheptan-6-one oxime (0.288 g, 1 mmol) was dissolved in saturated methanolic HCl (5 mL) and stirred for 10 min at room temperature. The solution was concentrated under reduced pressure and the paste was coevaporated with chloroform (3×5 mL) to yield a colorless solid. The solid was then treated with methanolic ammonia (10 mL) and again concentrated under reduced pressure. The resulting paste was dried under high vacuum for 2 h at room temperature and then dissolved in dry acetonitrile (5 mL). Solid potassium carbonate (0.42 g, 3 mmol) was added and the mixture was stirred for 5 min. 3-Chloro-3-methyl-2-nitroso-1-(2-nitro-1H-imidazol-1-yl) butane (U.S. application Ser. No. 08/054,120, filed Apr. 27, 1993 by Linder et al. (Attorney Docket No. RB90b)) (0.325 g, 1.5 mmol) was added in one portion and the reaction mixture was stirred at room temperature for 30 min. Flash silica gel (5.0 g) was added to the reaction mixture and then the solvent was removed under vacuum to yield a free flowing powder. The silica gel containing the mixture was loaded onto a flash column and chromatographed. Elution with 9:1 methylene chloride/methanol yielded the title product as a pale yellow solid. Yield: 5.0 mg (1%). m.p. 132°–134° C. $^1$H NMR (CDCl$_3$) : ϵ 1.1 (s, 6H, C—Me), 1.2 (s, 6H, C—Me), 1.8 (s, 3H, C=N—Me), 2.2 (s, 3H, N—Me), 2.3 (bm, 2H, NMe—CH$_2$), 2.5 (bm, 2H, NH—CH$_2$), 5.3 (s, 2H, imid-CH$_2$), 7.0 (s, 1H, imid-H) and 7.2 (s, 1H, imid-H). M. S. [M+H]$^+$ 399.

The ethyl analog of the title compound having the structure:

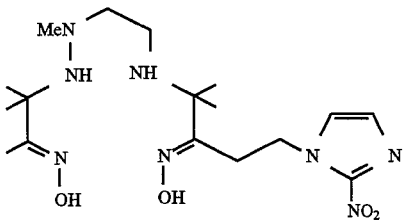

may be made by a procedure analogous to that described above.

EXAMPLE 5

Tc-99m Complex of the Ligands of Examples 4 and 6

The ligand of Example 4 (1.2 mg) was dissolved in EtOH (0.2 mL) and eluate from a $^{99}$Mo/$^{99m}$Tc generator (0.3 mL, 15–30 mCi) was added. A saturated solution of stannous tartrate in saline (50 μL) was added, and the reaction mixture was shaken, and allowed to stand at room temperature for 10 minutes. The radiochemical purity of the complex of the Example 4 ligand was determined as described in Example 2, and was found to be >96%.

The Tc$^{99m}$ complex of the ligand of Example 6 was prepared in the above manner, and was found to have a radiochemical purity >90%. The complexes thus formed from the ligands of Examples 4 and 6, respectively, had the names:

oxo[11-(2-nitro-1H-imidazol-1-yl)-3,3,5,9,9-pentamethyl-4,5,8-triazaundecane-2,10-dione dioximato](3-)-N,N',N'',N''']technetium$^{-99m}$Tc(V); and oxo[1-(2-nitro-1H-imidazol-1-yl)-3,3,5,9,9-pentamethyl-4,5,8-triazaundecane-2,10-dione dioximato](3-)-N,N',N'', N''']technetium$^{-99m}$Tc(V).

EXAMPLE 6

Synthesis of 1-(2-Nitro-1H-imidazol-1-yl)-3,3,5,9,9-pentamethyl-4,5,8-triazaundecane-2,10-dione dioxime

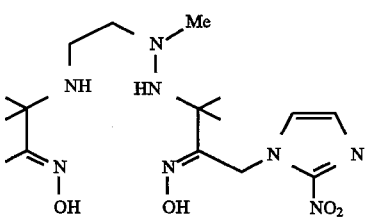

A. Preparation of 1-t-Boc-amino-3,4-diaza-7-(2-nitro-1H-imidazol-1-yl)-3,5,5-trimethylheptan-6-one oxime Anhydrous potassium carbonate (1.4 g, 10 mmol) and 3-chloro-3-methyl-2-nitroso-1-(2-nitro-1H-imidazol-1-yl)butane (6.6 g, 50 mmol, Example 4(D)) were added to a stirred solution of N-(2-t-Boc-aminoethyl)-1-methylhydrazine (1.89 g, 20 mmol, Example 4(B)) in dry dichloromethane (10 mL). The stirred reaction mixture was heated under reflux, under nitrogen, for 24 h. On cooling, the reaction mixture was filtered and the residue was washed with dichloromethane. The filtrate and wash were combined, and solvent was removed on a rotary evaporator. The crude product was purified by flash column chromatography (silica gel: 6:4 ethyl acetate/hexanes). A semi-solid was obtained, which was recrystallized from isopropyl ether to give the product as a bright yellow solid. Yield: 1.5 g (36%). m.p. 141°–142° C. $^1$H NMR (CDCl$_3$) : ε 1.2 (s,6H, C Me$_2$ methyls), 1.4 (s, 9H, t-Boc methyls), 2.15 (s, 3H, N—Me), 2.4 (s, 3H, N—Me), 2.6 (bm, 2H, Me—N—CH$_2$), 3.1 (bm, 2H, t-bocNH-CH$_2$), 5.0 (bs, 1H, t-Boc NH), 5.3 (s, 2H, imid-CH $_2$), 7.05 (s, imid-H), 7.1 (s, 1H, imid-H), 8.45 (bs, 1H, N—OH) and 9.9 (bs, 1H, N—OH). M.S. [M+H]$^+$ 400. Anal. Calc. (C$_{16}$H$_{29}$N$_7$O$_5$: C, 48.11; H, 7.32; N, 24.55. Found: C, 47.99; H, 7.33;N, 24.48.

B. Preparation of 1-(2-Nitro-1H-imidazol-1-yl)-3,3,5,9,9-pentamethyl-4,5,8-triazaundecane-2,10-dione dioxime 1-t-Boc-amino-3,4-diaza-7-(2-nitro-1H-imidazol-1-yl)-3,5,5-trimethylheptan-6-one oxime (0.5 g, 1.25 mmol) was dissolved in methanol saturated with HCl gas (5 mL). The solution was allowed to stand at room temperature for 5 min, then solvent and volatile materials were removed under reduced pressure. The resulting fluffy solid was treated with methanol saturated with ammonia gas (10 mL). Solvent and volatile materials were removed under reduced pressure at room temperature, and the resultant solid was dried under vacuum at room temperature for 2 hours. The solid was suspended in dry acetonitrile (5 mL) and potassium carbonate (0.35 g, 2.5 mmol) was added, and the mixture was stirred at room temperature for 5 min. 3-Chloro-3-methyl-2-nitrosobutane (0.335 g, 2.5 mmol, Example 1(C)) was added in one portion and the reaction mixture was stirred for 24 h at room temperature. The reaction mixture was filtered and the isolated solid was washed with acetonitrile. The combined acetonitrile fractions were concentrated to yield a paste which was chromatographed on flash silica gel column. Elution with 9:1 dichloromethane-methanol yielded a fluffy colorless solid, which was recrystallized from acetonitrile/isopropyl ether repeatedly until a constant melting point was observed. Yield: 0.061 g (12%). m.p. 156°–158° C. $^1$H NMR (DMSO-d$_6$): ε 1.6 (s, 6H, —CMe$_2$), 1.7 (s, 6H, —C—Me$_2$), 2.0 (s, 3H, —CH$_3$—C=NOH), 2.8 (s, 3H, N—Me), 3.2 (2m, 4H, N—CH$_2$), 5.7 (s, 2H, —CH$_2$-imid), 7.5 (s, 1H, imid-H), 7.6 (s, 1H, imid-H), 11.5 (s, 1H, N—OH) and 11.7 (s, 1H, N—OH). HRMS [M+H]$^+$ Calcd. for C$_{16}$H$_{31}$N$_8$O$_4$: 399.2468. Found: 399.2477. Anal.; Calcd. for C$_{16}$H$_{31}$ClN$_8$O$_4$·0.25 H$_2$O: C, 43.83; H, 7.01; N, 25.55; Cl, 8.09. Found: C, 43.99; H, 7.14; N, 25.39; Cl, 7.6.

The ethyl analog of the title compound having the structure

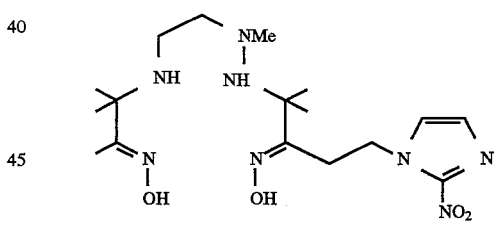

may be made by a procedure analogous to that described above.

EXAMPLE 7

Synthesis of 3,3,9,9-Tetramethyl-5-oxa-4,8-diazaundecane-2,10-dione dioxime

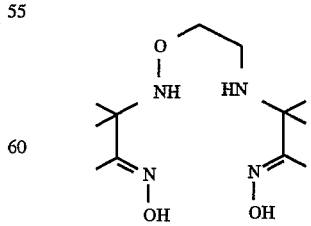

A. Preparation of 1-Bromo-2-t-Boc-aminoethane

Bromoethylamine hydrobromide (30.7 g, 0.15 mole) was added to a stirred slurry of sodium carbonate (16.0 g, 0.15 mole) in dioxane-water (2:1, 300 mL) and the mixture was stirred at 0° C. for 15 minutes. Di-t-butyl dicarbonate (33 g, 0.15 mole) was added to this mixture and stirring at 0° C. was continued for one hour, followed by stirring at room temperature for 12 hours. Dioxane-water was removed on a rotary evaporator and the residue was treated with water (400 mL). The mixture was extracted with ether. The organic extract was washed with water and dried ($Na_2SO_4$). Ether was evaporated and the oil thus obtained was used for the next step without further purification. Yield: 31 g (92%). $^1$H NMR ($CDCl_3$): ε 1.48 [s, 9H, $C(CH_3)_3$], 3.42 (m, 2H, $BrCH_2CH_2NHtBoc$), 3.54 (m, 2H,$BrCH_2CH_2NHtBoc$), 5.08 (bs, 1H, NH).

B. Preparation of N-(2-t-Boc-amino ethoxy)phthalimide

Sodium hydride (2.4 g, 0.1 mol) was added portionwise to a solution of N-hydroxyphthalimide (16.13 g, 0.1 mol) in dry DMF (200 mL) over a period of 30 min. A dark red precipitate was formed and the mixture was stirred for an additional 30 minutes at room temperature. 1-Bromo-2-t-Boc-aminoethane (22.4 g, 0.1 mol) was added and the mixture was stirred at 70° C. for 24 hours. DMF was removed under vacuum and the residue was poured into water. The solid which formed was isolated by filtration and air dried. The crude product was dissolved in ethyl acetate (200 mL) and the solution was passed through a bed of neutral alumina to remove unreacted N-hydroxyphthalimide (unreacted N-hydroxyphthalimide remained as an orange band on alumina). The alumina bed was washed with ethyl acetate-hexane (6:4) until no more UV visible material eluted, then combined ethyl acetate-hexane fractions were evaporated on a rotary evaporator to afford the title product as a white solid. The product was crystallized from hexane. Yield: 15.0 g. (50%). mp. 113°–114° C. $^1$H NMR ($CDCl_3$) ε 1.48 [s, 9H, $C(CH_3)_3$], 3.42 (m, 2H, $OCH_2CH_2NHtBoc$), 4.21 (m, 2H,$OCH_2CH_2NHtBoc$), 5.68 (bs, 1H, NH), 7.7–7.82 (m, 4H, ArH). MS: (M+H)$^+$=307. Anal. calcd. for: $C_{15}H_{18}N_2O_5$. C, 58.82; H, 5.92, N, 9.15. Found: C, 58.97, H, 5.95; N, 9.29.

C. Preparation of 2-(Aminoxy)-1-t-Boc-aminoethane

Hydrazine (98%, 2.1 g, 0.065 mol) was added to a solution of crude N-(2-t-Boc-aminoethoxy)phthalimide (20 g, 0.065 mol) in ethanol (50 mL) and the mixture was refluxed for 2 hrs. The solid which formed was removed by filtration and the filtrate was evaporated on a rotary evaporator. The residue thus obtained was triturated with ethyl acetate and the resultant precipitate was removed by filtration. The ethyl acetate solution was evaporated on a rotary evaporator to give the title product amine as an oil. Yield: 10 g. (83%). $^1$H NMR ($CDCl_3$) ε 1.48 [s, 9H, $C(CH_3)_3$], 3.42 (m, 2H, $OCH_2CH_2NHtBoc$), 4.21 (m, 2H,$OCH_2CH_2NHtBoc$), 5.68 (bs, 1H, NH), 7.7–7.82 (m, 4H, ArH).

D. Preparation of 7-t-Boc-amino-4-aza-3,3-dimethyl-5-oxaheptan-2-one oxime

A solution of 3-chloro-3-methyl-2-nitrosobutane (4.1 g, 0.03 mol, Example 1(C)) was added to a solution of crude 2-(aminoxy)-1-t-Boc aminoethane (5.3 g, 0.03 mol) and diisopropylethylamine (4.5 g, 0.035 mol) and the mixture was stirred at room temperature for 6 h. Acetonitrile was removed on a rotary evaporator and the thick viscous oil was treated with water and extracted with ether (2×100 mL). The ether solution was dried with sodium sulfate and the ether was removed on a rotary evaporator to yield 8.2 g of crude product as a thick viscous oil. This was purified on a silica gel column. Elution with methylene chloride:methanol 95:5 gave the pure title product as a thick viscous oil. Trituration with hexane afforded the product as a crystalline white solid, which was crystallized from hexane. Yield 4.2 g (44%). mp. 97°–98° C. $^1$H NMR ($CDCl_3$) ε 1.24 [s, 6H, $C(CH_3)_2$], 1.45 [s, 9H, $C(CH_3)_3$], 1.91 (s, 3H, $CH_3$), 3.32 (m, 2H, $OCH_2CH_2NHtBoc$), 3.70 (m, 2H,$OCH_2CH_2NHtBoc$), 5.09 (bs, 1H, NHtBoc), 5.84 (bs, 1H, NH), 8.55 (bs, 1H, NOH). MS: (M+H)$^+$=276. Anal. calcd. for $C_{12}H_{25}N_3O_4$: C, 52.35; H, 9.15, N, 15.26. Found: C, 51.97; H, 9.10 ; N, 15.05.

E. Preparation of 7-Amino-4-aza-3,3-dimethyl-5-oxaheptan-2-one oxime

Methanolic HCl (10 mL) was added to a solution of 7-t-Boc-amino-4-aza-3,3-dimethyl-5-oxaheptan-2-one oxime (2.75 g, 0.01 mol) in methanol (20 mL), and the mixture was stirred at room temperature for 15 min. Solvent was removed on a rotary evaporator and the residue was neutralized with methanolic ammonia. The ammonium chloride which formed was removed by filtration and the methanolic solution was concentrated to give the title product as a white solid. Yield 1.75 g. The free amine was used in the next step without further purification. $^1$H NMR ($D_2O$) ε 1.4 [s, 6H, $C(CH_3)_2$], 1.82 (s, 3H, $CH_3$), 3.29 (m, 2H, $OCH_2CH_2NH_2$), 4.25 (m, 2H,$OCH_2CH_2NH_2$).

F. Preparation of 3,3,9,9-Tetramethyl -5-oxa-4,8-diazaundecane-2,10-dione dioxime 3-Chloro-3-methyl-2-nitrosobutane (1.45 g, 0.011 mol, Example I(C)) was added to a mixture of 7-amino-4-aza-3, 3-dimethyl-5-oxaheptan-2-one oxime (1.75 g, 0.01 mol) and diisopropylethylamine (1.4 g, 0.011 mol) in acetonitrile (15 mL), and the mixture was stirred at room temperature for 6 hrs. The solid which formed was isolated by filtration and air dried. This solid was adsorbed onto silica gel (3.0 g) and the mixture was loaded onto a silica gel column (packed with methylene chloride: methanol, 9:1) and eluted with a mixture of methylene chloride: methanol, 9:1 (150 mL) followed by methylene chloride: methanol, 9:2 (200 mL). Fractions containing the product were collected and evaporated on a rotary evaporator. The solid obtained was recrystallized from acetonitrile to yield the title product. Yield 0.8 g. mp.194°–195° C dec. $^1$H NMR ($CDCl_3$) ε 1.24 [s, 6H, $C(CH_3)_2$], 1.45 [s, 9H, $C(CH_3)_3$], 1.91 (s, 3H, $CH_3$), 3.32 (m, 2H, $OCH_2CH_2NHtBoc$), 3.70 (m, 2H,$OCH_2CH_2NHtBoc$ ), 5.09 (bs, 1H, NHtBoc), 5.84 (bs, 1H, NH), 8.55 (bs, 1H, NOH). MS: (M+H)$^+$=275.

EXAMPLE 8

Synthesis of 11-(2-Nitro-1H-imidazol-1-yl) -3,3,9,9-tetramethyl-5-oxa-4,8-diazundecane-2,10-dione dioxime

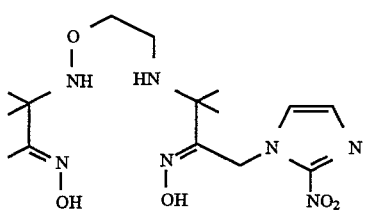

3-Chloro-3-methyl-2-nitroso-1-(2-nitro-1H-imidazol-1-yl)butane (2.46 g, 0.01 mol, Example 4(D)) was added to a mixture of 7-amino-4-aza-3,3-dimethyl-5-oxaheptan-2-one oxime (1.75 g, 0.01 mol, Example 7(E)) and diisopropylethylamine (1.4 g, 0.011 mol) in acetonitrile (20 mL), and the mixture was stirred at room temperature for 24 hrs. Acetonitrile was removed on a rotary evaporator and the thick viscous oil thus obtained was chromatographed over silica gel (methylene chloride: methanol 9:1). Fractions containing the product were collected and evaporated on a rotary evaporator. The resultant solid was recrystallized from acetonitrile to yield the title product. Yield 0.68 g. (20%). mp. 132°–33° C. dec. $^1$H NMR (DMSO-d$_6$) ∈ 1.10 [s, 6H, C (CH$_3$)$_2$], 1.18 [s, 6H, C(CH$_3$)$_2$], 1.74(s, 3H, CH$_3$), 2.31 (m, 2H, OCH$_2$CH$_2$NH), 3.44 (m, 2H,OCH$_2$CH$_2$NH), 5.22 (s, 2H, CH$_2$N<), 7.10 and 7.31 (s, 2H, imiH). 10.42 and 11.4 (s, 1H, NOH). MS: (M+H)$^+$=386. HRMS: Calcd. (M+H)$^+$=386.2152$^+$; Found: (M+H)$^+$=386.2162$^+$. Anal. calcd. for C$_{15}$H$_{27}$N$_7$O$_5$: C, 46.74; H, 7.06, N, 25.44; Found: C, 47.18, H, 7.10; N, 24.69.

EXAMPLE 9

Synthesis of 1-(2-Nitro-1H-imidazol-1-yl)-3,3,9,9-tetramethyl-5-oxa-4,8-diazaundecane-2,10-dione dioxime

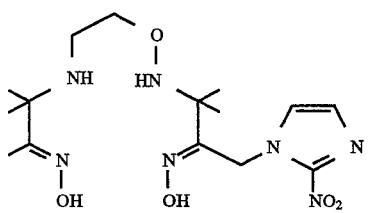

A. Preparation of 7-t-Boc-amino-4-aza-3,3-dimethyl-1-(2-nitro-1H-imidazol-1-yl )-5-oxaheptan-2-one oxime 3-Chloro-3-methyl -2-nitroso-1-(2-nitro-1H-imidazol-1-yl)butane (2.46 g, 0.01 mol, Example 4(D)) was added to a solution of 2-(aminoxy)-1-t-Boc-aminoethane (1.76 g, 0.01 mol, Example 7(C)) and diisopropylethylamine (1.32 g, 0.0102 mol) in acetonitrile (30 mL), and the mixture was stirred at room temperature for 24 hrs. Acetonitrile was removed on a rotary evaporator and the thick viscous oil thus obtained was purified by column chromatography (hexane - ethyl acetate 7:3). UV visible fractions were collected and evaporated to give a thick viscous oil which solidified on standing to yield the title product. Yield 2.68 g (70%.). mp. 97°–98° C. $^1$H NMR (CDCl$_3$) ∈ 1.24 [s, 6H, C(CH$_3$)$_2$], 1.45 [s, 9H, C(CH$_3$)$_3$], 1.91 (s, 3H, CH$_3$), 3.22 (m, 2H, OCH$_2$CH$_2$NHtBoc), 3.51 (m, 2H,OCH$_2$CH$_2$NHtBoc), 4.70 (bs, 1H, NHtBoc), 5.34 (s, 2H, CH$_2$<N), 7.10 and 7.31 (s, 2H, imiH), 8.66 (bs, 1H, NOH).

B. Preparation of 7-Amino-4-aza-3,3-dimethyl-1-(2-nitro-1H-imidazol-1-yl)-5-oxaheptan-2-one oxime Methanolic HCl (10 mL) was added to a solution of 7-t-Boc-amino-4-aza-3,3-dimethyl-1-(2-nitro-1H-imidazol-1-yl)-5-oxaheptan-2-one oxime (2.68 g, 0.007 mol) in methanol (15 mL), and the mixture was stirred at room temperature for 15 min. Solvent was removed on a rotary evaporator and the residue was neutralized with methanolic ammonia. The ammonium chloride which formed was removed by filtration and the filtrate was concentrated to give the title product as a white solid. Yield: 1.72 g (60%). This product was used in the next step without further purification. $^1$H NMR (D$_2$O) ∈ 1.4 [s, 6H, C(CH$_3$)$_2$], 3.21 (m, 2H, OCH$_2$CH$_2$NH$_2$), 4.21 (m, 2H,OCH$_2$CH$_2$NH$_2$), 5.34 (s, 2H, CH$_2$<N), 7.10 and 7.31 (s, 2H, imiH).

C. Preparation of 1-(2-Nitro-1H-imidazol-1-yl)-3,3,9,9-tetramethyl-5-oxa-4,8-diazaundecane-2,10-dione dioxime 3-Chloro-3-methyl-2-nitrosobutane (1.45 g, 0.011 mol) was added to a mixture of 7-amino-4-aza-3,3-dimethyl-1-(2-nitro-1H-imidazol-1-yl)-5-oxaheptan-2-one oxime (1.72 g, 0.006 mol) and diisopropylethylamine (0.84 g, 0.0065 mol) in acetonitrile (15 mL), and the mixture was stirred at room temperature for 12 hrs. Solvent was removed on a rotary evaporator and the residue was loaded onto a silica gel column (packed with methylene chloride: methanol, 9.5:0.5) and eluted with a mixture of methylene chloride: methanol, 9:1. Fractions containing the product were collected and evaporated on a rotary evaporator. The resultant solid obtained was recrystallized from acetonitrile to yield the title product. Yield: 0.6 g (26%). mp. 149°–50° C. dec. $^1$H NMR (DMSO-d$_6$) ∈ 1.16 [s, 6H, C(CH$_3$)$_2$], 1.18 [s, 6H, C(CH$_3$)$_2$], 1.68(s, 3H, CH$_3$), 2.33 (m, 2H, OCH$_2$CH$_2$NH), 3.49 (m, 2H,OCH$_2$CH$_2$NH), 5.23 (s, 2H, CH$_2$N<), 7.10 and 7.28 (s, 2H, imiH), 10.43 and 11.43 (s, 1H, NOH). MS: (M+H)$^+$= 386. Anal. calcd. for: C$_{15}$H$_{27}$N$_7$O$_5$, C, 46.74; H, 7.06, N, 25.44; Found: C, 47.46, H, 7.11; N, 25.00.

EXAMPLE 10

Synthesis of 12-(2-nitro-1H-imidazol-1-yl)-3,3,9,9-tetramethyl-7-oxa -4,8-diaza-2,10-dodecanedione, dioxime

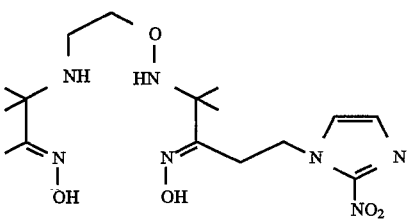

A. Preparation of 4-chloro-4-methyl-1-(2-nitro-1H-imidazol-1-yl)-3-nitrosopentane To a cooled (0°–5° C.) solution of 4-methyl-1-(2-nitro-1H-imidazol-1-yl)-3-pentene (4.0 g, 0.02 mol) (Example 11(A); synthesis is also described in U.S. patent application Ser. No. 08/054,120 recited above) in isoamyl nitrite (26 g, 30 mL, 0.22 mol) was added concentrated hydrochloric acid (3.5 mL, 0.035 mol) with stirring. The reaction mixture was maintained below 5° C. during the addition and stirred at 5° C. for an additional 2 hrs. The solid formed was filtered and washed with cold ether:ethanol (3:1, 150 mL) and dried. Yield: 5.0 g (96%). mp: 105°–107° C. $^1$H NMR (DMSO) ∈ 1.72 [s, 6H, C(CH$_3$)$_2$], 2.94 (t, 2H, CH$_2$CH$_2$N<), 4.65 (t, 2H, CH$_2$CH$_2$N<), 7.16 and 7.54 (s, 2H, imi H), 11.42 (s, 1H, NOH). MS: (M+H)$^+$=261.

B. Preparation of 8-t-Boc-amino-5-aza-4,4-dimethyl-1-(2-nitro-1H-imidazol-1-yl)-6-oxaoctan-3-one oxime To a suspension of 4-chloro-4-methyl-1-(2-nitro-1H-imidazol-1-yl)-3-nitrosopentane (2.6 g, 0.01 mole) in acetonitrile (50 mL) was added 2-(aminoxy)-1-t-Boc-aminoethane (1.76 g, 0.01 mole, Example 7(C)). To this mixture was added diisopropylethylamine (1.4 g, 0.011 mol), and the mixture was stirred for 48 hrs. The clear solution obtained was concentrated and the resulting greenish thick oil was purified by column chromatography (CH$_2$Cl$_2$: CH$_3$OH, 95:5). U.V. visible fractions were collected, and the solvent was evaporated to give a yellow solid. Yield: 3.12 g (78%). It was recrystallized from hexane-ethyl acetate to give the title product. mp: 117°–118° C. $^1$H NMR (CDCl$_3$) ∈ 1.22 (s, 9H, Boc-CH$_3$), 1.41 and 1.45 [s, 6H, C(CH$_3$)$_2$], 2.92 (m, 2H, OCH$_2$CH$_2$NH-Boc)), 3.33 (m, 2H, CH$_2$CH$_2$C=NOH), 3.73 (m, 2H, OCH$_2$CH$_2$NH-Boc), 4.73 (t, 2H, CH$_2$CH$_2$C=NOH), 7.14 and 7.27 (s, 2H, imiI-H), 8.78 (s, 1H, NH-Boc).

C. Preparation of 1-(2-nitro-1H-imidazol-1-yl)-3,3,9,9-tetramethyl-5-oxa-4,8-diaza-2,10-dodecanedione, dioxime 8-t-Boc-amino-5-aza-4,4-dimethyl-1-(2-nitro-1H-imidazol-1-yl)-6-oxaoctan-3-one oxime (3.0 g, 0.0075 mol)

was treated with methanolic HCl (10 mL) and stirred at room temperature for 2 hrs. Dry ether (200 mL) was added to this solution and the white solid formed was filtered and dried under vacuum. Yield: 2.12 g (72%). The hydrochloride formed (2.12 g, 0.0056 mol) was neutralized with methanolic ammonia. The free amine obtained was suspended in acetonitrile. To this was added 3-chloro-3-methyl-2-nitrosobutane (0.78 g, 0.0058 mol), prepared according to the method of Vassian et al., *Inorg. Chem.*, 6, 2043–2046 (1967). This was followed by diisopropylethylamine (0.8 g, 0.0062 mol), and the reaction mixture was stirred at room temperature for 48 hrs. Acetonitrile was removed on a rotary evaporator and the residue was dissolved in water (5 mL). The solution was made basic (pH 8.5) by the addition of NaOH and extracted with ethyl acetate (2×10 mL), and dried over $Na_2SO_4$. Removal of ethyl acetate gave a thick oil which was dried under vacuum. The thick oil obtained was dissolved in acetonitrile, and the product began to crystallize from the acetonitrile solution. The solid obtained was further recrystallized from acetonitrile. Yield: 0.8 g (36%). mp: 138°–139° C. $^1$H NMR (DMSO-$d_6$) ε 1.10 [s, 12H, C(CH$_3$)$_2$], 1.67 (s, 3H, CH$_3$), 2.34 (m, 2H, OCH$_2$CH$_2$NH), 2.85 (m, 2H, CH$_2$CH$_2$C=NOH), 3.53 (t, 2H, OCH$_2$CH$_2$N), 4.61 (t, 2H, CH$_2$CH$_2$C=NOH), 7.10 and 7.50 (s, 2H, imi-H), 10.41 and 10.78 (s, 2H, CH$_2$C=NOH). Anal. Calcd. for $C_{16}H_{29}N_7O_5$: Found: C, 48.53; H, 7.39; N, 24.65. Calcd.: C, 48.11; H, 7.32; N, 24.55.

EXAMPLE 11

Synthesis of 12-(2-nitro-1H-imidazol-1-yl)-3,3,9,9-tetramethyl-5-oxa-4,8-diaza-2,10-dodecanedione, dioxime

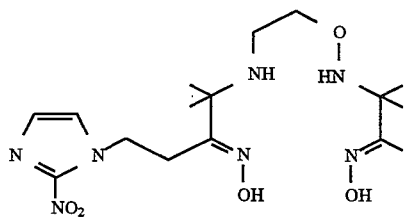

A. Preparation of 4-methyl-1-(2-nitro-1H-imidazol-1-yl)-3-pentene

5-Bromo-2-methyl-2-pentene (15 g, 0.092 mol) was added to a slurry of 2-nitroimidazole (10.4 g, 0.092 mol) and potassium carbonate (12.7 g, 0.092 mol) and refluxed for 24 hrs. Acetone was removed on a rotary evaporator and the residue was purified by column chromatography. Yield 6.2 g (34%). $^1$H NMR (CDCl$_3$) ε 1.44 and 1.68 [s, 6H, =C(CH$_3$)$_2$], 2.53 (m, t 2H, CH$_2$CH$_2$CN<), 4.41 (t, 2H, CH$_2$CH$_2$CN<), 5.06 (m, 1H, CH=C ), 7.03 and 7.12 (s, 2H, imi H). B. Preparation of 12-(2-nitro-1H-imidazol-1-yl)-3,3,9,9-tetramethyl-5-oxa-4,8-diaza-2,10-dodecanedione, dioxime To a mixture of 7-amino-4-aza-3,3-dimethyl-5-oxaheptan-2-one oxime (Example 7(E), 0.875 g, 0.005 mol) and diisopropylethylamine (0.7 g, 0.0055 mol) was added 4-chloro-4-methyl-1-(2-nitro-1H-imidazol-1-yl)-3-nitrosopentane (Example 10(A), 1.3 g, 0.05 mol) and the mixture was stirred at room temperature for 24 hrs. The white solid formed was filtered and dried. This was purified by column chromatography (silica gel, CH$_2$Cl$_2$:CH$_3$OH) followed by recrystallization from acetonitrile. mp 122°–123° C. $^1$H NMR (D$_2$O)ε 1.16 [s, 6H, C(CH$_3$)$_2$], 1.36 [s, 6H, C(CH$_3$)$_2$], 1.81 (s, 3H, CH$_3$), 2.87 (t, 2H, CH$_2$CH$_2$CN<), 3.11 (m, 2H, OCH$_2$CH$_2$NH), 3.86 (m, 2H,OCH$_2$CH$_2$NH), 4.69 (t, 2H, CH$_2$CH$_2$CN<), 7.10 and 7.36 (s, 2H, imiH). Anal. Calcd. for $C_{16}H_{29}N_7O_5$: Found: C, 48.47; H, 7.39; N, 24.12. Calcd.: C, 48.11; H, 7.32; N, 24.55.

EXAMPLE 12

Synthesis of 1,13-bis(2-nitro-1H-imidazol-1-yl)-4,4,10,10-tetramethyl-6-oxa-5,9-diaza-3,11-tridecanedione, dioxime

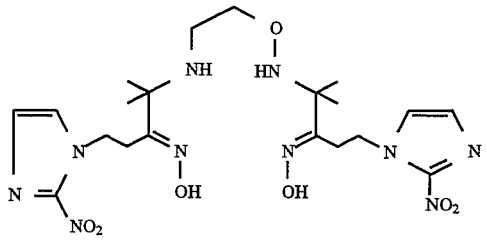

A. Preparation of 2-(aminoxy)-1-aminoethane dihydrochloride 2-(Aminoxy)-1-t-Boc-aminoethane (1.23 g, 7 mmol, Example 7(C)) was suspended in methanol (2 mL). To the suspension, methanolic HCl (5 mL) was added and the mixture was stirred at room temperature for 2 h. A white suspension was obtained. Volatiles were evaporated on a rotary evaporator to give a white solid (1 g, 98%). $^1$H NMR (D$_2$O) d 3.28 (q, 2H, CH$_2$NH$_2$), 4.28 (q, 2H, CH$_2$ONH$_2$).

B. Preparation of 1,13-bis(2-nitro-1H-imidazol-1-yl)-4,4,10,10-tetramethyl-6-oxa-5,9-diaza-3,11-tridecanedione, dioxime 2-(Aminoxy)-1-aminoethane dihydrochloride (1 g, 6.8 mmol) was suspended in acetonitrile (40 mL) and cooled in an ice bath. Diisopropylethylamine (4 g, 31 mmol) was added in small portions. The ice bath was then removed, and 4-chloro-4-methyl-1-(2-nitro-1H-imidazol-1-yl)-3-nitrosopentane (3.7 g, 14.3 mmol, Example 10(A)) was added in one batch. The suspension was stirred under N$_2$ atmosphere at room temperature for 48 hours and became a clear greenish solution. Acetonitrile was evaporated to give a thick gummy residue. TLC (silica gel, 10% CH$_3$OH—CH$_2$Cl$_2$) showed three spots with R$_f$=0.4, 0.7 and 0.95 under UV light. Column chromatography was carried out on silica gel eluted with 10% CH$_3$OH—CH$_2$Cl$_2$. Fractions with R$_f$=0.4 were collected and evaporated on a rotary evaporator. The resulting gummy product was dissolved in acetonitrile (80 mL) and the solution was shaken with a sodium carbonate-saturated water solution (80 mL). The organic layer was collected, washed with sodium chloride-saturated water (3×20 mL) and dried over sodium sulfate. Solvent was removed on a rotary evaporator and diisopropylethylamine was evaporated under vacuum. A slightly yellow solid was obtained. This solid was recrystallized from acetonitrile-water to yield the title product. Yield: 1 g (28%). HPLC (8 micron C$_{18}$ column, gradient elution from 0% B to 60% B in 60 minutes, where A is 0.01% TFA in water and B is 0.01% TFA in acetonitrile) showed one peak at 27.8 min, with a purity of 99%. mp: 90°–92° C. MS: (M+H)$^+$=525. $^1$H NMR (DMSO) d 1.07 (s, 12H, gem-di-CH$_3$), 2.35 (b, 2H, CH$_2$NH), 2.80 (m, 4H, CH$_2$C=NOH), 3.51 (b, 2H, CH$_2$ONH), 4.56 [b, 4H, CH$_2$-(2-nitroimidazole)], 6.55 (b, 1H, NHOCH$_2$), 7.15 and 7.53 (d, 4H, 2-nitroimidazolyl-H), 10.74 and 10.81 (s, 2H, CH$_2$C=NOH). $^{13}$C NMR (DMSO) d 22.99, 25.31, 25.55 and 25.73 (gem-di-CH$_3$), 38.58 (CH$_2$CH$_2$NH), 40.42 and 41.61 [C(CH$_3$)$_3$], 45.92 and 46.08 (CH$_2$CH$_2$C=NOH), 56.82 and 60.79 (CH$_2$C=NOH), 74.33 (OCH$_2$CH$_2$), 127.63 and 127.72 (CH$_2$CH$_2$-(2-nitroimidazole)], 127.76, 127.90, 144.62, 144.70, 158.36 and 158.91 (2-nitroimidazole-C). Anal. Calcd. for $C_{20}H_{32}N_{10}O_7$: Found: C, 46.12; H, 6.17; N, 26.46. Calcd: C, 45.80; H, 6.15; N, 26.7.

EXAMPLE 13

Synthesis of 1-[[2-nitro-1H-imidazol-1-yl)acetyl]amino]-3,3,9,9-tetramethyl-5-oxa-4,8-diaza-2,10-undecanedione, dioxime

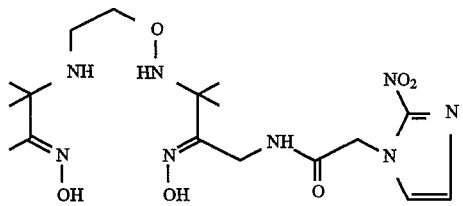

A. Preparation of 3-methyl-1-phthalimido-2-butene

Phthalimide, potassium salt (20.5 g, 0.11 mol) was suspended in dry DMF (100 mL). To the suspension was added 1-bromo-3-methyl-2-butene (14.8 g, 0.1 mol) with stirring. The reaction mixture was stirred under $N_2$ at 45° C. for 24 h. TLC (silica gel, 30% ethyl acetate-hexane) showed one major UV-visible spot with $R_f$=0.65. DMF was removed under vacuum and the residue was taken up with water (200 mL) and extracted with ethyl acetate (3×150 mL). The extracts were combined and dried over $Na_2SO_4$. Evaporation of solvent gave the title product as a white solid. Yield: 21.0 g (98%). mp: 95°–97° C. MS: 233 $(M+NH_4)^+$, 216 $(M+H)^+$. $^1$H NMR (CDCl$_3$) ε 1.71 and 1.83 [s, 6H, C(CH$_3$)$_2$], 4.26 (d, J=6.6 Hz, 2H, CH$_2$CH=), 5.30 (t, 1H, CH=), 7.67 to 7.86 (m, 4H, Aromatic-H).

B. Preparation of 3,3-dimethylallylamine hydrochloride

3-Methyl-1-phthalimido-2-butene (21 g, 0.0986 mol) was dissolved in ethanol (150 mL), and hydrazine (3.8 g, 0.108 mol) was added to this solution. The resulting solution was refluxed for 1 h to give a solid, which was cooled in an ice-bath, neutralized to pH=2 with concentrated HCl, and filtered. The solid was triturated with water (200 mL) and filtered. The filtrates were combined and evaporated under vacuum. The remaining residue was crystallized from ethanol-ether to give the title product as a white solid. Yield: 6 g (50%). mp: 178°–182° C. MS: 122 $(M+H)^+$. $^1$H NMR (D$_2$O) ε 1.62 and 1.68 [s, 6H, =C(CH$_3$)$_2$], 3.49 (d, J=16 Hz, 2H, CH$_2$CH=), 5.18 (t, 1H, CH$_2$CH=).

C. Preparation of ethyl-2-(2-nitro-1H-imidazol-1-yl)acetate

To a mixture of 2-nitroimidazole (8 g, 70 mmol) and dry $K_2CO_3$ (9.7 g, 70 mmol) in acetone (100 mL) was added ethyl bromoacetate (11.6 g, 70 mmol). The suspension was stirred under $N_2$ atmosphere for 48 h. TLC (silica gel, 40% hexane-ethyl acetate) showed a single UV-visible spot with $R_f$=0.55. The suspension was filtered and solid was washed with acetone (3×50 mL). The filtrate and the washings were combined and evaporated on a rotary evaporator to afford a thick yellow oil. Yield: 13.9 g (99%). MS: 217 $(M+NH_4)^+$, 200 $(M+H)^+$. $^1$H NMR (CDCl$_3$) ε 1.30 (t, 3H, OCH$_2$CH$_3$), 4.26 (q, 2H, OCH$_2$CH$_3$), 5.12 (s, 2H, CH$_2$CO), 7.09 and 7.21 (s, 2H, imidazolyl-H).

D. Preparation of 2-(2-nitro-1H-imidazol-1-l)acetic acid

Ethyl 2-(2-nitro-1H-imidazol-1-yl)acetate was suspended in 1N NaOH (100 mL) and stirred at room temperature until it turned into a clear solution. The solution was cooled in an ice-bath and neutralized to pH~2 to give a white precipitate. The solid was filtered and washed with water (3×25 mL). Yield: 11.5 g (97%). MS: 189 $(M+NH_4)^+$, 172 $(M+H)^+$, 170 $(M—H)^-$. $^1$H NMR (DMSO-d$_6$) ε 5.22 [s, 2H, CH$_2$-(2-nitroimidazole)], 7.22 and 7.65 (s, 2H, 2-nitroimidazolyl-H).

E. Preparation of N-(3-methyl-2-butenyl)-2-nitro-1H-imidazol-1-yl)acetamide 2-(2-Nitro-1H-imidazol-1-yl)acetic acid (8.6 g, 50 mmol) was dissolved in DMF (50 mL). Carbonyl diimidazole [CDI] (8.7 g, 60 mmol) was added to the solution in small portions. The reaction mixture was stirred under $N_2$ for 15 min. 3,3-Dimethylallylamine hydrochloride was suspended in DMF (50 mL) and stirred with NaHCO$_3$ (4.2 g, 50 mmol). This suspension was added to the CDI and 2-(2-nitro-1H-imidazol-1-yl)acetic acid in DMF solution. The mixture was stirred under $N_2$ atmosphere at room temperature overnight. TLC (silica gel, 10% methanol-dichloromethane) showed one spot with $R_f$=0.5, indicating completion of the reaction. DMF was evaporated on a rotary evaporator and the residue was triturated with ice-water (125 mL) and filtered. The solid was washed with cold water (3×50 mL) and dried in vacuum to give a white solid. Yield: 7.2 g (61%). mp: 174°–176° C. MS: 254 $(M+NH_4)^+$, 238 $(M+H)^+$. $^1$H NMR (DMSO-d$_6$) ε 1.62 and 1.68 [s, 6H, =C(CH$_3$)$_2$], 3.68 (t, 2H, CH$_2$CH=), 5.08 (s, 2H, COCH$_2$-imidazolyl), 5.14 (t, 1H, CH$_2$CH=), 7.19 and 7.62 (s, 2H, 2-nitroimidazolyl-H), 8.37 (t, 1H, HNCO). Anal. Calcd. for $C_{20}H_{32}N_{10}O_7$: Calcd: C, 50.41; H, 5.92; N, 23.52. Found: C, 50.67; H, 5.97; N 23.38.

F. Preparation of 3-chloro-3-methyl-1-(2-nitro-1H-imidazol-1-yl acetamido)-2-butanone oxime N-(3-methyl-2-butenyl)-2-(2-nitro-1H-imidazol-1-yl)acetamide (3.4 g, 14.3 mmol) was dissolved in isoamyl nitrite (50 mL) at room temperature. The solution was cooled to 0°–5° C. in an ice-salt bath. Concentrated HCl (1.39 mL) was added dropwise. The reaction temperature was maintained between 0° to 5° C. during the addition of HCl. The reaction mixture was stirred in the ice-salt bath for 1 h, filtered, and washed with 1:2 ethanol-ether to give a white solid. Yield: 3.7 g (85%). mp: 154°–160° C. (decomp.). $^1$H NMR (DMSO-d$_6$) ε 1.74 and 1.88 [s, 6H, =C(CH$_3$)$_2$], 4.17 (q, 2H, HNCH$_2$CH=), 5.08 (s, 2H, COCH$_2$-imidazolyl), 5.14 (t, 1H, CH$_2$CH=), 7.18 and 7.63 (s, 2H, 2-nitroimidazolyl-H), 8.51 (t, 1H, HNCO), 11.60 (b, 1H, HON=C).

G. Preparation of 3-(3-N-t-butyloxycarbonyl propyl-1-oxa)amino-3-methyl-1-(2-nitro-1H-imidazol-1-yl acetamido)-2-butanone oxime 2-(Aminoxy)-1-t-Boc-aminoethane (0.28 g, 1.6 mmol, Example 7(C)) was mixed with 3-chloro-3-methyl-1-(2-nitro-1H-imidazol-1-yl acetamido)-2-butanone oxime (0.48 g, 1.6 mmol) in acetonitrile (5 mL). To the suspension was added N,N-diisopropylethylamine (0.21 g, 1.6 mmol). The reaction mixture was stirred under $N_2$ atmosphere at room temperature for 48 hours to yield a clear solution. Acetonitrile was removed and the residue suspended in water (10 mL) and extracted with ethyl acetate (3×15 mL). The organic layer was dried over sodium sulfate and evaporated to dryness. The residue was purified by column chromatography (silica gel, 10% methanol-dichloromethane). Yield: 0.37 g (53%). MS: 444 $(M+H)^+$. $^1$H NMR (CDCl$_3$) ε 1.22 [s, 6H, C(CH$_3$)$_2$], 1.48 (s, 9H, boc-CH$_3$), 3.28 (b, 2H, NHCH$_2$CH$_2$O), 3.70 (t, 2H, NHCH$_2$CH$_2$O), 4.12 (t, 2H, N=CCH$_2$NHCO), 6.04 (b, 1H, HNboc), 7.15 (d, 2H, imidazolyl-H), 7.42 (b, 1H, HNOCH$_2$), 7.84 (b, 1H, HNCO), 10.04 (b, 1H, HON=C).

H. Preparation of 1-[[2-nitro-1H-imidazol-1-yl)acetyl] amino]3,3,9,9-tetramethyl-5-oxa-4,8-diaza-2,10undecanedione, dioxime 3-(3-N-t-Butyloxycarbonyl propyl-1-oxa)amino-3-methyl-1-(2-nitro-1H-imidazol-1-yl acetamido)-2-butanone oxime (0.37 g, 0.84 mmol) was dissolved in methanol (2 mL). HCl-saturated methanol (5 mL) was added to the solution and the mixture was stirred at room temperature for 1 h. volatiles were removed on a rotary evaporator to afford a white solid. $^1$H NMR (D$_2$O), ε 1.42 [s, 6H, C(CH$_3$)$_2$], 3.26 (t, 2H, NHCH$_2$CH$_2$O), 4.02 (s, 2H, N=CCH$_2$NHCO), 4.28 (t, 2H, NHCH$_2$CH$_2$O), 5.10 (s, 2H, COCH$_2$).

This solid was suspended in acetonitrile (4 mL). To this suspension, was added 3-chloro-3-methyl-2-nitrosobutane (0.115 g, 0.84 mmol, Example 10(C)) and N,N-diisopropylethylamine (0.22 g, 1.68 mmol). The suspension was stirred overnight under N$_2$ atmosphere at 45° C. to give a clear solution. Acetonitrile was removed on a rotary evaporator. The residue was purified by column chromatography (silica gel, 20% methanol-dichloromethane) and fractions with R$_f$=0.3 were collected. After the solvent was removed, the resultant thick oil was recrystallized from acetonitrile to afford a slightly yellow solid. Yield: 0.15 g (43%). mp: 148°–150° C. HPLC (8 micron C$_{18}$ column, linear gradient with 1% per min increase of solvent B) showed a peak with retention time of 22.5 min. The purity of this peak is 97.3% at 230 nm and 99.4 at 254 nm. Solvent A: 0.01% TFA in water, B: 0.01% TFA in acetonitrile. MS: 443 (M+H)$^+$. $^1$H NMR (DMSO-d$_6$), ε 1.12 [s, 12H, C (CH$_3$)$_2$], 1.70 (s, 3H, N=CCH$_3$), 2.35 (b, 1H, NHCH$_2$CH$_2$O), 3.52 (t, 2H, NHCH$_2$CH$_2$O), 3.98 (d, 2H, N=CCH$_2$NHCO), 4.14 (b, 2H, NHCH$_2$CH$_2$O), 5.10 (s, 2H, COCH$_2$), 6.46 (b, 1H, CH$_2$CH$_2$ONH), 7.14 and 7.60 (s, 2H, imidazolyl-H), 10.45 and 11.06 (s, 2H, NOH). Anal. Calcd. for C$_{17}$H$_{30}$N$_8$O$_6$: Calcd: C, 46.15; H, 6.83; N, 25.32. Found: C, 46.11; H, 6.85; N, 25.38.

EXAMPLE 14

Synthesis of 1-[2-hydroxy-3-(2-nitro-1H-imidazol-1-yl) propoxy]-3,3,9,9-tetramethyl-5-oxa-4,8-diaza-2,10-undecanedione, dioxime

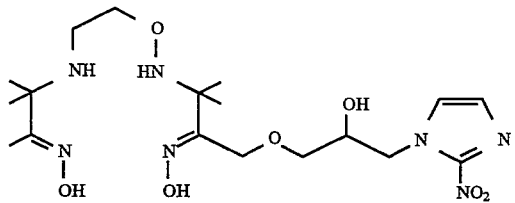

A. Preparation of 3,3-dimethylallylglycidyl ether

To a solution of 3,3-dimethylallyl alcohol (17.3 g, 20.5 mL, 0.2 mol) in dry tetrahydrofuran (THF) (200 mL) was added sodium hydride (4.8 g, 0.2 mol) in portions and the mixture was stirred at room temperature for 1 hr. Epibromohydrin (27.4 g, 17.12 mL, 0.2 mol) was added dropwise and the reaction mixture was stirred at room temperature for 24 hrs. THF was removed on a rotary evaporator and the residue was taken up in ether and filtered. The ether solution was concentrated on a rotary evaporator and the brown oil obtained was distilled under vacuum. bp: 93°–94° C./10 mm. Yield: 17.2 g (60.5%). $^1$H NMR (CDCl$_3$) ε 1.68 and 1.75 (s, 6H, CH$_3$), 2.61 and 2.88 (dd, 2H, oxirane CH$_2$), 3.17 (m, 1H, oxirane CH), 3.38 and 3.7 (m, 2H, CH$_2$OCH$_2$CH), 4.05 (m, 2H, CH$_2$OCH$_2$CH), 5.35 (m, 1H, >C=CH).

B. Preparation of 1-[2-hydroxy-3-(2-nitro-1H-imidazol-1-yl)propyldimethylallyl ether To a mixture of 3,3-dimethylallylglycidyl ether (9.0 g, 0.063 mol) and 2-nitroimidazole (7.2 g, 0.063 mol) in ethanol (75 mL), was added potassium carbonate (0.75 g, 0.005 mol) and the mixture was refluxed in an oil bath for 4 hrs. The reaction mixture was cooled and poured into water. The yellow solid formed was filtered and recrystallized from aqueous ethanol. Yield: 12.2 g (76%). mp: 72°–73° C. $^1$H NMR (CDCl$_3$) ε 1.62 and 1.78 (s, 6H, CH$_3$), 2.78 (d, 1H, OH), 3.4 and 3.58 (m, 2H, CHOHCH$_2$O), 4.0 (d, 1H, CHOH), 4.40 and 4.68 (m, 2H, CHOHCH$_2$N), 5.35 (m, 1H, >C=CH), 7.1 and 7.3 (s, 2H, imiH). Anal. Calcd. for C$_{18}$H$_{17}$N$_3$O$_4$: Calcd: C, 51.76; H, 7.71; N, 16.46. Found: C, 51.60; H, 6.48; N, 16.42.

C. Preparation of 3-chloro-1-(2-hydroxy-3-(2-nitro-1H-imidazol-1-yl)propoxy]-3-methyl-2-nitrosobutane To a cooled (0°–5° C.) stirred slurry of 1-[2-hydroxy-3-(2-nitro-1H-imidazol-1-yl)propyldimethylallyl ether (7.0 g, 0.0275 mol) in isoamyl nitrite (43 g, 50 mL, 0.042 mol) was added concentrated hydrochloric acid (2.5 mL, 0.03 mol) with stirring. The reaction mixture was maintained below 5° C. during the addition and stirred at 5° C. for an additional 2 hrs. The solid formed was stirred with cold ether-ethanol (3:1, 150 mL), filtered, and dried under vacuum. Yield: 5.8 g (67%). mp: 116°–117° C. dec. $^1$H NMR (DMSO) ε 1.55 and 1.62 (s, 6H, CH$_3$), 3.35 (m, 4H, CH$_2$OCH$_2$CHOH), 3.82 (m, 1H, CHOH), 4.1–4.52 (m, 2H, CHOHCH$_2$N<), 5.3 (m, 1H, CHOH), 6.0 (dd, 1H, CHNO), 7.15 and 7.42 (s, 2H, imi H).

D. Preparation of 3-[2-N-t-Boc amino ethoxy]amino-1-[2-hydroxy-3-(2-nitro-1H-imidazol- 1-yl)propoxy]-3-methyl-2-butanone oxime A solution of 2-(aminoxy)-1-t-Boc-aminoethane (1.76 g, 0.01 mol, Example 7(C)) and diisopropylethylamine (1.55 g, 0.012 mol) in acetonitrile (10 mL) was added to a slurry of 3-chloro-1-[2-hydroxy-3-(2-nitro-1H-imidazol-1-yl) propoxy]-3-methyl-2-nitrosobutane (3.2 g) in acetonitrile (50 mL) and the mixture was stirred at room temperature for 48 hrs. Acetonitrile was removed on a rotary evaporator and the thick viscous oil obtained was chromatographed over silica gel (hexane-ethyl acetate, 1:9). UV-visible fractions were collected and evaporated to give the title product as a thick oil. This was used in the next step without further purification. $^1$H NMR (CDCl$_3$) ε 1.29 (s, 6H, CH$_3$), 1.41 (s, 9H, t-Boc), 3.62 (m, 4H, CH$_2$OCH$_2$), 4.15 (NHCH$_2$CH$_2$O and CHOH), 5.0 (bs, 1H, NHBoc), 7.1 and 7.27 (s, 2H, imi H), 8.82 (s, 1H, NOH). MS: (M+H)$^+$=461.

E. Preparation of 1-[2-hydroxy-3-(2-nitro-1H-imidazol-1-yl)propoxy]-3,3,9,9-tetramethyl-5-oxa-4,8-diaza-2,10-undecanedione, dioxime 3-[2-N-t-Boc amino ethoxy]amino-1-[2-hydroxy-3-(2-nitro-1H-imidazol-1-yl)propoxy]-3-methyl-2-butanone oxime (3.8 g) was treated with methanolic HCl (20.0 mL) and stirred at room temperature for 2 hrs. Dry ether (250 mL) was added to the reaction mixture and the hydrochloride salt that formed was filtered and air dried. Yield: 3.9 g.

Diisopropylethylamine (3.9 g, 0.03 mol) was added to a slurry of the above hydrochloride salt (3.9 g, 0.008 mol) suspended in acetonitrile (50 mL) and the reaction was stirred at room temperature for 30 min. 3-Chloro-3-methyl-2-nitrosobutane (1.35 g, 0.01 mol, Example 10(C)) was added to the acetonitrile solution and the mixture was stirred at room temperature for 36 hrs. Acetonitrile was removed on a rotary evaporator and the residue was basified with potassium carbonate solution. The light green oil obtained was purified by column chromatography (silica gel, CH$_2$Cl$_2$: CH$_3$OH, 8:2). Fractions containing the product were collected and evaporated to give an oil, which was dried under vacuum to afford a light yellow oil. Yield: 1.12 g (30%). The oil obtained was dissolved in acetonitrile and left at room temperature for 4 hrs. The solid that formed was filtered and recrystallized from acetonitrile. Yield: 0.87 g (24%). mp: 156°–157° C. $^1$H NMR (DMSO) ε 1.08 and 1.18 [s, 12H, C(CH$_3$)$_2$], 1.67 (s, 3H, CH$_3$), 2.32 (m, 2H, NHCH$_2$CH$_2$ONH), 3.3–3.35 (m, 4H, CH$_2$OCH$_2$CHOH), 3.9 (m, 2H, OCH$_2$CHOH), 4.22 and 4.6 (m, 3H, CHOHCH$_2$N<), 7.15 and 7.56 (s, 2H, imi H), 10.4 and 10.93 (s, 2H, NOH). Anal. Calcd. for C$_{18}$H$_{33}$N$_7$O$_7$: Calcd.: C, 47.05; H, 7.24; N, 21.34. Found: C, 47.28; H, 7.24; N, 21.48.

EXAMPLE 15

Preparation of $^{99m}$Tc complexes (Method 1)

The following general procedure was used to prepare the four $^{99m}$Tc complexes below:

$^{99m}$Tc-complex prepared using the ligand from Example 7;

$^{99m}$Tc-complex prepared using the ligand from Example 8;

$^{99m}$Tc-complex prepared using the ligand from Example 9; and $^{99m}$Tc-complex prepared using the ligand from Example 14.

Ligand (2–4 mg) was dissolved in ethanol (0.1–0.2 mL) and 0.9% sodium chloride solution (1–2 mL) in a 5 mL glass vial. Sodium hydrogen carbonate buffer (0.1M NaHCO$_3$, 0.5 mL), and eluant from a $^{99}$Mo/$^{99m}$Tc generator (0.2–0.5 mL) were added. The vial was sealed, and a saturated solution of stannous tartrate in saline (50 μL) was added. The vial was shaken to mix the reagents, and allowed to stand at room temperature. The radiochemical purity (RCP) of the $^{99m}$Tc complexes was measured by reversed phase HPLC (high pressure liquid chromatography), using a 10 micron, 15 cm reversed phase PRP-1 column (Hamilton) that was eluted with 65/35 acetonitrile/0.1M NH$_4$OAc (pH 4.6). All technetium complexes had an RCP greater than 90% after 3 min., except for the complex of the ligand of Example 9 (Tc-5-oxa-PnAO-1-2-nitro) (which had an initial RCP of 82–89%) and the complex of the ligand of Example 8 (Tc-5-oxa-11-2-nitro), which had an initial RCP of 82–96%.

The complexes thus formed had the names:

Oxo[3,3,9,9-tetramethyl-5-oxa-4,8-diaza-2,10-undecanedione dioximato](3-)-N,N',N", N"']technetium-$^{99m}$Tc(V);

Oxo[[11-(2-nitro-1H-imidazol-1-yl)-3,3,9,9-tetramethyl-5-oxa-4,8-diaza-2,10-undecanedione dioximato](3-)-N,N', N",N"']technetium-$^{99m}$Tc(V);

Oxo[[1-(2-nitro-1H-imidazol-1-yl)-3,3,9,9-tetramethyl-5-oxa-4,8-diaza-2,10-undecanedione dioximato](3-)-N,N', N",N"']technetium-$^{99m}$Tc(V); and Oxo[[1-[2-hydroxy-3-(2-nitro-1H-imidazol-1-yl) propoxy]-3,3,9,9-tetramethyl-5-oxa-4,8-diaza-2,10-undecanedione dioximato](3-)-N,N',N", N"']technetium-$^{99m}$Tc(V).

EXAMPLE 16

Preparation of $^{99m}$Tc complexes (Method 2)

The following general procedure was used to prepare the six $^{99m}$Tc complexes below:

$^{99m}$Tc-complex prepared from the ligand from Example 9;

$^{99m}$Tc-complex prepared from the ligand from Example 10;

$^{99m}$Tc-complex prepared from the ligand from Example 11;

$^{99m}$Tc-complex prepared from the ligand from Example 12;

$^{99m}$Tc-complex prepared from the ligand from Example 13; and $^{99m}$Tc-complex prepared from the ligand from Example 14.

Ligand (2–4 mg) was dissolved in 0.1M HCl (0.1 mL) and 0.9% sodium chloride solution (1.0 mL) in a 5 mL glass vial, and 0.1M sodium hydrogen carbonate buffer (0.5 mL), saline, and $^{99}$Mo/$^{99m}$Tc generator eluate (total saline/eluate volume=0.5 mL) were added. The vial was sealed, and a saturated solution of stannous tartrate in saline (50 μL) was added. The vial was shaken to mix the reagents, and allowed to stand at room temperature. The radiochemical purities (RCP) of the $^{99m}$Tc complexes were measured by reversed phase HPLC (high pressure liquid chromatography), using a 10 micron, 15 cm reversed phase PRP-1 column (Hamilton) that was eluted with 65/35 acetonitrile/0.1M NH$_4$OAc (pH 4.6). All technetium complexes had an RCP greater than 90% within 3 min.

The complexes thus formed had the names:

Oxo[1-(2-nitro-1H-imidazol-1-yl)-3,3,9,9-tetramethyl-5-oxa-4,8-diaza-2,10-undecanedione dioximato](3-)-N,N', N",N"']technetium-$^{99m}$Tc(V);

Oxo[[12-(2-nitro-1H-imidazol-1-yl)-3,3,9,9-tetramethyl-7-oxa-4,8-diaza-2,10-dodecanedione dioximato](3-)-N,N', N",N"']technetium-$^{99m}$Tc(V);

Oxo[[12-[2-nitro-1H-imidazol-1-yl]-3,3,9,9-tetramethyl-5-oxa-4,8-diaza-2,10-dodecanedione dioximato](3-)-N,N', N",N"']technetium-$^{99m}$Tc(V);

Oxo[[1,13-bis(2-nitro-1H-imidazol-1-yl)-4,4,10,10-tetramethyl-6-oxa-5,9-diaza-3,11-tridecanedione dioximato](3-)-N,N',N", N"']technetium-$^{99m}$Tc(V);

Oxo[[1-[[(2-nitro-1H-imidazol-1-yl)acetyl]amino]-3,3,9, 9-tetramethyl-5-oxa-4,8-diaza-2,10-undecanedione dioximato](3-)-N,N',N",N"']-technetium(V)-$^{99m}$Tc; and Oxo[[1-[2-hydroxy-3-(2-nitro-1H-imidazol-1-yl) propoxy]-3,3,9,9-tetramethyl-5-oxa-4,8-diaza-2,10-undecanedione dioximato](3-)-N,N',N",N"']-technetium (V)-$^{99m}$Tc.

EXAMPLE 17

Preparation of Oxo[1-(2-nitro-1H-imidazol-1-yl)-3,3,9,9-tetramethyl-5-oxa-4,8-diaza-2,10-undecanedione, dioximato](3-)-N,N'N",N"']technetium-$^{99}$Tc(V)

To a stirring solution of (tetrabutylammonium)[TcOCl$_4$] (43.8 mg, 0.088 mmol) in 1 mL of methanol was added 50 μL of ethylene glycol and 0.54 mL of 0.75M sodium acetate solution in methanol. The ligand of Example 9 (33.8 mg, 0.088 mmol) dissolved in methanol (7.5 mL) was added. The resulting bright red-orange solution was evaporated to a red oil under a stream of nitrogen, re-dissolved in 5 mL of chloroform, and filtered to remove white solids. The solution was taken to dryness by rotary evaporation, re-dissolved in dichloromethane and purified on a silica gel column that was conditioned with 90:10 CH$_2$Cl$_2$:MeOH, and eluted with CH$_2$Cl$_2$. The first red band was collected, treated with an equal volume of hexane and allowed to go to dryness. The resulting red-orange crystalline solid was pure by HPLC.

EXAMPLE 18

Preparation of Oxo[[12-[2-nitro-1H-imidazol-1-yl]-3,3,9, 9-tetramethyl-7-oxa-4,8-diaza-2,10-dodecanedione, dioximato](3-)-N,N',N", N"']technetium-$^{99}$Tc(V)

To a stirring solution of [tetrabutylammonium]TcOCl$_4$ (73.7 mg, 0.148 mmoles) dissolved in 1.0 mL methanol was added 150 μL neat ethylene glycol (21.9 mmoles), followed by 1.5 mL of 0.75M sodium acetate in methanol. The ligand of Example 10 (70.2 mg, 0.176 mmoles) was added, causing the solution to turn clear red-orange. After 15 min the reaction was stripped to a viscous, red-orange, opaque oil by rotary evaporation, re-dissolved in dichloromethane (3 mL), and washed with $H_2O$ (2×10 mL) to remove water-soluble white solids. The dichloromethane solution was dried over anhydrous sodium sulfate, filtered, and taken to dryness by rotary evaporation. The bright red residue was re-dissolved in dichloromethane (1.0 mL), and purified on a silica gel column that was conditioned with 50:50 $CH_2Cl_2$/acetonitrile. The red band was collected, filtered, and taken to dryness by rotary evaporation. The product was re-dissolved in 0.75 mL dichloromethane and recrystallized by addition of hexane (2.5 mL). A bright red, crystalline solid was isolated by suction filtration, washed with hexane, and dried under vacuum. The title product obtained (40.0 mg; 44% yield) was pure by HPLC. Anal. Calc'd. for $C_{16}H_{25}N_7O_6Tc(.½H_2O)$ Calc'd: C, 37.00; H, 5.24; N, 18.88 Found: C, 37.03; H, 5.13; N, 18.60

EXAMPLE 19

Synthesis of 1-Hydroxy-3,3,9,9-tetramethyl-12-(2-nitro-1H-imidazol-1-yl)-7-oxa-4,8-diazadodecane-2,10-dione dioxime

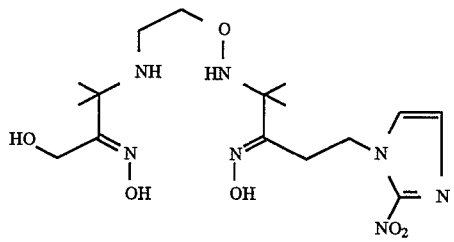

A. Preparation of 3-Chloro-1-hydroxy-3-methyl-2-butanone oxime

3-Methyl-2-buten-1-ol (8.6 g, 100 mmol) was mixed with isoamyl nitrite (28 g, 240 mmol) at room temperature. The solution was cooled to −5° C. in an ice-salt bath and concentrated HCl (11 mL, 100 mmol) was added dropwise. The reaction temperature was maintained between −5° to 0° C. during the addition. The reaction mixture was stirred in the ice-salt bath for 60 min, filtered and washed with cooled ether to give a white solid. Yield 4.5 g (30%). top: 114°–115° C. MS (m/z): 305 (2M+2+H)$^+$, 303 (2M+H)$^+$, 154(M+2+H)$^+$, 152 (M+H)$^+$. $^1$H NMR (DMSO-$d_6$): ε 1.56 (d) and 1.80 (s) [6H, $(CH_3)_2$CCHNO and $(CH_3)_2$CC=NOH)], 4.10 (m) and 4.26 (s) [2H, $HOCH_2$CH(NO) and $HOCH_2$C=NOH], 5.2 (b, 1H, $HOCH_2$), 5.93 (t) and 11.28 (b) [1H, CHN=O and C=NOH]. $^{13}$C (DMSO-$d_6$) ε 29.9 [$(CH_3)_2$CCHNO], 31.5 [$(CH_3)_2$CC=NOH], 53.7 [$(CH_3)_2$CCHNO], 59.7 [$(CH_3)_2$CC=NOH], 69.4 [$HOCH_2$CH (NO)], 74.1 [$HOCH_2$C=NOH], 160.2 [CHN=O and C=NOH]. Anal. Calcd. for $C_5H_{10}NClO$: C, 39.62; H, 6.65; N, 9.24; Cl, 23.39; O, 21.11. Found: C, 39.73; H, 6.87; N, 9.15; Cl, 23.43.

B. Preparation of 1-Hydroxy-3,3,9,9-tetramethyl-12-(2-nitro-1H-imidazol-1-yl)-7-oxa-4,8-diazadodecane-2,10-dione dioxime 8-t-Boc-amino-5-aza-4,4-dimethyl-1-(2-nitro-1H-imidazol-1-yl)-6-oxaoctan-3-one oxime (Example 10(B), 1.2 g, 3 mmol) was stirred with methanolic HCl (10 mL) at room temperature for 1 h to give a white suspension. Volatiles were evaporated on a rotary evaporator, and then under vacuum to give 8-amino-5-aza-4,4-dimethyl-1-(2-nitro-1H-imidazol-1-yl)-6-oxaoctan-3-one oxime hydrochloride as a white solid. $^1$H NMR ($D_2O$) ε 1.34 [s, 6H, $C(CH_3)_2$], 2.87 (t, 2H, $NHCH_2CH_2O$), 3.27 (t, 2H, $CH_2CH_2$-nitroimidazolyl), 4.28 (t, 2H, $NHCH_2CH_2O$), 4.68 (t, 2H, $CH_2CH_2$-nitroimidazolyl), 7.07 and 7.34 (s, 2H, nitroimidazolyl-H)].

8-Amino-5-aza-4,4-dimethyl-1-(2-nitro-1H-imidazol-1-yl)-6-oxaoctan-3-one oxime hydrochloride was suspended in acetonitrile (20 mL) and cooled in an ice bath for 15 min. N,N-diisopropylethylamine (2.0 g, 15.5 mmol) was added to the cooled suspension followed by 3-chloro-1-hydroxy-3-methyl-2-butanone oxime (0.54 g, 3.6 mmol) and the mixture was stirred under $N_2$ atmosphere at room temperature for 4 h to give a clear solution. Acetonitrile was evaporated on a rotary evaporator. TLC (silica gel, 5% methanol-ethyl acetate) of the crude product showed one major spot with $R_f$=0.5). HPLC showed one major peak with retention time of 22.1 min. The residue was treated with $K_2CO_3$ solution. The basic reaction mixture was extracted with ethyl acetate (3×45 mL) and the organic layer was dried and evaporated on a rotary evaporator. The gummy residue obtained was applied to a column (silica gel, ethyl acetate) and eluted with ethyl acetate (400 mL) and 5% methanol-ethyl acetate. Fractions with the product were combined and evaporated to yield a thick oil. TLC (silica gel, 5% methanol-ethyl acetate) of the product showed one spot with tailing. This oil was further purified by recrystallization from acetonitrile to afford a white solid, 0.57 g (47.5%). mp 127°–129° C. HRMS calculated for $C_{16}H_{30}N_7O_6$:(M+H)$^+$=416.2255. Found: 416.2258. $^1$H NMR (DMSO-$d_6$): ε 1.11 [s, 6H, $CH_2HNC(CH_3)_2$], 1.24 (s, 6H, $OHNC(CH_3)_2$), 2.82 (t, 2H, $NHCH_2CH_2O$), 3.34 (t, 2H, $CH_2CH_2$-nitroimidazolyl), 3.66 (t, 2H, $NHCH_2CH_2O$), 4.34 (s, 2H, $CH_2OH$), 4.58 (t, 2H, $CH_2CH_2$-nitroimidazolyl), 6.56 (s, 1H, $CH_2CH_2ONH$), 7.14 and 7.54 (s, 2H, imidazolyl-H), 10.78 (s, 2H, HON=C). Anal. calculated for $C_{16}H_{29}N_7O_6$: C, 46.26; H, 7.04; N, 23.46; O, 23.11. Found: C, 46.16; H, 7.01; N, 23.29.

EXAMPLE 20

Synthesis of 3,3,9,9-Tetramethyl-6-[(2-nitro-1H-imidazol-1-yl)methyl]-5-oxa-4,8-diazaundecane-2,10-dione dioxime

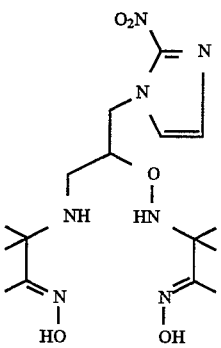

A. Preparation of 1-(3-Phthalimido-2-hydroxy propyl)-2-nitroimidazole

To a solution of N-(2,3-epoxypropyl)phthalimide (commercially available, 20.3 g, 0.1 mol) in ethanol (200 mL), 2-nitroimidazole (11.3 g, 0.1 mol) and potassium carbonate (1.2 g) were added and the reaction mixture was refluxed for 6 hrs. The reaction mixture was cooled and poured into water (700 ml) and the yellow solid formed was filtered and dried. Yield 28.2 g) 89%). It was recrystallized from methanol. mp. 213°–214° C. $^1$H NMR (DMSO) ε 3.62 (m, 4H, PhthNCH$_2$CHOH), 4.08 (m, 1H, CHOH), 4.32 and 4.63 (m, 2H, CHOHCH$_2$N<), 5.54 (d, 1H, CHOH), 7.15 and 7.68 (s, 2H, imiH), 7.8 (m, 4H, ArH). MS: (M+H)$^+$=317$^+$ Anal. Calcd. for C$_{14}$H$_{12}$N$_4$O$_5$: C, 53.17; H, 3.82; N, 17.71. Found C, 53.11; H, 3.76; N, 17.49.

B. Preparation of 1-(3-N-t-Boc amino-2-hydroxy propyl)-2-nitroimidazole

To a suspension of 1-(3-phthalimido-2-hydroxypropyl)-2-nitroimidazole (28.0 g, 0.09 mol) in methanol (250 mL) was added hydrazine (3.2 g, 0.1 mol), and the mixture was refluxed for 6 hrs. The reaction mixture was cooled and the methanol was removed on a rotary evaporator. The mixture of the amino hydrin and the hydrazide was dissolved in a solution of sodium carbonate (21.2 g, 0.2 mol) in water (200 mL). Dioxane (400 mL) was added to this mixture and cooled to 0° C. Ditertiarybutyl dicarbonate (21.8 g, 0.1 mol) was added to this mixture and stirred at 0° C. for 1 hr and room temperature for 12 hrs. Dioxane-water was removed on a rotary evaporator and the residue was extracted with ethyl acetate (3×150 mL). Ethyl acetate layer was washed with water, dried (Na$_2$SO$_4$) and evaporated on a rotary evaporator to yield the title compound as a yellow solid. Yield 19.2 g. (76%). It was recrystallized from hexane-ethyl acetate. mp. 128°–129° C. $^1$H NMR (DMSO) ε 1.39 (s, 9H, NHBoc), 2.92 (m, 2H, BocHNCH$_2$CHOH), 3.75 (m, 1H, CHOH), 4.14 and 4.55 (m, 2H, CHOHCH$_2$N<), 5.25 (d, 1H, CHOH), 6.94 (m, 1H, BocHN) 7.15 and 7.59 (s, 2H, imiH). Anal. Calcd. for C$_{11}$H$_{18}$N$_4$O$_5$: C, 46.15; H, 6.34; N, 19.57. Found C, 46.37; H, 6.41; N, 19.39.

C. Preparation of 1-(3-N-t-Boc amino-2-phthalimidooxypropyl)-2-nitroimidazole

N-hydroxyphthalimide (3.36 g, 0.02 mol), 1-(3-N-t-Boc amino-2-hydroxypropyl)-2-nitroimidazole and triphenylphosphine (5.25 g, 0.02 mol) were dissolved in THF (100 mL), and treated with diethyl azodicarboxylate (3.83 g, 0.022 mol). The reaction mixture became dark red and the color disappeared after a few minutes. A slight exothermic reaction was observed during the addition of diethyl azodicarboxylate. The reaction mixture was stirred at room temperature for 24 h and evaporated on a rotary evaporator to dryness. The residue was chromatographed over silica gel, using hexane ethyl acetate (7:3, 6:4) as eluent. Evaporation of the solvent afforded the title compound as a foamy solid. Yield: 2.8 g. MS: (M+H)$^+$=432$^+$.

D. Preparation of 2-aminoxy-3-(2-nitro-1H-imidazol-1-yl)-1-aminopropane dihydro chloride Hydrazine (98%, 0.5 g, 0.016 mole) was added to a solution of 1-(3-N-t-Boc amino-2-phthalimidooxypropyl)-2-nitroimidazole (3.31 g, 0.01 mole) in ethanol (50 mL) and the mixture was refluxed for 2 hrs. The solid which formed was filtered and the filtrate was evaporated on a rotary evaporator. The thick oil obtained was triturated with ethyl acetate and the resultant precipitate was removed by filtration. The ethyl acetate solution was evaporated on a rotary evaporator to give 2-aminoxy-3-(2-nitro-1H-imidazol-1-yl)-1-t-Boc aminopropane as an oil. Yield: 2.3 g. $^1$H NMR (CDCl$_3$) ε 1.46 (s, 9H, NHBoc), 3.40 (m, 2H, BocHNCH$_2$CHO), 3.82 (m, 1H, CHONH$_2$), 4.4 and 4.62 (m, 2H, CHOHCH$_2$N<), 4.9 (bs, 1H, NHtBoc), 5.2 (bs, 2H, NH$_2$), 7.15 and 7.27 (s, 2H, imiH).

Methanolic HCl (10 mL) was added to a solution of 2-aminoxy-3-(2-nitro-1H-imidazol-1-yl)-1-t-Boc aminopropane (3.01 g, 0.1 mol) in methanol (15 mL), and the mixture was stirred at room temperature for 20 min. Ether (150 mL) was added to the methanolic solution and the 2-aminoxy-3-(2-nitro-1H-imidazol-1-yl)-1-aminopropane dihydrochloride which formed was filtered and dried under vacuum. This was used in the next step without further purification. Yield 2.6 g (95%). MS: (M+H)$^+$=202.

E. Preparation of 3,3,9,9-Tetramethyl-6-[(2-nitro-1H-imidazol-1-yl)methyl]-5-oxa-4,8-diazaundecane-2,10-dione dioxime 3-Chloro-3-methyl-2-nitrosobutane (1.45 g, 0.011 mol) was added to a mixture of 2-aminoxy-3-(2-nitro-1H-imidazol-1-yl)-1-aminopropane dihydrochloride (1.36 g, 0.005 mol) and diisopropylethylamine (1.4 g, 0.011 mol) in acetonitrile (15 mL), and the mixture was stirred at room temperature for 12 hrs. Acetonitrile was removed on a rotary evaporator and the thick oil obtained was basified with potassium carbonate solution. The light green oil obtained was extracted with ethyl acetate and dried (Na$_2$SO$_4$). Ethyl acetate was removed on a rotary evaporator and oil obtained was purified by column chromatography (silica gel, CH$_2$Cl$_2$: CH$_3$OH, 9:1). Fractions containing the product were collected and evaporated to give a colorless oil, which was dried under vacuum to afford a foamy solid. The solid obtained was dissolved in acetonitrile and left at room temperature for 2 hrs. The solid that formed was filtered and recrystallized from acetonitrile. Yield: 0.82 g (20%). mp. 170°–171° C. $^1$H NMR (DMSO): ε 0.96 and 1.11 [s, 12H, C(CH$_3$)$_2$], 1.65 (s, 6H, CH$_3$), 2.30 (m, 2H, HNCH$_2$CHOH), 3.80 (m, 1H, CHO), 4.5 (m, 2H, CHOHCH$_2$N<), 7.15 and 7.59 (s, 2H, imiH) 10.43 (s, 2H, NOH). MS:(M+H)$^+$=400. Anal. Calcd. for C$_{16}$H$_{29}$N$_7$O$_5$: C, 48.11; H, 7.32; N, 24.55. Found C, 48.63; H, 7.39; N, 24.38.

EXAMPLE 21

Synthesis of 4,4,10,10-Tetramethyl-1,13-bis(2-nitro-1H-imidazol-1-yl)-7-[(2-nitro-1H-imidazol-1-yl)methyl]-6-oxa-5,9-diazatridecane-3,11-dione, dioxime

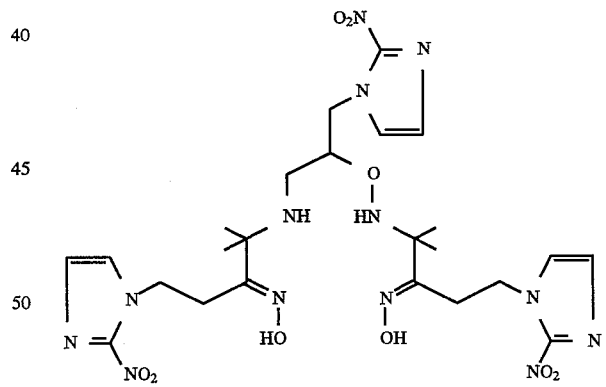

Diisopropylethylamine (0.55 g, 0.042 mol) was added to a suspension of 2-aminoxy-3-(2-nitro-1H-imidazol-1-yl)-1-aminopropane dihydrochloride (0.55 g, 0.002 mol) in acetonitrile (5 mL) and the mixture was stirred at room temperature for 10 min. 4-Chloro-4-methyl-1-(2-nitro-1H-imidazol-1-yl)-3-nitrosopentane (1.1 g, 0.0042 mol) (Example 10(A)) was added to the acetonitrile solution and the mixture was stirred at room temperature under nitrogen for 24 hrs. Acetonitrile was removed on a rotary evaporator to give a viscous oil which was basified with potassium carbonate. The mixture was extracted with ethyl acetate and the ethyl acetate solution was dried with sodium sulfate. Removal of ethyl acetate gave a thick oil which was purified by column chromatography (silica gel, CH₂Cl₂:CH₃OH, 9:1). Elution with CH₂Cl₂:CH₃OH (9:1) gave the title compound as a thick oil which was dried under vacuum. The solid that formed was recrystallized from acetonitrile. mp 136°–137° C. Yield: 0.32 g (25%). $^1$H NMR (DMSO) ε 0.89 and 1.09 [s, 12H, C(CH₃)₂], 2.42 (m, 2H, HNCH₂CHO), 3.72 (m, 1H, CHO), 4.5 (m, 6H, CH₂CH₂N< and CHOHCH₂N<), 7.10, 7.16 and 7.59 (s, 6H, imiH) 10.43 (s, 2H, NOH). MS:(M+H)⁺=650. Anal. Calcd. for C₂₄H₃₅N₁₃O₉: C, 44.37; H, 5.43; N, 28.03. Found C, 44.54; H, 5.43; N, 27.93.

EXAMPLE 22

Synthesis of 1,13-bis(2-nitro-1H-imidazol-1-yl)-4,4,10,10-tetramethyl-6-oxa-7-(hydroxymethyl)-5,9-diaza-3,11-dodecanedione dioxime

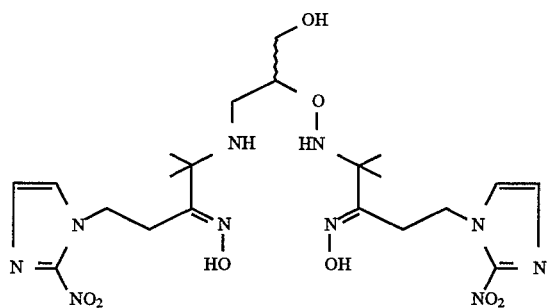

A. Preparation of 5-hydroxy-2-phenyl-1,3-dioxane

To a solution of benzaldehyde (150.0 g, 1.41 mol) in toluene, glycerol (160.0 g, 1.74 mol) was added followed by 4-methylbenzenesulfonic acid (1.0 g) and the mixture was vigorously stirred under reflux with a Dean-Stark water separator. The refluxing was continued until no more water separated in the condenser (6-8 h). The clear solution was treated with 4N NaOH until basic and the organic layer was washed with water (5×100 mL) followed by saturated sodium chloride solution and then dried over anhydrous sodium sulfate. Concentration of the organic layer resulted in an oil which was dissolved in hot isopropylether and then left in the freezer overnight. The colorless solid was filtered and washed with isopropylether to yield the title product as a colorless solid. Yield: 55.0 g (22%). m.p. 83°–84° C. [Lit. m.p. 83°– 84° C.; J. S. Briamacombe, A. B. Foster and M. Stacey, Chem. & Ind., 1958, 122814 9]. $^1$H NMR (CDCl₃) ε 3.1 (d, 1H, —OH), 3.7 (d, 1H Ar—CH), 4.3 (m, 4H, O—CH₂), 5.6 (s, 1H, O—CH—O) and 7.4 (m, 5H, Ar—H). M/e: [M+H]⁺=181.

B. Preparation of 2-phenyl-5-O-phthalimido-1,3-dioxane

To a solution of 5-hydroxy-2-phenyl-1,3-dioxane (55.0 g, 0.305 mole) and N-hydroxyphthalimide (54.75 g, 0.34 mole) in dry THF (100 mL), triphenylphosphine (94.42 g, 0.36 mole) was added and the solution was cooled to 0° C. in an ice-salt bath. Diethylazodicarboxylate (62.7 g, 0.36 mole) was added dropwise with stirring under nitrogen. After the addition, the reaction mixture was stirred overnight under nitrogen. The solid separated was filtered off and washed with ice cold THF. The combined THF solution was concentrated and the residue was again recrystallized from hot isopropylether to yield additional product as a colorless solid. Yield: 56.0 g (56.6%). m.p.=171°–172° C. $^1$H NMR (CDCl₃) ε 4.0 (dd appearing as t, 2H, O—CH₂ₐ), 4.25 (m, 3H, O—CH₂ᵦ and O—CH), 5.3 (s, 1H, O—CH—O), 7.3–8.0 (m, 9H, Ar—H). M/e: [M+H]⁺=326.

C. Preparation of 3-bromo-1-O-benzoyl-2-O-phthalimidopropane

A solution of 2-phenyl-5-O-phthalimido-1,3-dioxane (56.0 g, 0.172 mole) in CCl₄ (200 mL) was treated with N-bromosuccinimide (36.8 g, 0.206 mole), barium carbonate (41.44 g, 0.21 mole) and the mixture was vigorously stirred under nitrogen and reflux for 2 h. The reaction mixture was cooled and filtered through a pad of celite. The solid residue was thoroughly washed with carbon tetrachloride (5×50 mL) and the combined organic layer was washed with sodium bisulfite solution to remove any excess bromine present. The colorless organic layer was dried over anhydrous sodium sulfate and was concentrated to give a solid which was recrystallized from isopropylether to yield the title product as a colorless solid. Yield: 49.0 g (71%). m.p. 98°–99° C. $^1$H NMR (CDCl₃) ε 3.85 (m, 2H, Br—CH₂), 4.8 (m, 3H, O—CH₂ and O—CH) and 7.0–8.0 (m, 9H, Ar—H). M/e: [M+H]⁺=404, 406.

D. Preparation of 3-azido-2-O-(phthalimido)-1-O-(benzoyl)propane

A solution of 3-bromo-1-O-benzoyl-2-O-phthalimidopropane (49.0 g, 0.12 mol) in dry DMF (200 mL) was treated with NaN₃ (16.6 g, 0.26 mol) and sodium bicarbonate (24.0 g, 0.3 mol) and the mixture was stirred under nitrogen at 60°–65° C. for 20 h. The solvent was removed under reduced pressure to give a paste which was extracted with ethyl acetate. The ethyl acetate layer was dried (Na₂SO₄) and was concentrated to yield an oil. The oil was crystallized with hexanes/ether to provide the title product azide as a colorless solid. Yield: 38.0 g (87%). m.p.: 69°–70° C. $^1$H NMR (CDCl₃) ε 3.7 (m, 2H, N₃—CH₂), 4.7 (m, 3H, PhCOO—CH₂ and N—O—CH) and 7.4–8.2 (m, 9H, Ar—H). M/e: [M+H]⁺=367.

E. Preparation of 2-O-(amino)-3-azido-1-propanol

To a saturated solution of methanolic ammonia (50 mL), 3-azido-2-O-(phthalimido)-1-O(benzoyl)propane (11.6 g, 31.7 mmol) was added and stirred at room temperature for 20 h. The solid formed was filtered off and washed with methanol. The filtrate was concentrated and chromatographed over flash silica gel. Elution with 1:1 ethyl acetate/hexanes yielded the title product as a colorless oil. Yield: 3.25 g (78%). $^1$H NMR (CDCl₃) ε 2.9 (bs, 1H, —OH), 3.4 (d, 2H, N₃—CH₂), 3.9 (m, 3H, O—CH₂ and N—O—CH) and 5.6 (bs, 2H, O—NH₂). M/e: [M+H]⁺=133.

F. Preparation of 3-amino-2-O-(amino)-1-propanol, dihydrochloride salt

To a solution of 2-O-(amino)-3-azido-1-propanol (3.25 g, 24.6 mmol) in dry THF (20 mL), triphenylphosphine (7.86 g, 30 mmol) was added and stirred until the starting material disappeared on TLC (2 h). The organic phase was extracted with 2N HCl and the aqueous phase was extracted with dichloromethane (3×20 mL). The organic solution was discarded and the aqueous solution was concentrated under reduced pressure to give a colorless, very hygroscopic solid, which was taken to the next step without further purification. Yield: 4.15 g as dihydrochloride salt (95%). m.p.>200° C. (dec.). $^1$H NMR (D₂O) ε 3.2 (m, 2H, N—CH₂), 3.8 (m, 2H, O—CH₂) and 4.4 (m, 1H, N—O—CH). M/e: [M+H]⁺=107.

G. Preparation of 1,13-bis(2-nitro-1H-imidazol-1-yl)-4,4,10,10-tetramethyl-6-oxa-7-(hydroxymethyl)-5,9-diaza-3,11-dodecanedione dioxime To a solution of 3-amino-2-O-(amino)-1-propanol dihydrochloride (0.54 g, 3 mmol) in dry DMF (5 mL), diisopropylethylamine (6.3 g, 7 mmol) was added and stirred for ½ h. The formation of the amine hydrochloride could be observed after 15 min. Solid 4-chloro-4-methyl-1-(2-nitro- 1H-imidazol-1-yl)-3-nitrosopentane (2.45 g, 9.9 mmol, Example 10(A)) was added all at once followed by diisopropylethylamine (1.29 g, 10 mmol) and stirred at room temperature for ½ h. The solution was then warmed to 50° C. The reaction mixture became clear after 20 min. and was kept stirred at 50° C. for 1 h. Solvent DMF and other volatile impurities were removed under reduced pressure. The resulting gummy mass was dissolved in a minimum amount of water (5 mL) and treated with solid sodium carbonate until basic (pH=9–9.5). The solution was then extracted with ethyl acetate several times (5×25 mL). The combined organic layer was dried (anhydrous sodium sulfate) and then concentrated to give a yellow gum. The crude product was chromatographed over flash silica gel and elution with 9:1 dichloromethane/MeOH yielded the product as a semi-solid which was chromatographed two more times to yield a yellow solid (92–95% pure, HPLC). The solid was again dissolved in a minimum amount of AcCN and isopropylether was added dropwise until a precipitate was formed. The solid was filtered and washed with iosopropylether/AcCN (9:1) and dried under vacuum for several hours to yield the title product. Yield: 0.145 g (8.7%). m.p. Becomes a foam at 50° C. and melts with decomposition at 142°–144° C. $^1$H NMR (acetone-d$_6$) ε 1.15 (s, 6H, gem dimethyls), 1.2 (2s, 6H gem dimethyls) 2.8 (m, 2H , N—CH$_2$), 3.0 (m, 4H, N=C—CH$_2$), 3.8 (m, 3H, O—CH$_2$ and N—O—CH), 4.8 (m, 4H, imi-CH$_2$), 7.2 (d, 2H, imi-H) and 7.6 (d, 2H, imi-H). M/e: [M+H]$^+$=555. HPLC: RT 26.73 min. (0–35% AcN in water containing 0.1% TFA was used as the mobile phase; Dynamax 25×0.46 cm C-18 column was employed and the purity was checked at 230 nm). Anal. Calcd. for C$_{21}$H$_{34}$N$_{10}$O$_8$. H$_2$O (1.67): C, 43.14; H, 6.44; N, 23.96. Found: C, 43.53; H, 6.14; N, 23.57.

EXAMPLE 23

Synthesis of 12-(2-Nitro-1H-imidazol-1-yl)-3,3,9,9-tetramethyl-6-(hydroxymethyl)-7-oxa-4,8-diaza-2,10-dodecanedione dioxime

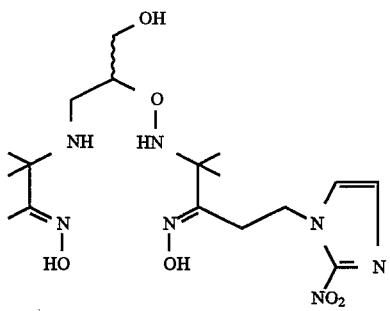

A. Preparation of 4-[[(2-Azido-1-(hydroxymethyl) ethoxy]amino]-4-methyl-1-( 2-nitro-1H-imidazol-1-yl)-3-pentanone, oxime To a solution of 2-O-(amino)-3-azido-1-propanol (1.2 g, 9 mmol, Example 22(E)) and diisopropylethylamine (1.55 g, 12 mmol) in dry AcCN (5 mL), solid 4-chloro-4-methyl-1-(2-nitro-1H-imidazol-1-yl)-3-nitrosopentane (2.34 g, 10 mmol, Example 10(A)) was added all at once and stirred at 60°–65° C. for 2 h. The solution was concentrated to a paste and the crude product was chromatographed over a flash silica gel column. Elution with 85:15 methylene chloride/methanol yielded the alkylated title product as a pale yellow gum. Yield: 2.7 g (54%). $^1$H NMR (CDCl$_3$) ε 1.3 (2s, 6H, gem dimethyls), 3.0 (t, 1H, exchangeble with D$_2$O, —OH), 3.5 (d, 2H, N$_3$—CH$_2$), 3.75 (m, 3H, O—CH$_2$ and O—CH), 4.8 (t, 2H, imid-CH$_2$), 5.85 (s, 1H, O—NH), 7.2 (s, 1H, imi-H), 7.3 (s, 1H, imi-H) and 9.2 (s, 1H, N—OH). M/e: [M+H]$^+$=357. The above product was taken to the next step without any further purification.

B. Preparation of 4-[[2-Amino-1-(hydroxymethyl ethoxy] amino -4-methyl-1-(2-nitro-1H-imidazol-1-yl)-3-pentanone, oxime To a solution of the azide title product of step A (2.7 g, 7.5 mmol) in dry THF (5 mL) triphenylphosphine (2.0 g, 8 mmol) was added and the solution was stirred for 1 h. TLC indicated that the azide was still present. The reaction mixture was then refluxed for 15 min, upon which the starting material totally disappeared on TLC. The solution was concentrated and diluted with 10 mL of water. The aqueous solution was repeatedly extracted with dichloromethane (5×15 mL) and the organic phase was discarded. The aqueous solution was filtered and then freeze dried to yield the title product amine as a pale yellow solid. A small amount was recrystallized from AcCN. Yield: 1.3 g (53%). m.p. 146°–147° C. $^1$H NMR (DMSO-d$_6$) ε 1.2 (s, 6H, gem dimethyls), 2.6 (m, 2H, H$_2$N—CH$_2$), 3.6 (m, 3H, O—CH$_2$ and —O—CH), 4.7 (t, 2H, imi-CH$_2$), 6.6 (bs, 1H, —O—NH), 7.2 (s, 1H, imi-H), 7.6 (s, 1H, imi-H) and 10.8 (bs, 1H, N—OH). M.S.: [M+H]$^+$=331.

C. Preparation of 12-(2-Nitro-1H-imidazol-1-yl)-3,3,9,9-tetramethyl-6-(hydroxymethyl)-7-oxa-4,8-diaza-2,10-dodecanedione dioxime To a suspension of the monoamine monooxime title product of step B (1.2 g, 3.6 mmol) in dry AcCN (5 mL), diisopropylethylamine (0.65 g, 5 mmol) was added and the solution was warmed up to 60°–65° C. and kept stirred. The solution became homogeneous at that point. To the above warm solution, 3-chloro-3-methyl-2-nitrosobutane (0.675 g, 5 mmol, Example 1(C)) was added all at once as a solid and the reaction mixture was stirred for 30 min at 60°–65° C. The reaction mixture was then concentrated to a paste and the crude product was adsorbed onto flash silica gel (10 g) and then loaded onto a flash silica gel column. Elution with 8:2 dichloromethane/methanol yielded the product as a pale yellow solid which was recrystallized from THF/isopropylether to furnish the title bisalkylated compound as a pale yellow solid. Yield: 0.35 g (23%). m.p. 118°–120° C. (dec.). $^1$H NMR (DMSO-d$_6$) ε 1.3 (bs, 6H, gem dimethyls), 1.8 (s, 3H, N=C—CH$_3$), 2.4 (m, 2H, N—CH$_2$), 3.0 (bt, 2H, N=C—CH$_2$), 3.5 (m, 3H, O—CH$_2$ and O—CH), 4.8 (bt, 2H, imi-CH$_2$), 6.8 (bs, 1H, O—NH), 7.3 (s, 1H, imi -H), 7.7 (s, 1H, imi-H), 10.6 (s, 1H, N—OH) and 10.9 (s, 1H, N—OH). M/e-[M+H]$^+$430. HPLC: RT (retention time) –23.7 min. (0–45% AcN in water with 0.1% TFA; C-18 Dynamax 25×0.46 cm column; detection at 230 nm). Anal. Calcd. for C$_{17}$H$_{31}$N$_7$O$_6$. 0.5H$_2$O, 0.1IPE: C, 47.11; H, 7.50; N, 21.85. Found: C, 47.12; H, 7.33; N, 21.74.

EXAMPLE 24

Synthesis of 3,3,9,9-Tetramethyl-6-[[3-(2-nitro-1H-imidazol-1-yl)propoxy]methyl]-5-oxa-4,8-diazaundecane-2,10-dione, dioxime

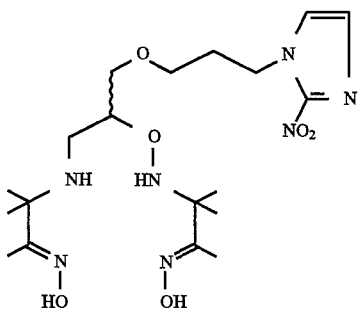

A. Preparation of 3-Bocamino-2-O-(N-bocamino)-1-propanol

To a solution of 3-amino-2-O-(amino)-1-propanol, dihydrochloride (2.0 g, 10.5 mmol, Example 22(F)) in water (25 mL), sodium carbonate solution was added until the pH reached about 10. Di-t-butyldicarbonate (5.6 g, 25 mmol) in dioxane (100 mL) was added to the above cooled solution of the diamine in water and the reaction mixture was stirred at room temperature for 24 h. All the volatiles were removed under reduced pressure and the paste was diluted with water (100 mL). The aqueous solution was extracted with ether (5×50 mL) and the combined organic layer was washed with water and dried (sodium sulfate). Evaporation of ether left behind a paste which was chromatographed on a flash silica gel column. Elution with 70:30 hexanes/ethyl acetate yielded the product as a colorless oil. The oil was crystallized from pentane/ether to furnish the bis bocamine title product as a colorless solid. Yield: 2.32 g (73%). m.p. 76°–77° C. $^1$H NMR (CDCl$_3$) ε 1.4 (2s, 18H, boc methyls), 3.2–3.5 (m, 2H, CH$_2$—NHBoc), 3.6–3.8 (m, 3H, O—CH$_2$, and OH), 4.2 (m, 1H, CH—ONHBoc), 5.2 (bt, 1H, NHBoc), and 7.6 (s, 1H, O—NHBoc). M/e: [M+H]$^+$=307.

B. Preparation of N-[(1,1-Dimethylethoxy)carbonyl]-2-[[(1,1-dimethylethoxy)carbonyl]amino]oxy]-3-[3-(2-nitro-1H-imidazol-1-yl)propyl]-propanamine To a solution of 3-bocamino-2-O-(N-bocamino)-1-propanol (2.2 g, 7.2 mmol) in dry DMF (10 mL), Cs$_2$CO$_3$ (2.6 g, 8 mmol) was added and the solution was warmed up to 60°–65° C. in an oil bath under nitrogen with stirring. To the warm solution, 3-bromo-1-(2-nitro-1H-imidazol-1-yl)propane (1.90 g, 8 mmol; D. C. Heimbrook, K. Shyam and A. C. Sartorelli, Anti-cancer Drug Design, 2, 339–350 (1988)) was added and stirring was continued for 16 h more. All the volatiles were removed under reduced pressure and the residue was chromatographed on flash silica gel. Elution with 7:3 EtOAc-Hexanes yielded the title product as a pale yellow gum. Yield: 1.32 g (40%). $^1$H NMR (CDCl$_3$) ε 1.5 (s, 9H, O—CMe$_3$), 1.6 (s, 9H, O—CMe$_3$), 2.2 (m, 2H, CH$_2$—CH$_2$—CH$_2$—O—), 3.3–3.8 (m, 7H, BocHN—CH$_2$, O—CH$_2$ and N—O—CH), 5.4 (bs, 1H, BocNH), 7.1 (s, 1H, imi-H) and 7.2 (s, 1H, imi-H). M/e: [M+H]$^+$=460.

C. Preparation of 3,3,9,9-Tetramethyl-6-[[3-(2-nitro-1H-imidazol-1-yl)propoxy]methyl]-5-oxa-4,8-diazaundecane-2,10-dione, dioxime The protected diaminoether title product of the above step B (1.7 g, 3.7 mmol) was dissolved in 5 mL of methanolic HCl and stirred at room temperature for 30 min. The solution was concentrated under vacuum to yield a yellow solid which was dissolved in 2 mL of water and cooled in ice. NaOH (2N) was added dropwise until the pH of the solution reached 10. The solution was frozen with a dry-acetone bath and freeze dried to yield a pale yellow solid whose HPLC showed only one peak under linear gradient conditions (t$_R$-11.89 min.). The solid was suspended in dry AcCN (2 mL) and diisopropylethylamine (1.03 g, 8 mmol) was added and stirred. 3-Chloro-3-methyl-2-nitrosobutane (1.08 g, 8 mmol, Example I(C)) was added as a solid all at once and stirred at 45° C. for 30 min. The crude reaction mixture was adsorbed on 5 g of flash silica gel and loaded onto a column. Elution with 2% MeOH in EtOAc yielded the product as a pale yellow solid. The solid was crystallized from hexane/isopropylether/MeOH. Yield: 0.025 g (1.4%). m.p. 158°–160° C. (dec.). $^1$H NMR (CD$_3$CN): ε 1.3 (2s, 12 H, C—CH$_3$), 1.9 (2s, 6H, N=C—C$_3$), 2.2 (m, imi-CH$_2$—CH$_2$—CH$_2$—O), 2.8 (bm, 2H, N—CH$_2$), 3.0 (bm, 3H, O—C$_H$ and O—CH$_2$), 3.8 (bt, 2H, O—CH$_2$), 4.6 (m, 2H, imi-CH$_2$), 7.2 (s, 1H, imi-H), 7.5 (s, 1H, imi-H) and 9.0 (bs, 2H, N—OH). M/e: [M+H]$^+$=458. HPLC: t$_R$-26.85 min (0–40% AcN in water with 0.1% TFA was used as a linear gradient; detection-230 nm; C$_{18}$ Dynamax 25×0.46 cm column was used). Anal: calcd. for 0.1M hex, 0.1M IPE, 0.9M H$_2$O; C, 49.26; H, 8.1; N, 19.9. Found: C, 49.40; H, 7.70; N, 19.59.

EXAMPLE 25

Synthesis of 1-Ethoxy-3,3,9,9-tetramethyl-12-(2-nitro-1H-imidazol-1-yl)-6-[(2-nitroimidazol-1-yl)methyl]-7-oxa-4,8-diazadodecane-2,10-dione dioxime

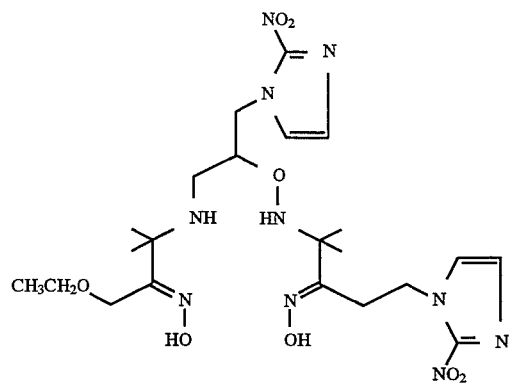

A. Preparation of 1-Ethoxy-3-methyl-2-butene

Freshly prepared silver oxide (101 g, 370 mmol) was added to a mixture of 3-methyl-2-buten-1-ol (21.0 g, 25 mL, 240 mmol) and ethyl iodide (300 mL) and stirred at 45° C. for 6 h. Silver salts were removed by filtration and the filter cake was washed with ether (2×150 mL). The filtrate and the washings were combined and the ether and excess ethyl iodide was removed by distillation. The oil obtained was distilled under atmospheric pressure to yield 14.8 g (51%) of 1-ethoxy-3-methyl-2-butene as a colorless liquid. b.p. 119°–120° C. $^1$H NMR (CDCl$_3$) ε 1.2 (t, 3H, CH$_2$CH$_3$), 1.72 (d, 6H, CH$_3$), 3.45 (m, 2H,CH$_2$CH$_3$), 3.95 (d, 2H, CH$_2$), 5.38 (t, 1H, (CH$_3$)$_2$C=CH—).

B. Preparation of 1-Ethoxy-3-chloro-3-methyl-2-nitrosobutane

Concentrated HCl was added to a cooled (0°–5° C.) solution of isoamyl nitrite (14.0 g, 120 mmol) and 1-ethoxy-3-methyl-2-butene (6.84 g, 60 mmol). The temperature was maintained below 5° C. during the addition and the reaction mixture was stirred at 5° C. for an additional 30 min. The product was filtered and washed with a cold (–20° C.) 1:1 mixture of ethanol and ether. The solid was further washed with ether to afford a white solid. Yield: 6.9 g (64%); mp 84°–85° C. $^1$H NMR (CDCl$_3$) ε 1.12 (t, 3H, CH$_2$CH$_3$), 1.65 (d, 6H, CH$_3$), 3.49 and 3.95 (m, 2H, CH$_2$OCH$_2$CH$_3$), 4.15 (m, 2H,CH$_2$CH$_3$), 6.12 (dd, 1H, [CH$_3$]$_2$C=CH—]. MS: (M+H)$^+$=180.

C. Preparation of 8-t-Boc-amino-5-aza-4,4-dimethyl-1-(2-nitro-1H-imidazol-1-yl)-6-[(2-nitroimidazol-1-yl)methyl]-6-oxaoctan-3-one oxime To a suspension of 4-chloro-4-methyl-1-(2-nitro-1H-imidazol-1-yl)-3-nitrosopentane (1.3 g, 0.005 mole, Example 10(A)) in acetonitrile (50 mL) was added 2-aminoxy-3-(2-nitro-1H-imidazol-1-yl)-1-t-Boc aminopropane (1.5 g, 0.005 mole, Example 20(D)) and diisopropylethylamine (0.75 g, 0.006 mole) and the mixture stirred for 48 hrs. The clear solution obtained was concentrated and the resultant greenish thick oil was purified by column chromatography (CH$_2$Cl$_2$:CH$_3$OH, 95:5). U.V. visible fractions were collected, and the solvent was evaporated to give a yellow solid. Yield 2.1 g. It was recrystallized from ethyl acetate to yield the title product. mp: 175°–176° C. $^1$H NMR (CDCl$_3$) ε 0.92 [s, 6H, C(CH$_3$)$_2$], 1.44 (s, 9H, Boc-CH$_3$), 2.82 (m, 2H, OCH$_2$CH$_2$NH—Boc)), 3.33 (m, 2H, CH$_2$C$_2$C=NOH), 3.73 (m, 2H, OCH$_2$CH$_2$NH—Boc), 4.63 (t, 2H, N>CH$_2$CH$_2$C=NOH and CH$_2$N<), 6.92 (s, 1H, NH-Boc), 7.14 and 7.27 (s, 2H, nitroimidazolyl-H), 7.6 (s, 2H, imiH). Anal. Calcd. for C$_{20}$H$_{31}$N$_9$O$_8$:C, 46.28; H, 5.99; N, 23.64. Found C, 45.71; H, 5.95; N, 23.99.

D. Preparation of 1-Ethoxy-3,3,9,9-tetramethyl-12-(2-nitro-1H-imidazol-1-yl)-6-[(2-nitroimidazol-1-yl)methyl]-7-oxa-4,8-diazadodecane-2,10-dione dioxime 8-t-Boc-amino-5-aza-4,4-dimethyl-1-(2-nitro-1H-imidazol-1-yl)-6-[(2-nitroimidazol-1-yl)methyl]-6-oxaoctan-3-one oxime (1.0 g, 0.002 mole) was treated with methanolic HCl (2 mL) and stirred at room temperature for 0.5 hrs. Dry ether (100 mL) was added to this solution and the white solid formed was filtered and dried under vacuum. Yield 0.82 g. To a mixture of the hydrochloride (0.82 g, 0.0018 mole) and diisopropylethylamine (0.7 g, 0.0056 mole), in acetonitrile (10 ml) 1-ethoxy-3-chloro-3-methyl-2-nitrosobutane (0.54 g, 0.003 mol) was added and the reaction was stirred at room temperature for 48 hrs. Acetonitrile was removed on a rotary evaporator, the residue was dissolved in water (5 mL), and the solution was made basic (pH 8.5) by the addition of NaOH and extracted with ethyl acetate (2×10 mL), and dried (Na$_2$SO$_4$). Removal of ethyl acetate gave a thick oil which was dried under vacuum to give a foamy solid. The solid obtained was further recrystallized from methylene chloride to yield the title product. Yield 0.8 g. mp 105°–107° C. $^1$H NMR (DMSO-d$_6$) ε 1.10 [s, 12H, C(CH$_3$)$_2$], 1.67 (s, 3H, CH$_3$), 2.34 (m, 2H, OCH$_2$CH$_2$NH), 2.85 (m, 2H, CH$_2$CH$_2$C=NOH), 3.53 (m, 2H, OCH$_2$CH$_2$N and CH$_2$CH$_3$), 4.61 (m, 4H, >NCH$_2$CH$_2$C=NOH and >NCH$_2$CH), 7.10 and 7.50 (s and d, 4H, nitroimidazolyl-H), 10.78 and 10.82 (s, 2H, CH$_2$C=NOH). MS: (M+H)$^+$=570 Anal. Calcd. for C$_{22}$H$_{36}$N$_{10}$O$_8$: C, 46.47; H, 6.38; N, 24.63. Found: C, 46.28; H, 6.38, N, 24.54.

EXAMPLE 26

Synthesis of 3,3,9,9-Tetramethyl-1-ethoxy-6-[(2-nitro-1H-imidazol-1-yl)methyl]-5-oxa-4,8-diazaundecane-2,10-dione dioxime

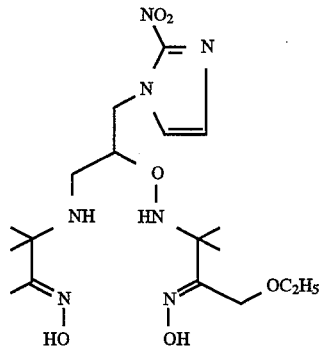

A. Preparation of 2-[[1-(Aminomethyl)-2-(2-nitro-1H-imidazol-1-yl)ethoxy]amino]-3-methyl-1-ethoxy-2-butanone oxime dihydrochloride 1-Ethoxy-3-chloro-3-methyl-2-nitrosobutane (2.2 g, 0.012 mol, Example 25(B)) was added to a mixture of 2-aminoxy-3-(2-nitro-1H-imidazol-1-yl)-1-t-Boc aminopropane (3.01 g, 0.01 mol, Example 20(D)) and diisopropylethylamine (1.6 g, 0.12 mol) in acetonitrile (20 mL) and the mixture stirred at room temperature for 24 hrs. Acetonitrile was evaporated and the oil obtained was triturated with hexane and the residue was poured into water. The solid formed was filtered and recrystallized from hexane and ethyl acetate to yield 3-[[1-[(t-Boc-amino)methyl-2-(2-nitro-1H-imidazol-1yl)ethoxy]amino]-3-methyl-1-ethoxy-2-butanone oxime. Yield 3.5 g (78%). mp=125°–126° C.

Methanolic HCl (3 mL) was added to a solution of 3-[[1-[(t-Boc-amino)methyl-2-(2-nitro-1H-imidazol-1-yl)ethoxy]amino]-3-methyl-1-ethoxy-2-butanone oxime (1.5 g, 0.0034 mol) in methanol (5 ml) and stirred at room temperature for 1 hr. Ether was added to the methanolic solution and the precipitated hydrochloride was filtered and used for the next step without purification. Yield: 1.22 g (84%).

B. Preparation of 3,3,9,9-Tetramethyl-1-ethoxy-6-[(2-nitro-1H-imidazol-1-yl)methyl]-5-oxa-4,8-diazaundecane-2,10-dione dioxime 3-Chloro-3-methyl-2-nitrosobutane (0.43 g, 0.0032 mol; Vassian, Inorg. Chem., 6, 2043 (1967)) was added to a mixture of the title hydrochloride of step A above (1.2 g, 0.0029 mol) and diisopropylethylamine (0.45 g, 0.0035 mol) in acetonitrile (10 mL), and the mixture was stirred at room temperature for 12 hrs. Acetonitrile was removed on a rotary evaporator and the thick oil obtained was basified with potassium carbonate solution. The light green oil obtained was extracted with ethyl acetate and dried (Na$_2$SO$_4$). Ethyl acetate was removed on a rotary evaporator and the oil obtained was purified by column chromatography (silica gel, CH$_2$Cl$_2$:CH$_3$OH, 9:1). Fractions containing the product were collected and evaporated to give a colorless oil, which was dried under vacuum to afford a foamy solid. The solid obtained was dissolved in acetonitrile and left at room temperature for 2 hrs. The solid that formed was filtered and recrystallized from acetonitrile. Yield: 0.42 g (31%). mp. 129°–130° C. $^1$H NMR (DMSO): ε 0.96 and 1.11 [m, 15H, C(CH$_3$)$_2$ and CH$_2$CH$_3$)], 1.65 (s, 6H, CH$_3$), 2.30 (m, 2H, HNCH$_2$CHOH), 3.42 (m, 2H, CH$_2$CH$_3$), 3.80 (m, 1H, CHO), 4.17 (CH$_2$OCH$_2$CH$_3$), 4.5 (m, 2H, CHOHCH$_2$N<), 7.15 and 7.59 (s, 2H, imiH), 10.43 (s, 1H, NOH) and 10.83 (s, 1H, NOH). MS:(M+H)$^+$=444 Anal. Calcd. for C$_{18}$H$_{33}$N$_7$O$_6$: C, 48.75; H, 7.50; N, 22.11. Found: C, 49.00; H, 7.64; N, 21.65.

EXAMPLE 27

Synthesis of 4,4,10,10-Tetramethyl-7-[(2-nitro-1H-imidazol-1-yl)methyl]-6-oxa-5,9-diazatridecane-3,11-dione dioxime

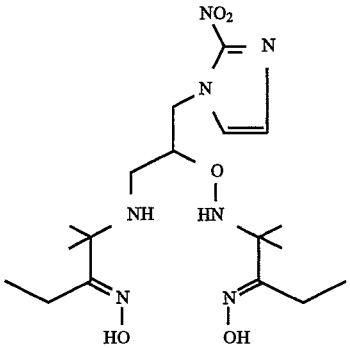

A. Preparation of 4-Chloro-4-methyl-3-nitrosopentane

Concentrated HCl (9.0 mL, 0.11 mol) was added to a cooled (0°–5° C.) solution of isoamyl nitrite (14.8 g, 0.1 mol) and 2-methyl-2-pentene (8.4 g, 0.1 mol). The temperature was maintained below 5° C. during the addition and the reaction mixture was stirred at 5° C. for an additional 30 min. The product was filtered and washed with a cold (–20° C.) 1:1 mixture of petroleum ether. The solid was further washed with petroleum ether to afford a white solid. Yield: 4.9 g (34%); mp 85°–86° C. $^1$H NMR (CDCl$_3$) ε 0.98 (CH$_2$CH$_3$), 1.68 (d, 6H, CH$_3$), 2.05 (m, 2H, CH$_2$CH$_3$), 5.88 (dd, 1H, CHNO). MS: 299 (2M+H)$^+$. Anal. Calcd. for C$_6$H$_{12}$NOCl: C, 48.17; H, 8.08; N, 9.36, Cl,23.70. Found: C, 48.47; H, 8.33; N, 9.3, Cl.24.04.

B. Preparation of 4,4,10,10-Tetramethyl-7-[(2-nitro-1H-imidazol-1-yl)methyl]-6-oxa-5,9-diazatridecane-3,11-dione dioxime 4-Chloro-4-methyl-3-nitrosopentane (1.45 g, 0.011 mol) was added to a mixture of 2-aminoxy-3-(2-nitro-1H-imidazol-1-yl)-1-aminopropane dihydrochloride (1.36 g, 0.005 mol, Example 20(D)) and diisopropylethylamine (1.4 g, 0.011 mol) in acetonitrile (15 mL), and the mixture was stirred at room temperature for 12 h. Acetonitrile was removed on a rotary evaporator and the thick oil obtained was basified with potassium carbonate solution. The light green oil obtained was extracted with ethyl acetate and dried (Na$_2$SO$_4$). Ethyl acetate was removed on a rotary evaporator and the oil obtained was purified by column chromatography (silica gel, CH$_2$Cl$_2$:CH$_3$OH, 9:1). Fractions containing the product were collected and evaporated to give a colorless oil, which was dried under vacuum to afford a foamy solid. The oil obtained was dissolved in acetonitrile and left at room temperature for 2 h. The solid that formed was filtered and recrystallized from acetonitrile. Yield: 0.75 g (35%), mp. 143°–144° C. $^1$HNMR (DMSO): ε 0.98 (m, 6H, CH$_2$CH$_3$), 1.13 [s, 12H, C(CH$_3$)$_2$], 2.19 (m, 4H, CH$_2$CH$_3$), 2.33 (m, 2H, HNCH$_2$CHOH), 3.80 (m, 1H, CHO), 4.5 (m, 2H, CHOHCH$_2$N<), 7.15 and 7.55 (s, 2H, imiH), 10.35 and 10.37 (s, 2H, NOH). MS:(M+H)$^+$=428 Anal. Calcd. for C$_{18}$H$_{33}$N$_7$O$_5$: C, 50.57; H, 7.78; N, 22.93. Found: C, 50.74; H, 7.81; N, 22.93.

EXAMPLE 28

Synthesis of 4,4,10,10-Tetramethyl-7-[(2-nitro-1H-imidazol-1-yl)methyl]-8-oxa-5,9-diazapentadecane-3,11-dione dioxime

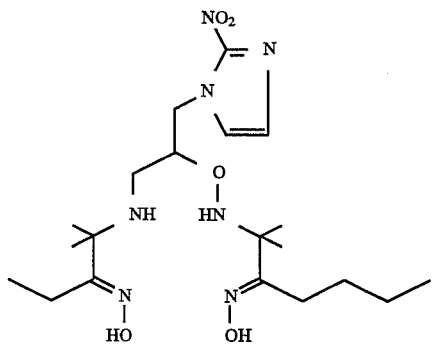

A. Preparation of 6-Methyl-6-chloro-5-nitrosoheptane

To a cooled (0°–5° C.) mixture of isoamyl nitrite (14.0 g, 0.12 mol) and 2-methyl-2-heptene (10.89 g, 0.097 mol) concentrated HCl (9.0 ml, 0.11 mol) was added over a period of 45 min. The temperature was maintained below 5° C. during the addition and the reaction mixture was stirred at 5° C. for an additional 30 min. The product was filtered and washed with cold (–20° C.) petroleum ether. Yield: 5.1 g (29%); mp 84°–85° C. $^1$H NMR (CDCl$_3$) ε 0.87 (m, 3H, CH$_2$CH$_2$CH$_2$CH$_3$), 1.32 (m, 4H, CH$_2$CH$_2$CH$_2$CH$_3$), 1.69 (d, 6H, CH$_3$), 1.98 and 2.12 (m, 2H, CH$_2$CH$_2$CH$_2$CH$_3$), 4.15 (m, 2H,CH$_2$CH$_3$ ), 5.88 (dd, 1H, [CHNO]. MS: 355 (2M+H)$^+$.

B. Preparation of 2-[(1-(Aminomethyl)-2-(2-nitro-1H-imidazol-1-yl)ethoxy]amino]-2-methyl-3-heptanone oxime dihydrochloride 6-Methyl-6-chloro-5-nitrosoheptane (0.8 g, 4.45 mmol) was added to a mixture of 2-aminoxy-3-(2-nitro-1H-imidazol-1-yl)-1-t-Boc aminopropane (1.0 g, 3.3 mmol, Example 20(D)) and diisopropylethylamine (0.7 g, 5.4 mmol) in acetonitrile (15 mL) and the mixture stirred at room temperature for 24 hrs. Acetonitrile was evaporated and the oil obtained was triturated with hexane and the residue was poured into water. The solid formed was filtered and recrystallized from hexane and ethyl acetate to yield 2-[[1-[(t-Boc-amino)methyl]-2-(2-nitro-1H-imidazol-1yl) ethoxy]amino]-2-methyl-3-heptanone oxime. Yield 0.82 g (58%). Methanolic HCl (3 mL) was added to a solution of 2-[[1-[(t-Boc-amino)methyl]-2-(2-nitro-1H-imidazol-1-yl) ethoxy]amino]-2-methyl-3-heptanone oxime (0.82 g, 1.9 mmol) in methanol (5 ml) and stirred at room temperature for 1 hr. Ether was added to the methanolic solution and the precipitated hydrochloride was filtered and used for the next step without purification. Yield: 0.62 g (79%).

C. Preparation of 4,4,10,10-Tetramethyl-7-[(2-nitro-1H-imidazol-1-yl)methyl]-8-oxa-5,9-diazapentadecane-3,11-dione dioxime 4-Chloro-4-methyl-3-nitrosopentane (0.52 g, 3.5 mmol, Example 27(A)) was added to a mixture of the hydrochloride title product of step B above (0.62 g, 1.5 mmol) and diisopropylethylamine (0.45 g, 3.5 mmol) in acetonitrile (10 mL), and the mixture was stirred at room temperature for 12 hrs. Acetonitrile was removed on a rotary evaporator and the thick oil obtained was basified with potassium carbonate solution. The light green oil obtained was extracted with ethyl acetate and dried (Na$_2$SO$_4$). Ethyl acetate was removed on a rotary evaporator and the oil obtained was purified by column chromatography (silica gel, ethyl acetate:hexane, 6:4). Fractions containing the product were collected and evaporated to give a colorless oil, which was dried under vacuum to afford a foamy solid. The solid obtained was dissolved in acetonitrile and left at room temperature for 2 hrs. The solid that formed was filtered and recrystallized from acetonitrile. Yield: 0.32 g (47%). mp. 153°–154° C. $^1$HNMR (DMSO): ε 0.86, 0.96, 1.11, and 1.35 [m, 22H, C(CH$_3$)$_2$, CH$_2$CH$_3$ and CH$_2$CH$_2$CH$_2$CH$_3$)], 2.15 (m, 4H, CH$_2$CH$_2$CH$_2$CH$_3$ and CH$_2$CH$_3$), 2.30 (m, 2H, HNCH$_2$CHOH), 3.80 (m, 1H, CHO), 4.5 (m, 2H, CHOHCH$_2$N<), 7.14 and 7.56 (s, 2H, imiH), 10.35 (s, 1H, NOH), and 10.37 (s, 1H, NOH). MS:(M+H)$^+$=456 Anal. Calcd. for C$_{20}$H$_{37}$N$_7$O$_5$: C, 52.71; H, 8.19; N, 21.53. Found: C, 52.94; H, 8.26; N, 21.63.

EXAMPLE 29

Synthesis of 5,5,11,11-Tetramethyl-1-(5-nitro-2-furyl)-2,9-dioxa-6,10-diazatetradecane-4,12-dione dioxime dihydrochloride

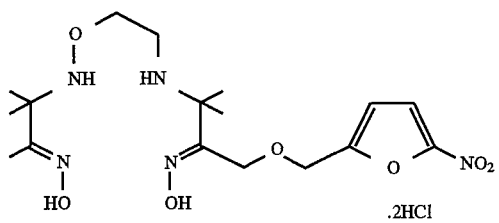

A. Preparation of 2-[[(3-Methyl-2-butenyl)oxy]methyl]-5-nitrofuran

Freshly prepared silver oxide (34.8 g, 0.15 mol) was added to a mixture of 3-methyl-2-buten-1-ol (21.0 g, 25 mL, 0.24 mol) and 5-nitro-2-furfuryl bromide (18.8 g, 0.1 mol) and stirred at room temperature for 12 h. Silver salts were removed by filtration and the filter cake was washed with ether (200 mL). The filtrate and the washings were combined and evaporated to remove ether and excess 3-methyl-2-buten-1-ol. The oil obtained was purified by column chromatography (silica gel, hexane:ethyl acetate, 7:1). Fractions containing the product were collected and evaporated to give a light yellow oil. Yield 5.5 g. $^1$H NMR (CDCl$_3$) $\epsilon$ 1.69 and 1.77 (s, 6H, CH$_3$), 4.09 [d, 2H, (CH$_3$)$_2$C=CHCH$_2$—OCH$_2$)], 4.64 [s, 2H, (CH$_3$)$_2$C=CHCH$_2$—OCH$_2$)], 5.38 (t, 1H, (CH$_3$)$_2$C=CH—), 6.6 and 7.27 (d, 2H, ArH).

B. Preparation of 2-[(3-Chloro-3-methyl-2-nitrosobutoxy)methyl]-5-nitrofuran

Concentrated HCl (2.5 mL) was added to a cooled (0°–5° C.) solution of isoamyl nitrite (14.0 g, 0.12 mol) and 2-[[(3-methyl-2-butenyl)oxy]methyl]-5-nitrofuran (4.0 g, 0.06 mol). The temperature was maintained below 5° C. during the addition and the reaction mixture was stirred at 5° C. for an additional 30 min. The product was filtered and washed with a cold (–20° C.) 1:1 mixture of ethanol and ether. The solid was further washed with ether to afford a light yellow solid. Yield 2.6 g (52%). mp 134°–135° C. $^1$H NMR (DMSO) 1.78 ($\epsilon$ 6H, CH$_3$), 4.44 (s, 2H, HON=CCH$_2$), 4.67 (s, 2H, CH$_2$OAr ), 6.6 and 7.27 (d, 2H, ArH). MS: 277 (M+H)$^+$ C. Preparation of 5,5,11,11-Tetramethyl-1-(5-nitro-2-furyl)-2,9-dioxa-6,10-diazatetradecane-4,12-dione dioxime dihydrochloride 2-[(3-Chloro-3-methyl-2-nitrosobutoxy)methyl]-5-nitrofuran (0.27 g, 1 mmol) was added to a solution of 7-amino-4-aza-3,3-dimethyl-5-oxaheptan-2-one oxime (0.27 g, 1 mmol, Example 7(E)) and diisopropylethylamine (0.4 g, 3 mmol) in acetonitrile (5.0 mL) and stirred at 40° C. for 4 h. After the reaction, acetonitrile was evaporated on a rotary evaporator and the resultant thick oil formed was washed several times with water and dried (Na$_2$SO$_4$). The oil thus obtained was purified by column chromatography (silica gel, CH$_2$Cl$_2$:CH$_3$OH, 9:1). Fractions containing the product were collected and evaporated to give a viscous oil. This was purified as the dihydrochloride title product. mp 168°–169° C. (dec.). Yield 0.23 g. $^1$H NMR (CDCl$_3$) $\epsilon$ 1.24 and 1.34 [s, 12H, C(CH$_3$)$_2$], 2.64 (t, 2H, NHCH$_2$CH$_2$O), 1.90 (s, 3H, CH$_3$), 3.75 (t, 2H, NHCH$_2$CH$_2$O), 4.40 (s, 2H, HON=CCH$_2$), 4.59 (s, 2H, CH$_2$OAr ), 6.6 and 7.27 (d, 2H, ArH). MS: 416 (M+H)$^+$. Anal. Calcd. for C$_{17}$H$_{31}$N$_5$O$_7$Cl$_2$: C, 41.81; H, 6.40; N, 14.34. Found: C, 41.53; H, 6.46; N, 13.78.

EXAMPLE 30

Synthesis of 5,5,11,11-Tetramethyl-1-(5-nitro-2-furyl)-2,7-dioxa-6,10-diazatetradecane- 4,12-dione dioxime dihydrochloride

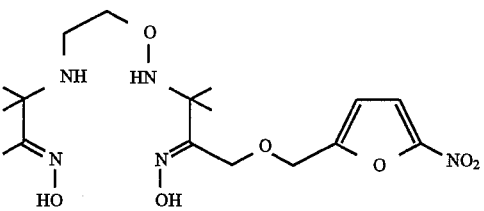

A. Preparation of 3-[[2-(t-Boc-amino)ethoxy]amino]-3-methyl-1-[(5-nitro-2-furanyl)methoxy]-2-butanone oxime 2-[(3-Chloro-3-methyl-2-nitrosobutoxy)methyl]-5-nitrofuran (2.37 g, 8.5 mmol, Example 29(B)) was added to a solution of 2-(aminoxy-1-t-Boc-aminoethane (1.5 g, 8.5 mmol, Example 7(C)) and N,N-diisopropylethylamine (1.3 g, 10 mmol) in acetonitrile (15.0 mL) and stirred at 40° C. for 4 h. After the reaction, acetonitrile was evaporated on a rotary evaporator and the resultant thick oil formed was washed several times with water and dried (Na$_2$SO$_4$). The oil thus obtained was purified by column chromatography (silica gel, CH$_2$Cl$_2$:CH$_3$OH, 95:5) Fractions containing the product were collected and evaporated to give a viscous oil. Yield 1.47 g. $^1$H NMR (CDCl$_3$) $\epsilon$ 1.34 [s, 6H, C(CH$_3$)$_2$], 1.44 (s, 6H, NHBoc), 3.28 (m, 2H, NHCH$_2$CH$_2$O), 3.75 (t, 2H, NHCH$_2$CH$_2$O), 4.40 (s, 2H, HON=CCH$_2$), 4.59 (s, 2H, CH$_2$OAr), 4.95 (bs, 1H, NHBoc), 6.6 and 7.27 (d, 2H, ArH).

B. Preparation of 5,5,11,11-Tetramethyl-1-(5-nitro-2-furyl)-2,7-dioxa-6,10-diazatetradecane-4,12-dione dioxime dihydrochloride Methanolic HCl (5 mL) was added to a solution of the title product of step A above (2 g, 0.05 mol) in methanol (5 ml) and stirred at room temperature for 30 min. Ether was added to the methanolic solution and the hydrochloride formed was used in the next step. Diisopropylethylamine (1.29 g, 0.01 mol) was added to a slurry of the hydrochloride (0.8 g, 0.0025 mol) in acetonitrile (10 mL) for 15 min. 3-Chloro-3-methyl-2-nitrosobutane (0.42 g, 0.003 mol) was added to the reaction mixture and stirred at room temperature for 12 h. After the reaction, acetonitrile was evaporated on a rotary evaporator and the resultant thick oil formed was washed several times with water and dried (Na$_2$SO$_4$). The oil thus obtained was purified by column chromatography (silica gel, CH$_2$Cl$_2$:CH$_3$OH, 9:1). Fractions containing the product were collected and evaporated to give a viscous oil. Yield: 0.43 g. It was converted to the hydrochloride and recrystallized from ethanol-ether. mp 99°–100° C. $^1$H NMR (DMSO) $\epsilon$ 1.01 and 1.18 [s, 12H, C (CH$_3$)$_2$ ], 1.68 (s, 3H, CH$_3$), 2.30 (m, 2H, NHCH$_2$CH$_2$O), 3.5 (m, 2H, NHCH$_2$CH$_2$O), 4.30 (s, 2H, HON=CCH$_2$), 4.5 (s, 2H, CH$_2$OAr), 6.6 and 7.77 (d, 2H, ArH), 10.3 and 11.0 Is, 2H, NOH). MS: 416 (M+H)$^+$. Anal. Calcd. for C$_{17}$H$_{31}$N$_5$O$_7$·C$_2$H$_5$OH: C, 42.70; H, 6.98; N, 13.10. Found: C, 42.80; H, 6.94; N, 12.85.

EXAMPLE 31

Synthesis of 3,3,9,9-Tetramethyl-1-[[(5-nitro-2-furyl)carbonyl]amino]-5-oxa-4,8-diazaundecane-2,10-dione, dioxime

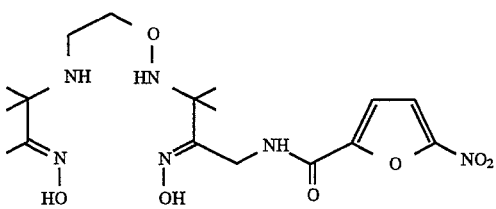

A. Preparation of N-(3-Methyl-2-butenyl)-5-nitro-2-furancarboxamide

5-Nitro-2-furoic acid (5 q, 0.032 mol) was dissolved in dry DMF (25 mL). To this solution was added 1,1'-carbonyldiimidazole (5.7 g, 0.035 mol). The mixture was stirred at room temperature for 15 min; an orange colored suspension was formed. 3-Methyl-2-butenyl amine hydrochloride (3.9 g, 0.032 mol) was suspended in dry DMF (15 mL) in an Erlenmeyer flask and neutralized with $NaHCO_3$, and the amine suspension was slowly added to the 5-nitro-2-furanoic acid and 1,1'-carbonyldiimidazole reaction mixture. The reaction mixture was stirred at room temperature for 2 h. TLC (silica gel, 10% methanol-dichloromethane, $R_f$=0.45) indicated completion. DMF was removed on a rotary evaporator and the residue was stirred with water (800 mL) to give a yellow solid. Yield: 3.3 g (46%). mp 92°–94° C. MS m/z, 448 (2M)+, 242 $(M+NH_4)^+$, 225 $(M+H)^+$. $^1$H NMR (DMSO-$d_6$) ε 1.73 [d, 6H, $(CH_3)_2C$=], 3.86 (t, 2H, $CH_2CH$=), 5.22 (t, 1H, $CH_2CH$=), 7.40 and 7.78 (d, 2H, furanyl-H), 8.96 (t, 1H, NHCO).

B. Preparation of N-(3-Chloro-3-methyl-2-nitrosobutyl)-5-nitro-2-furancarboxamide N-(3-Methyl-2-butenyl)-5-nitro-2-furancarboxamide (2.2 g, 0.01 mol) was suspended in isoamyl nitrite (60 mL) and cooled to −5° C. concentrated HCl (1 mL, 37%, 0.01 mol) was added through a syringe. The reaction mixture was stirred at −5° C. for 30 min and at room temperature for 30 min. The solid was filtered and washed with chilled (−10° C.) ethanol-ether (100 mL). A light green powder was obtained. Yield: 1.5 g (52%). mp 110°–112° C. MS m/z 254 [(M+H)-HCl]+. $^1$H NMR (DMSO-$d_6$) ε 1.82 [s, 6H, $(CH_3)_2$C=], 4.28 (d, 2H, $CH_2C$=N), 7.49 and 7.75 (d, 2H, furanyl-H), 8.66 (t, 1H, NHCO), 11.72 (s, 1H, C=NOH).

C. Preparation of N-[3-[[(t-Boc-amino)ethoxy]amino]-2-(hydroxyimino)-3-methylbutyl]-5-nitro-2-furancarboxamide 2-(Aminoxy)-1-t-Boc-aminoethane (0.4 g, 2.3 mmol, Example 7(C)) and N-(3-chloro-3-methyl-2-nitrosobutyl)-5-nitro-2-furancarboxamide (0.5 g, 1.7 mmol) were suspended in acetonitrile (10 mL). To the solution was added N,N-diisopropylethylamine and the reaction mixture was stirred under $N_2$ at room temperature overnight. A clear solution was obtained. Solvent was evaporated and the residue was loaded on silica gel column and eluted with 50% ethyl acetate-hexane. Yield: 0.62 g (85%). MS m/z 430 (M+H)+, 374 (M−>=)+. $^1$H NMR (CDCl$_3$) ε 1.26 [s, 6H, $(CH_3)_2$C=], 1.38 (s, 9H, boc-$CH_3$), 3.35 (m, 2H, $CH_2NH$), 3.68 (t, 2H, $NHOCH_2$), 4.28 (d, 2H, $CH_2NH$), 5.15 (tb, 1H, NHBoc), 6.24 (s, 1H, ON), 7.35 (s, 2H, furanyl-H), 7.72 (tb, 1H, NHCO), 8.54 (s, 1H, C=NOH).

D. Preparation of 3,3,9,9-Tetramethyl-1-[[(5-nitro-2-furyl)carbonyl]amino]-5-oxa-4,8-diazaundecane-2,10-dione, dioxime N-[3-[[(t-Boc-amino)ethoxy]amino]-2-(hydroxyimino)-3-methylbutyl]-5-nitro-2-furancarboxamide (0.22 g, 0.5 mmol) was suspended in methanol (10 mL) and solution was cooled in an ice bath for 30 min. HCl saturated methanol solution was added dropwise (14 drops) and the suspension was stirred at room temperature under $N_2$ overnight. TLC (silica gel, 50% ethyl acetate-hexane) indicated that the debocylation was complete. Methanol was evaporated to give a white solid. HPLC (Vydac $C_{18}$, 0.46×25 cm, 5μ column; 1 mL/min gradient elution from 100% A to 50% B in 50 min, where A is water, B is acetonitrile, both containing 0.01% TFA) showed one peak with a retention time of 15 min. $^1$H NMR ($D_2O$) ε 1.42 [s, 6H, $(CH_3)_2C$=], 3.24 (m, 2H, $CH_2NH$), 4.13 (t, 2H, $NHOCH_2$), 4.30 (s, 2H, $CH_2NH$), 7.31 and 7.53 (d, 2H, furanyl-H).

This solid was suspended in acetonitrile (10 mL), cooled to 0° C. and neutralized with N,N-diisopropylethylamine (0.13 g, 1 mmol). 3-Chloro-3-methyl-2-nitrosobutane (0.1 g, 0.7 mmol) was added and the mixture was stirred at room temperature under $N_2$ overnight. HPLC showed one major peak with a retention time of 26 min while no starting material (retention time=15 min) was observed. Acetonitrile was evaporated and the residue was loaded on a silica gel column, eluted with 5% methanol-dichloromethane. Fractions containing a UV visible spot with $R_f$=0.4 were collected. After removal of solvent, a slightly yellow solid was obtained The free base was dissolved in 5 mL of ether and cooled in an ice bath. To the cooled solution was added 10 drops of HCl/methanol. The HCl salt precipitated out to form a gummy product, which was dried under vacuum overnight. The salt was then loaded on silica gel column and eluted with 50% THF-$CH_2Cl_2$. Fractions with $R_f$=0.5 were collected, and evaporated on a rotary evaporator. 100 mg HCl salt was obtained. mp 126°–128° C. MS m/z 429 (M+H)+. $^1$H NMR (CDCl$_3$) ε 1.26 [d, 12H, $(CH_3)_2C$=], 1.87 (s, 3H, $CH_3C$=N), 2.65 (m, 2H, $CH_2NH$), 3.81 (t, 2H, $NHOCH_2$), 4.38 (s, 2H, $CH_2NH$), 6.08 (b, 1H, ONH), 7.27 and 7.34 (d, 2H, furanyl H), 7.89 (tb, 1H, NHCO). Anal. Calcd. for $C_{19}H_{36}Cl_2N_6O_8$·1 EtOH: C, 41.69; H, 6.63; N, 15.35; Cl, 12.95. Found: C, 40.92; H, 6.64; N, 15.25; Cl, 12.90.

EXAMPLE 32

Preparation of $^{99m}$Tc complexes (Method 3)

The following general procedure was used to prepare the $^{99m}$Tc complexes of the ligand title products of the above Examples 9, 10, 12, 14, 20, 22, 25 and 28:

Ligand (2–4 mg) was dissolved in 0.1M HCl (0.1–0.15 mL) and 0.9% sodium chloride solution (1.0 mL), followed by 0.1M sodium hydrogen carbonate buffer (0.5 mL) in a 5 mL glass vial. Saline and $^{99}$Mo/$^{99m}$Tc generator eluate (total volume of 0.5–1.0 mL) were then added, and the vial was sealed and shaken to mix the reagents. A commercially available kit for the preparation of $^{99m}$Tc-DTPA (Techneplex kit for the preparation of $^{99m}$Tc-Pentetate) was reconstituted with 2–4 mL of 0.9% sodium chloride solution, and an aliquot of this solution (0.15–0.3 mL) was added the vial containing ligand and $^{99m}$TcO$_4^-$. The vial was shaken and allowed to stand at room temperature. The radiochemical purities (RCP) of the $^{99m}$Tc-complexes were measured by reversed phase HPLC, using a 5 or 10 micron, 15 cm reversed phase PRP-1 column that was eluted with 65/35 acetonitrile/0.1M ammonium acetate (NH₄OAc, pH 4.6). All technetium complexes had an RCP greater than 90% within 10 minutes.

The complexes thus formed had the names (followed in parentheses by the example number of the Example in which the starting ligand was prepared):

Oxo[1-(2-nitro-1H-imidazol-1-yl)-3,3,9,9-tetramethyl-5-oxa-4,8-diaza-2,10-undecanedione dioximato](3-)-N, N', N", N'"]technetium-$^{99m}$Tc(V) (Example 9);

Oxo[12-(2-nitro-1H-imidazol-1-yl)-3,3,9,9-tetramethyl-7-oxa-4,8-diaza-2,10-dodecanedione dioximato](3-)-N, N', N", N'"]technetium-$^{99m}$Tc(V) (Example 10);

Oxo[1,13-bis(2-nitro-1H-imidazol-1-yl)-4,4,10,10-tetramethyl-6-oxa-5,9-diaza-3,11-tridecanedione dioximato](3-)-N, N', N", N'"]technetium-$^{99m}$Tc(V) (Example 12);

Oxo[1-(2-hydroxy-3-(2-nitro-1H-imidazol -1yl)propoxy)-3,3,9,9-tetramethyl-5-oxa-4,8-diaza-2,10-undecanedione dioximato](3-) -N, N', N", N'"]technetium-$^{99m}$Tc (V) (Example 14);

Oxo[6-[(2 -nitro-1H-imidazol-1-yl)methyl]-3,3,9,9-tetramethyl-5-oxa-4,8-diaza-2,10undecanedione dioximato (3-)-N, N', N", N'"]technetium-$^{99m}$Tc(V) (Example 20);

Oxo[1,13-bis(2-nitro-1H-imidazol-1-yl)-4,4,10,10-tetramethyl-6-oxa-7-(hydroxymethyl)-5,9-diaza-3,11-dodecanedione dioximato(3-)-N, N', N", N'"]technetium-$^{99m}$Tc(V) (Example 22);

Oxo[1-ethoxy-3,3,9,9-tetramethyl-12-(2-nitro-1H-imidazol-1-yl)-6-[(2-nitroimidazol-1-yl)methyl]-7-oxa-4,8-diazadodecane-2,10-dione dioximato(3-)-N, N', N", N'"]technetium-$^{99m}$Tc(V) (Example 25); and Oxo[4,4,10,10-tetramethyl-7-[(2-nitro-1-H-imidazol-1-yl)methyl]-8-oxa-5,9-diazapentadecane-3,11-dione dioximato(3-)-N, N', N", N'"]technetium-$^{99m}$Tc(V) (Example 28) .

EXAMPLE 33

Preparation of $^{99m}$Tc complexes

The technetium complexes of the ligand title products of Examples 23, 24, 26, 27, 30 and 31 were prepared using the method described in Example with the following exceptions:

the ligand from Example 23 was dissolved in 0.1 mL of water instead of 0.1M HCl; and water was also substituted for HCl for complexation of the ligand of Example 30.

The complexes thus formed as above had the names (followed in parentheses by the example number of the Example in which the starting ligand was prepared):

Oxo[12-(2-nitro-1H-imidazol-1-yl) -3,3,9,9-tetramethyl-6-(hydroxymethyl)-7-oxa-4,8-diaza-2,10-dodecanedione dioximato(3-)-N, N', N", N'"]technetium-$^{99m}$Tc (V) (Example 23 );

Oxo [3,3,9,9-tetramethyl-6-[[3-(2-nitro-1H-imidazol-1-yl)propoxy]methyl]-5-oxa-4,8-diazaundecane-2,10-dione, dioximato (3-) N,N',N",N'"]technetium-$^{99m}$Tc(V) (Example 24);

Oxo[3,3,9,9-tetramethyl-1-ethoxy-6-[(2-nitro-1H-imidazol-1-yl)methyl]-5-oxa-4,8-diazaundecane-2,10-dione dioximato(3-)-N, N', N", N'"]technetium-$^{99m}$Tc(V) (Example 26);

Oxo[4,4,10,10-tetramethyl-7-[(2-nitro-1H-imidazol-1-yl) methyl]-6-oxa-5,9 -diazatridecane-3,11-dione dioximato (3-)-N, N', N", N'"]technetium-$^{99m}$Tc(V) (Example 27);

Oxo[5,5,11,11-tetramethyl-1-(5-nitro-2-furyl)-2,7-dioxa-6,10-diazatetradecane-4,12-dione dioximato(3-)-N, N', N", N'"]technetium-$^{99m}$Tc(V) (Example 30); and Oxo[3,3,9,9-tetramethyl-1-[[(5-nitro-2-furyl)carbonyl]amino]-5-oxa-4,8-diazaundecane-2,10-dione dioximato(3-)-N, N', N", N'"]technetium-$^{99m}$Tc(V) (Example 31).

EXAMPLE 34

Synthesis of the R and S isomers of Oxo[6-[(2-nitro-1H-imidazol-1yl)methyl]-3,3,9,9-tetramethyl-5-oxa-4,8-diaza-2,10-undecanedione dioximato(3-)-N, N', N", N'"]technetium-$^{99m}$Tc(V)

A 5 cc glass vial containing 2.0 mg of freeze-dried racemic ligand of Example 20 at pH 8.2 was reconstituted with 1.8 mL of a mixture of 0.9% sodium chloride and $^{99}$Mo/$^{99m}$Tc generator eluate. The vial was shaken to dissolve the reagents. A commercially available kit for the preparation of $^{99m}$Tc-DTPA (Techneplex kit for the preparation of $^{99m}$Tc-Pentetate) was reconstituted with 4 mL of 0.9% sodium chloride solution, and an aliquot of this solution (0.15–0.3 mL) was added the vial containing ligand and $^{99m}$TcO₄⁻. After 10 minutes at room temperature, the contents of the vial were adsorbed onto reversed-phase PRP-1 resin, and the supernate discarded. The resin was washed with 1 mL of a 1:3 mixture of ethanol:saline and the supernate was discarded. The racemic mixture of technetium complexes was eluted from the resin with 0.5 mL of EtOH, which was evaporated to near dryness with a nitrogen stream. The individual isomers of the $^{99m}$Tc complex of the ligand of Example 20 were then resolved from one another on a Chiralpak AD column that was eluted with 65/35 hexane/EtOH/0.1% diethylamine (Et₂NH) at 1 mL/min.

EXAMPLE 35

Synthesis of 3,3,6,9,9-Pentamethyl-5-oxa-8-diaza-4,8-diazaundecane-2,10-dione dioxime

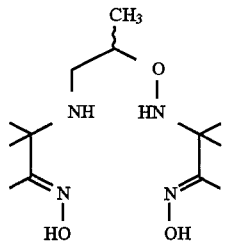

A. Preparation of 1-t-Bocamino-2-phthalimidooxypropane 1-t-Bocamino-2-hydroxypropane (11.7 g, 67 mmol), N-hydroxyphthalimide (13.1 g, 80 mmol) and triphenylphosphine (21 g, 80 mmol) were dissolved in THF (500 mL). To this solution was added molecular sieve (5 g), followed by diethylazodicarboxylate (14 g, 80 mmol) added in small portions. The reaction mixture was stirred at room temperature for 24 h. THF was removed and the residue was purified by column chromatography (silica gel, ethyl acetate hexane 2:8). Fractions containing the product (Rf=0.42) were collected and evaporated to give a white solid. Yield 13.4 g (64%). It was crystallized from hexane ethyl acetate. mp 105°–107° C.

B. Preparation of 3,3,6,9,9-Pentamethyl-5-oxa-4,8-diaza-4,8-diazaundecane-2,10-dione dioxime Hydrazine (1.5 g, 40 mmol) was added to a solution of 1-t-Bocamino-2-phthalimidooxypropane 25 (12 g, 38 mmol) in ethanol (250 mL) and the mixture was refluxed for 6 h. The reaction mixture was cooled in ice for 30 min. and filtered. The filtrate was evaporated to give 2-aminoxy-3- methyl-1-t-Boc aminopropane as an oil. Yield 7.0 g (97%). This was dissolved in methanolic HCl and stirred at room temperature for 30 min. Ether (200 mL) was added to the methanolic solution and the 2-aminoxy-3-methyl-1-aminopropane hydrochloride formed was filtered and used in the next step without further purification.

The above hydrochloride (0.5 g, 3 mmol) was suspended in acetonitrile (10 mL) and the suspension was cooled to 0° C. and neutralized with diisopropylethylamine. 3-Chloro-3-methyl-2-nitrosobutane (1.9 g, 15 mmol) was added to the reaction mixture and stirred at 0° C. for 30 min and at room temperature for 4 h. Acetonitrile was evaporated and the residue was neutralized with saturated potassium carbonate solution (10 mL) and extracted with ethyl acetate (3×50 mL). Ethyl acetate was evaporated to give an oil which on trituration with hexane afforded a white solid. It was crystallized from hexane/ethyl acetate. mp 104°–106° C. Yield 0.83 g. MS: (m/z) 289 (M+H)$^+$Anal. calcd. for $C_{13}H_{28}N_4O_3$: C, 54.14; H, 9.79; N, 19.43. Found: C, 54.37; H, 10.15; N, 19.72.

EXAMPLE 36

Stereoselective synthesis of a stereoisomer of the ligand of Example 20, (R)-3,3,9,9-Tetramethyl-6-[(2-nitro-1H-imidazol-1-yl)methyl]-5-oxa-4,8-diazaundecane-2,10-dione dioxime, from (S)-(+)-epichlorohydrin

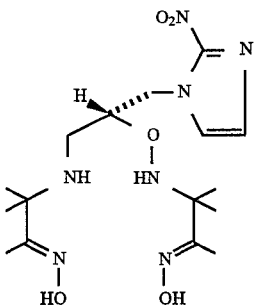

A. Preparation of (S)-1-Chloro-3-phthalimido-2-propanol (S)-(+)-epichlorohydrin (5 g, 54 mmol) and phthalimide (5 q, 34 mmol) were mixed and the suspension was refluxed under $N_2$ for 4 h. The progress of the reaction was followed by TLC (silica gel, 60% ethyl acetate-hexane). The reaction mixture was then cooled, and poured into hexane (150 mL). The solid which formed was dissolved in ethyl acetate (150 mL). Silica gel (10 g) was added to the ethyl acetate solution and evaporated on a rotary evaporator. The free flowing powder was loaded onto a silica gel column and eluted with methylene chloride-ethyl acetate (9:1) The initial UV visible fractions were found to be the epoxide. Further elution afforded the title halohydrin. The crude product was recrystallized from diisopropyl ether to afford 4.5 g (55.4%). MS m/z, 240 (M+H)$^+$ $^1$HNMR (CDCl$_3$) ε 2.80 (d, 1H, CHOH), 3.64 (m, 2H, CH$_2$Cl), 3.90 (m, 2H, phth-CH$_2$), 4.18 (m, 1H, CHOH), 7.74 and 7.86 (m, 4H, phth-H). mp 100°–101° C.

B. Preparation of (S)-N-(2,3-epoxypropyl)phthalimide

To a cooled (0° C.) solution of the 1-chloro-3-phthalimido-2-propanol of step A above (2 g, 0.01 mol) in THF (15 mL) sodium hydride (90.24 g, 0.01 mol) was added and the mixture was stirred at 0° C. for 30 min. and at room temperature for 24 hrs. Solvent was removed and the residue was treated with water (5 mL) and extracted with ethyl acetate. Ethyl acetate was removed and the solid obtained was chromatographed over silica gel (9:1 CH$_2$Cl$_2$:Ethyl acetate). UV visible fractions were collected and evaporated to give the title epoxide. Yield 1.2 g. $^1$HNMR (CDCl$_3$) ε 2.68 and 2.84 (m, 2H, CH$_2$phth), 3.24 (m, 1H, epoxy-CH), 3.80 and 3.94 (m, 2H, epoxy-CH$_2$), 7.70 and 7.88 (m, 4H, phth-H).

C. Preparation of (R)-2-[2-Hydroxy-2-(nitro-1H-imidazol-1-yl)ethyl]-1H-isoindole-1,3(2H)-dione To a solution of (S)-N-(2,3epoxypropyl)phthalimide (1.75 g, 0.0086 mol) in ethanol (10 mL) 2-nitroimidazole (1.13 g, 0.01 mol) and potassium carbonate (75 mg) were added and the reaction mixture was refluxed for 6 hrs. The reaction mixture was cooled and poured into water (50 ml) and the yellow solid formed was filtered and dried. Yield 2.5 g (91%). It was recrystallized from methanol. mp 191°–192° C. dec. $^1$HNMR (DMSO) ε 3.62 (m, 4H, PhthNCH$_2$CHOH), 4.08 (m, 1H, CHOH), 4.32 and 4.63 (m, 2H, CHOHCH$_2$N<), 5.54 (d, 1H, CHOH), 7.15 and 7.68 (s, 2H, imiH), 7.8 (m, 4H, ArH). MS: (M+H)$^+$=317.

D. Preparation of (S)-α-[(t-Boc-amino)methyl]-2-nitro-1H-imidazole-1-ethanol

To a suspension of (R)-2-[2-hydroxy-2-(nitro-1H-imidazol-1-yl)ethyl]-1H-isoindole-1,3(2H)-dione (2.5 g, 0.008 mol) in methanol (10 mL) hydrazine (0.32 g, 0.01 mol) was added and the mixture was refluxed for 6 hrs. The reaction mixture was cooled and the methanol was removed on a rotary evaporator. The mixture of the amino hydrin and the hydrazide was dissolved in a solution of sodium carbonate (2.12 g, 0.02 mol) in water (5 mL). THF (15 mL) was added to this mixture and cooled to 0° C. Ditertiarybutyl dicarbonate (2.18 g, 0.01 mol) was added to this mixture and stirred at 0° C. for 1 h and room temperature for 48 h. THF-water was removed on a rotary evaporator and the residue was extracted with ethyl acetate (3×25 mL). The ethyl acetate layer was washed with water, dried (Na$_2$SO$_4$) and evaporated on a rotary evaporator to yield the title compound as a yellow solid. Yield 1.72 g (75%). It was recrystallized from hexane-ethyl acetate. mp. 128°–129° C. $^1$HNMR (DMSO) ε 1.39 (s, 9H, NHBoc), 2.92 (m, 2H, BocHNCH$_2$CHOH), 3.75 (m, 1H, CHOH), 4.14 and 4.55 (m, 2H, CHOHCH$_2$N<), 5.25 (d, 1H, CHOH), 6.94 (m, 1H, BocHN), 7.15 and 7.59 (s, 2H, imiH).

E. Preparation of (R)-2-[1-[(t-Boc-amino)methyl]-2-(2-nitro-1H-imidazol-1-yl)ethoxy]1H-isoindole-1H)-dione N-Hydroxyphthalimide (0.4 g, 0.0025 mol), (S)-α-[(t-Boc-amino)methyl]-2-nitro-1H-imidazole-1-ethanol (0.57 g, 0.002 mol) and triphenylphosphine (0.79 g, 0.03 mol) were dissolved in THF (7.5 mL), and cooled to −15° C. Molecular sieve (5 g) was added to the reaction mixture and diethylazodicarboxylate (0.5 g, 0.003 mol) was added to the solution and the stirring was continued for 1 hr at −15° C. The reaction mixture became dark red and the color disappeared after 1 hr. The reaction mixture was stirred at room temperature for 24 h and evaporated on a rotary evaporator to dryness. The residue was chromatographed over silica gel, using hexane-ethyl acetate (7:3, 6:4) as eluent. Evaporation of the solvent afforded the title compound as a foamy solid. Yield: 0.53 g (61%). MS: (M+H)$^+$=432$^+$.

F. Preparation of (R)-1-[2-(Aminooxy)-3-(t-Boc-amino) propyl]-2-nitro-1H-imidazole Hydrazine (98%, 50 mg, 0.0015 mole) was added to a solution of (R)-2-[1-[(t-Boc-amino)methyl]-2-(2-nitro-1H-imidazol-1-yl)ethoxy]1H-isoindole-1,3(2H)-dione (0.53 g, 0.0012 mol) in ethanol (50 mL) and the mixture was refluxed for 6 h. The solid which formed was filtered and the filtrate was evaporated on a rotary evaporator. The thick oil obtained was triturated with ethyl acetate and the resultant precipitate was removed by filtration. The ethyl acetate solution was evaporated on a rotary evaporator to give the title product as an oil. Yield: 0.32 g (86%). $^1$HNMR (CDCl$_3$) ε 1.46 (s, 9H, NHBoc), 3.40 (m, 2H, BocHNCH$_2$CHO), 3.82 (m, 1H, CHONH$_2$), 4.4 and 4.62 (m, 2H, CHOHCH$_2$N<), 4.9 (bs, 1H, NHtBoc), 5.2 (bs, 2H, NH$_2$), 7.15 and 7.27 (s, 2H, imiH).

F. Preparation of (R)-1-[3-Amino-2-(aminoxy)propyl]-2-nitro-1H-imidazole dihydrochloride Methanolic HCl (1 mL) was added to a solution of (R)-1-[2-(aminooxy)-3-(t-Boc-amino)propyl]-2-nitro-1H-imidazole (0.3 g, 0.001 mol) in methanol (1.5 mL), and the mixture was stirred at room temperature for 20 min. Ether/ 15 mL) was added to the methanolic solution and the (R)-1-[3-amino-2-(aminooxy)propyl]-2-nitro-1H-imidazole dihydrochloride which formed was filtered and dried under vacuum. This was used in the next step without further purification. Yield 0.23 g (84%). MS: (M+H)$^+$=202.

H. Preparation of (R)-3,3,9,9-Tetramethyl-6-[(2-nitro-1H-imidazol-1-yl)methyl]-5-oxa-4,8-diazaundecane-2,10-dione dioxime 3-Chloro-3-methyl-2-nitrosobutane (0.145 g, 0.0011 mol) was added to a mixture of (R)-1-[3-amino-2-(aminoxy) propyl]-2-nitro-1H-imidazole dihydrochloride (0.15 g, 0.0005 mol) and diisopropylethylamine (0.3 g, 0.0023 mol) in acetonitrile (1.5 mL), and the mixture was stirred at room temperature for 12 hrs. Acetonitrile was removed on a rotary evaporator and the thick oil obtained was basified with potassium carbonate solution. The light green oil obtained was extracted with ethyl acetate and dried (Na$_2$SO$_4$). Ethyl acetate was removed on a rotary evaporator and the oil obtained was purified by column chromatography (silica gel, CH$_2$Cl$_2$:CH$_3$OH, 9:1). Fractions containing the product were collected and evaporated to give a colorless oil, which was dried under vacuum to afford a foamy solid. The solid obtained was dissolved in acetonitrile and left at room temperature for 2 hrs. The solid that formed was filtered and recrystallized from acetonitrile. Yield: 120 mg (55%). $^1$HNMR (DMSO): ε 0.96 and 1.11 [s, 12H, C(CH$_3$)$_2$], 1.65 (s, 6H, CH$_3$), 2.30 (m, 2H, HNCH$_2$CHOH), 3.80 (m, 1H, CHO), 4.5 (m, 2H, CHOHCH$_2$N<), 7.15 and 7.59 (s, 2H, imiH), 10.43 (s, 2H, NOH). MS:(M+H)$^+$=400.

The corresponding S stereoisomer, (S)-3,3,9,9-tetramethyl-6-[(2-nitro-1H-imidazol-1-yl)methyl]-5-oxa-4,8-diazaundecane-2,10-dione dioxime, is prepared by the above procedure, starting with (R)-(−)-epichlorohydrin in step A.

Thus, the R or S stereoisomers of the compound 3,3,9,9-tetramethyl-6-[(2-nitro-1H-imidazol-1-yl)methyl]-5-oxa-4,8-diazaundecane-2,10-dione dioxime may be prepared stereoselectively by a method comprising the steps of:

(i) reacting (S)-(+1-epichlorohydrin or (R)-(−)-epichlorohydrin with phthalimide to form a stereoisomer of 1-chloro-3-phthalimido-2-propanol;

(ii) contacting the product of (i) with an epoxide ring-forming agent to obtain a stereoisomer of N-(2,3-epoxypropyl)phthalimide;

(iii) contacting the product of (ii) with a base and 2-nitroimidazole to obtain a stereoisomer of 2-[2-hydroxy-2-(nitro-1H-imidazol-1-yl)ethyl]-1H-isoindole-1,3(2H)-dione;

(iv) contacting the product of (iii) with hydrazine, followed by a base and ditertiarybutyl dicarbonate, to obtain a stereoisomer of α-[(t-Boc-amino)methyl]-2-nitro-1H-imidazole-1-ethanol;

(v) contacting the product of (iv) with N-hydroxyphthalimide, triphenylphosphine and diethylazodicarboxylate to obtain a stereoisomer of 2-[1-[(t-Boc-amino)methyl]-2-(2-nitro-1H-imidazol-1-yl)ethoxy]1H-isoindole-1,3(2H)-dione;

(vi) contacting the product of (v) with hydrazine to obtain a stereoisomer of 1-[2(aminooxy)-3-(t-Boc-amino) propyl]-2-nitro-1H-imidazole;

(vii) deprotecting the product of (vi) to obtain a stereoisomer of 1-[3-amino-2-(aminooxy)propyl]-2-nitro-1H-imidazole; and (viii) contacting the product of (vii) with 3-chloro-3-methyl-2-nitrosobutane in the presence of a tertiary amine.

Abbreviations

The following abbreviations are used in the above Examples section:

h=hour(s)

Me=methyl

AcN or ACN or AcCN=acetonitrile

NH$_4$OAc=ammonium acetate

Eg=ethylene glycol

TBATcOCl$_4$=[tetra-n-butyl ammonium][TcOCl$_4$]

MeOH=methanol t-Boc or Boc=tert-butoxycarbonyl

EtOH=ethanol

DMF=dimethylformamide m.p.=melting point

TFA=trifluroacetic acid

THF=tetrahydrofuran

TLC=thin layer chromatography

DMSO=dimethylsulfoxide

IPE=isopropylether

EtOAc=ethyl acetate b.p.=boiling point

What we claim is:

1. A compound of the following formula Ia, Ib or Ic:

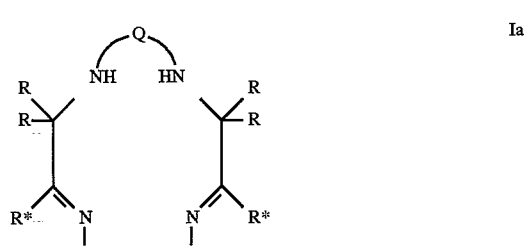

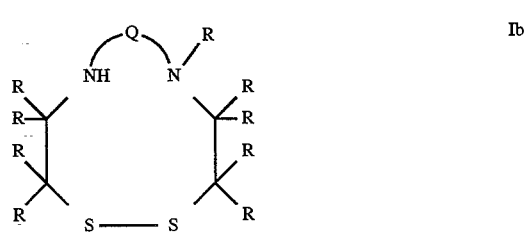

-continued

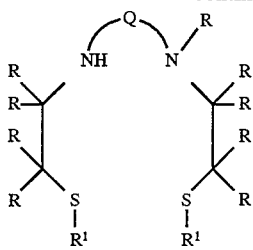

where

Q is the group —(C(RR))$_{m1}$—Y$^1$—(C(RR))$_{m2}$—(Y$^2$—(C (RR))$_{m3}$)$_n$—, where Y$^1$ is —O—, —S—, —SO—, —SO$_2$—, or —Se— and Y$^2$ is independently —NR—, —O—, —S—, —SO—, —SO$_2$—, or —Se—; n is an integer selected from 0 or 1; and m1, m2 and m3 are integers independently selected from 0 to 4, provided that the sum of m1 and m2 is greater than zero; with the proviso that if the compound is of the formula Ic, Y$^1$ is —SO$_2$—, and n=0, then either m1=0 or m2=0;

all R and R* groups are independently:

(i) R$^2$;

(ii) halogen;

(iii) —OR$^2$;

(iv) —C(O)—OR$^2$;

(v) —C(O)—N(R$^2$)$_2$;

(vi) —N(R$^2$)$_2$;

(vii) -alkyl—C(O)—OR$^2$;

(viii) -alkyl—C(O)—N(R$^2$)$_2$;

(ix) -alkyl-N(R$^2$)$_2$;

(x) -aryl-C(O)—OR$^2$;

(xi) -aryl-C(O)—N(R$^2$)$_2$;

(xii) -aryl-N(R$^2$)$_2$;

(xiii) acyl;

(xiv) acyloxy;

(xv) heterocyclo;

(xvi) hydroxyalkyl;

(xvii) —SO$_2$—R$^2$;

(xviii) -alkyl-SO$_2$—R$^2$;

(xix) -(A)p-R$^3$, where A is a linking group, p is 0 or a positive integer, and R$^3$ is a bioactive moiety; or (xx) two R groups, or an R group and an R* group, taken together with the one or more atoms to which they are bonded, form a saturated or unsaturated, spiro or fused, carbocyclic or heterocyclic ring which may be unsubstituted or substituted by one or more groups selected from the groups (i) to (xix) above;

with the proviso that a carbon atom bearing an R group is not directly bonded to more than one heteroatom;

R$^1$ is hydrogen, a thiol protecting group, or the group —(A)p-R$^3$ defined above; and R$^2$ is independently hydrogen, alkyl, alkenyl, alkynyl, or aryl.

2. A compound of the following formula Ia':

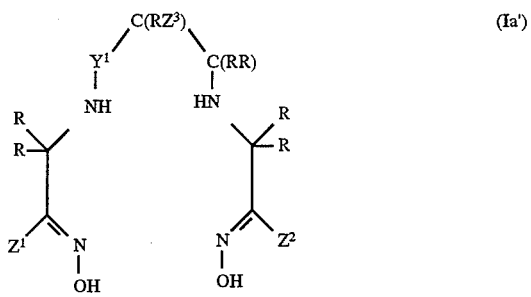

where Z$^1$ and Z$^2$ are R* groups and Z$^3$ is an R group, where one, two or all three of Z$^1$, Z$^2$ and Z$^3$ are -(A)p-R$^3$ groups.

3. A compound of claim 2 where Y$^1$ is —O—.

4. A compound of claim 2 where R$^3$ is a hypoxia-localizing moiety.

5. A compound of claim 4 where the R or groups which are not —(A)$_p$-R$^3$ are hydrogen or alkyl groups.

6. A compound of claim 4 where R$^3$ is a nitroimidazole or nitrofuran group.

7. A compound of claim 1 which is selected from the group consisting of:

3,3,9,9-tetramethyl-5-oxa-4,8-diazaundecane-2,10-dione dioxime;

11-(2-nitro-1H-imidazol-1-yl)-3,5,9,9-tetramethyl-5-oxa-4,8-diazaundecane-2,10-dione dioxime;

1-(2-nitro-1H-imidazol-1-yl)-3,3,9,9-tetramethyl-5-oxa-4,8-diazaundecane-2,10-dione dioxime;

12-2-(2-nitro-1H-imidazol-1-yl)-3,3,9,9-tetramethyl-7-oxa-4,8-diaza-2,10-dodecandedione, dioxime;

12-2-(2-nitro-1H-imidazol-1-yl)-3,3,9,9-tetramethyl-5-oxa-4,8-diaza-2,10-dodecanedione, dioxime;

1,13-bis-(2-nitro-1H-imidazol-1-yl)-4,4,10,10-tetramethyl-6-oxa-5,9-diaza-3,11-tridecanedione, dioxime;

1-[[2-nitro-1H-imidazol-1-yl)acetyl]amino]-3,3,9,9-tetramethyl-5-oxa-4,8-diaza-2,10-undecanedione, dioxime;

1-[2-hydroxy-3-(2-nitro-1H-imidazol-1-yl)propoxy]-3,3,9,9-tetramethyl-5-oxa-4,8-diaza-2,10-undecanedione, dioxime;

1-hydroxy-3,3,9,9-tetramethyl-12-(2-nitro-1H-imidazol-1-yl)-7-oxa-4,8-diazadodecane-2,10-dione, dioxime;

3,3,9,9-tetramethyl-6-[(2-nitro-1H-imidazol-1-yl)methyl]-5-oxa-4,8-diazaundecane-2,10-dione dioxime;

4,4,10,10-tetramethyl-1,13-bis(2-nitro-1H-imidazol-1-yl)-7-[(2-nitro-1H-imidazol-1yl)methyl]-6-oxa-5,9-diazatridecane-3,11-dione, dioxime;

1,13-bis(2-nitro-1H-imidazol-1-yl)-4,4,10,10-tetramethyl-6-oxa-7-(hydroxymethyl)-5,9-diaza-3,11-dodecanedione dioxime;

12-(2-nitro-1H-imidazol-1-yl)-3,3,9,9-tetramethyl-6-(hydroxymethyl)-7-oxa-4,8-diaza-2,10-dodecanedione dioxime;

3,3,9,9-tetramethyl-6-[[3-nitro-1H-imidazol-1-yl)propoxy]methyl]-5-oxa-4,8-diazaundecane-2,10-dione, dioxime;

1-ethoxy-3,3,9,9-tetramethyl-12-(2-nitro-1H-imidazol-1-yl)-6-[(2-nitroimidazol-1yl)methyl]-7-oxa-4,8-diazadodecane-2,10-dione dioxime;

3,3,9,9-tetramethyl-1-ethoxy-6-[(2-nitro-1H-imidazol-1-yl)methyl]-5-oxa-4,8-diazaundecane-2,10-dione dioxime;

4,4,10,10-tetramethyl-7-[(2-nitro-1H-imidazol- 1 -yl)
methyl]-6-oxa-5,9-diazatridecane-3,11-dione dioxime;

4,4,10,10-tetramethyl-7-[(2-nitro-1H-imidazol-1-yl)
methyl]-8-oxa-5,9-diazapentadecane-3,11-dione
dioxime;

5,5,11,11-tetramethyl-1-(5-nitro-2-furyl)-2,9-dioxa-6,10-
diazatetradecane-4,12-dione dioxime;

5,5,11,11-tetramethyl-1-(5-nitro-2-furyl)-2,7-dioxa-6,10-
diazatetradecame-4,12-dione dioxime;

3,3,9,9-tetramethyl-1-[[(5-nitro-2-furyl)carbonyl]amino]-
5-oxa-4,8-diazaundecane-2,10-dione, dioxime; and 3,3,6,9,9-pentamethyl-5-oxa-4,8-diaza-4,8-
diazaundecane-2,10-dione dioxime.

8. A compound which is:

(R)-3,3,9,9-tetramethyl-6-[(2-nitro-1H-imidazol-1-yl)
methyl]-5-oxa-4,8-diazaundecane-2,10-dione dioxime;
or (S)-3,3,9,9-tetramethyl-6-[(2-nitro-1H-imidazol-1-yl)
methyl]-5-oxa-4,8-diazaundecane-2,10-dione dioxime.

9. A compound having the following formula Ia, Ib or Ic:

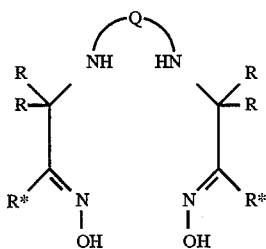

Ia

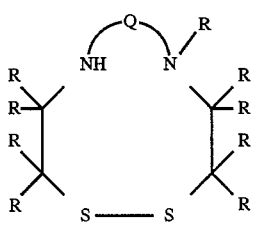

Ib

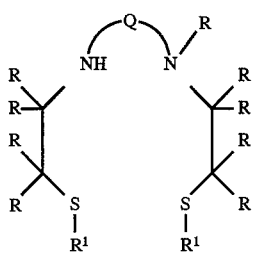

Ic where

Q is the group —$(C(RR))_{m1}$—$Y^1(C(RR))_{m2}$—$(Y^2$—$(C(RR))_{m3})_{m-}$, where $Y^1$ is —O—, and $Y^2$ is independently —NR—, —O—, —S—, —SO—, —$S_2$— or —Se—; n is an integer selected from 0 or 1; and m1, m2 and m3 are integers independently selected from 0 to 4, provided that the sum of m1 and m2 is greater than zero;

all R and R* groups are independently:

(i) $R^2$;

(ii) halogen;

(iii) $OR^2$;

(iv) $C(O)$—$OR^2$;

(v) —$C(O)$—$N(R^2)_2$;

(vi) —$N(R^2)_2$;

(vii) -alkyl-$C(O)$—$OR^2$;

(viii) -alkyl-$C(O)$—$N(R^2)_2$;

(ix) -alkyl-$N(R^2)_2$;

(x) -aryl-$C(O)$—$OR^2$;

(xi) -aryl-$C(O)$—$N(R^2)_2$;

(xii) -aryl-$N(R^2)_2$;

(xiii) acyl;

(xiv) acyloxy;

(xv) heterocyclo;

(xvi) hydroxyalkyl;

(xvii) -$SO_2$—$R^2$;

(xviii) -alkyl-$SO_2$—$R^2$;

(xix) -(A)p-$R^3$, where A is a linking group, p is 0 or a positive integer, and $R^3$ is a bioactive moiety; or (xx) two R groups, taken together with the one or more atom to which they are bonded, form a saturated or unsaturated, or fused, carbocyclic or heterocyclic ring which may be unsubstituted or substituted by one or more groups selected from the groups (i) to (xix) above;

with the proviso that a carbon atom bearing an R group is not directly bonded to more than one heteroatom;

$R^1$ is hydrogen; a thiol protecting group; or the group -(A)p-$R^3$ defined above; and $R^2$ is independently hydrogen, alkyl, alkenyl, alkynyl, or aryl.

10. A compound of claim 9 with the formula Ia.
11. A compound of claim 9 with the formula Ib.
12. A compound of claim 9 with the formula Ic.

* * * * *